US008338099B2

(12) United States Patent
Russwurm et al.

(10) Patent No.: US 8,338,099 B2
(45) Date of Patent: Dec. 25, 2012

(54) REFERENCE GENES FOR THE NORMALIZATION OF GENE EXPRESSION ANALYSIS DATA

(75) Inventors: Stefan Russwurm, Jena (DE); Hans-Peter Saluz, Jena (DE); Hans-Peter Deigner, Lampertheim (DE)

(73) Assignee: SIRS-Lab GmbH, Jena (DE)

( * ) Notice: Subject to any disclaimer, the term of this patent is extended or adjusted under 35 U.S.C. 154(b) by 470 days.

(21) Appl. No.: 12/529,423

(22) PCT Filed: Feb. 28, 2008

(86) PCT No.: PCT/EP2008/001582

§ 371 (c)(1), (2), (4) Date: Mar. 4, 2010

(87) PCT Pub. No.: WO2008/107114

PCT Pub. Date: Sep. 12, 2008

(65) Prior Publication Data

US 2010/0184608 A1 Jul. 22, 2010

(30) Foreign Application Priority Data

Mar. 2, 2007 (DE) ......................... 10 2007 010 252

(51) Int. Cl.
*C12Q 1/68* (2006.01)
*C12P 19/34* (2006.01)
*C07H 21/04* (2006.01)

(52) U.S. Cl. ..................... 435/6.11; 435/6.12; 435/91.2; 536/24.31; 536/24.33

(58) Field of Classification Search ................. 435/6.11, 435/6.12, 91.2; 536/24.31, 24.33
See application file for complete search history.

(56) References Cited

U.S. PATENT DOCUMENTS

| | | | | |
|---|---|---|---|---|
| 2006/0008809 | A1* | 1/2006 | Li et al. | 435/6 |
| 2006/0136145 | A1* | 6/2006 | Kao et al. | 702/20 |
| 2008/0286763 | A1 | 11/2008 | Russwurm et al. | |
| 2009/0246757 | A1* | 10/2009 | Ohto et al. | 435/6 |

FOREIGN PATENT DOCUMENTS

| | | | |
|---|---|---|---|
| DE | 60023496 | T2 | 7/2006 |
| WO | 0071756 | A2 | 11/2000 |
| WO | 2005083115 | A2 | 9/2005 |

OTHER PUBLICATIONS

Database EMBL (Online) Dec. 10, 2003 "*Homo sapiens* proline rich Gla (G-carboxyglutamic acid) 4 (transmembrane), mRNA (cDNA clone MGC:74683 Image: 5183337), complete cds.", XP002660952 found in EBI accession No. EM_HUM:BC063393, Database accession No. BC063393, *Abstract, Sequence *.

European Search Report dated Oct. 26, 2011.

Chemical Abstract AN 146:435738 [Acta Medica Nagasakiensia, 2006, 51(2), 57-63].

Chemical Abstract AN 135:71997 [Journal of Biochemical and Biophysical Methods, 2000, 46(1-2), 69-81].

Medline Abstract AN 2004 545 916 [Journal of Biotechnology, 2004, 114(1-2), 121-124].

Medline Abstract AN 2006 228 769 [Journal of pineal research, 2006, 40(4), 305-11].

Medline Abstract AN 2006 143 439 [Nutrition (Burbank, Los Angeles, Calif.), 2006, 22(4), 408-13).

Bustin SA, Journal of Molecular Endocrinology (2002) 29, 23-39 Quantification of mRNA using real-time reverse transcription PCR (RT-PCR): trends and problems.

Dheda K, et al., BioTechniques (2004) 37:1, 112-119 Validation of housekeeping genes for normalizing RNA expression in real-time PCR.

BMC Journal, BMC Medical Genomics: Identification and Validation of Suitable Endogenous Reference Genes for Gene Expression Studies in Human Peripheral Blood (Stamova, et. al), published: Aug. 5, 2009 http://www.biomedcentral.com/1755-8794/2/49 ISSN 1755-8794.

* cited by examiner

*Primary Examiner* — Kenneth R. Horlick
(74) *Attorney, Agent, or Firm* — Patent Central LLC; Stephan A. Pendorf

(57) ABSTRACT

The present invention relates to reference genes, primers, and probes for the normalization of gene expression analysis data from blood samples of a patient. The invention further relates to a method for the normalization of gene expression analysis data with the aid of reference genes, primers, or probes.

17 Claims, No Drawings

REFERENCE GENES FOR THE NORMALIZATION OF GENE EXPRESSION ANALYSIS DATA

The present invention relates to genes, in particular a set of reference genes for the normalization of gene expression analysis data, PCR primers derived from the reference genes, probes derived from the reference genes, as well as a method for the normalization of gene expression analyses.

There is a persistent demand to identify genes, in particular from blood cells, which exhibit only minimum variation of expression under different conditions. These so-called “housekeeper” or “housekeeping” genes are utilized as references, internal controls and reference values in the quantification of gene expression and of RNA and mRNA by means of methods such as Northern Blotting, Ribonuclease Protection Assay, capillary electrophoresis, microarrays, and quantitative real-time PCR, and by means of further methods for the direct measurement of transcription and measurement after a previous amplification.

In the following, the terms ‘housekeeper’, ‘housekeeping genes’ and ‘expression control genes’ shall be subsumed under the term ‘reference genes’. This simplification is carried out for reasons of easier reading while not constituting any restriction of the invention.

A normalization of quantitative data with the aid of reference genes possesses numerous possible applications. The reference genes allow an identification of genes whose activity is regulated differentially in different pathological conditions, as well as the development of diagnostics based thereon.

A reference gene is a gene that exhibits minimum change of expression and transcription across different RNA samples and thus serves als a control, or reference, for the measurement of variable gene activities across different samples. There is no gene that exhibits unchanged activity across all tissues. Accordingly there is a high demand for new reference genes, in particular for blood, as expression values from blood are employed in diagnosis.

Although various control genes are known from literature [1], no reference genes and transcripts thereof nor their combined use for the normalization of gene expression and transcription from full blood samples and blood cells are known. Transcripts (also, mRNA and microRNA as well as additional RNA) having a constant concentration in blood cells and in cells from organs and peripheral tissue that are located in full blood represent a precondition for the normalization of gene activities and for the determination of the changes of other gene activities, and thus a precondition for blood-based diagnostics. Likewise, various studies for the measurement of gene activity for the diagnosis/prognosis of SIRS and sepsis have already been published, for example [2, 3], however a use and quantification of these gene activity signals by means of reference genes from blood have not been described yet.

Accordingly there is a demand for reference genes from blood and blood cells that are robust and possess stability to allow normalization and quantification of the gene expression of disease-specific genes or gene clusters.

The invention disclosed in the present patent application starts out from the discovery that gene activities of different genes occurring in blood cells in samples of an individual in whom pathological phenomena typical for sepsis (in accordance with the definition in [4]) are detected, do not differ from the gene activities of the same genes of individuals in whom no sepsis was diagnosed, and may jointly or singly be used as reference genes for the normalization of gene activities from blood cells and for the determination of concentration of transcripts from blood. This allows the normalization and relative quantification of the activities of other genes, which may be utilized for diagnosis, prognosis, therapy, and follow-up.

The present invention is therefore based on the object of furnishing means and methods furnishing the possibility of a reference point for the differentiation of changes of gene expression brought about by a medical disorder, and thus a diagnosis or follow-up of the therapy.

The invention describes the identification of new reference genes from blood, suitable microarray probes and PCR primers and their use, also in combination, for the normalization of quantitative expression data from blood and blood cells in microarrays, real-time PCR assays, and other systems with or without amplification and with different visualization options for determination, as well as their utilization for the diagnosis of changes in local inflammations of different localization brought about by a medical disorder and in the systemic reaction thereto, such as SIRS, sepsis, severe sepsis with organ failure.

In these examinations the normalization of gene expression analyses is of crucial importance. For the purposes of the present invention, normalization is intended to be understood as follows:

“Normalization is understood as rendering the measurements of different arrays or PCR or in particular RT-PCR experiments comparable by reducing or removing the technical variability. Within these experiments there exists a multiplicity of sources capable of falsifying the measurements. Possible technical sources of interference are: different efficiency in reverse transcription, labelling or hybridization reactions, as well as problems with the arrays, batch effects in reagents, or lab-specific conditions.”

The method of the invention is characterized in that it is possible to differentiate, in a blood sample of an individual, the activity of one or several genes to be examined through the determination of the presence and quantity of the gene product relative to the quantities of the gene products of the reference genes between SIRS and sepsis.

What is disclosed for this purpose are reference genes and gene sequences from blood and blood cells as well as primers and probes derived therefrom, which may be used for the determination, visualization and normalization and quantification of gene activities and transcripts. The sequences of the oligonucleotide probes in preferred implementation are set forth in Table 1 and correspond to the one in the annexed sequence protocol SEQ ID NO: 1 to SEQ ID NO: 7, primer sequences used in accordance with Table 2 correspond to the one in the annexed sequence protocol SEQ ID NO: 8 to SEQ ID NO: 21. The sequences of the oligonucleotide probes may also assume other sequences, in preferred implementation having a length of 50-100 nucleotides, which specifically bind transcripts of the genes set forth in Table 3 with sequences SEQ ID NO: 22 to SEQ ID NO: 97. The sequences used in amplification methods such as PCR may have a random length as long as they support the desired enzymatic manipulation and amplification.

TABLE 1

DNA Oligonucleotide Probes

| Gene Symbol | SEQ ID NO: |
|---|---|
| ITGAL | 1 |
| SNAPC1 | 2 |
| CASP8 | 3 |

TABLE 1-continued

| DNA Oligonucleotide Probes | |
|---|---|
| Gene Symbol | SEQ ID NO: |
| C7 | 4 |
| PPARD | 5 |
| IL18 | 6 |
| F3 | 7 |

TABLE 2

| Forward and Reverse DNA Primers | | |
|---|---|---|
| Gene Symbol | Forward Primer SEQ ID NO: | Reverse Primer SEQ ID NO: |
| ITGAL | 8 | 15 |
| SNAPC1 | 9 | 16 |
| CASP8 | 10 | 17 |
| C7 | 11 | 18 |
| PPARD | 12 | 19 |
| IL18 | 13 | 20 |
| F3 | 14 | 21 |

TABLE 3

| Reference Genes (RNA Sequences) | |
|---|---|
| GenBank Accession Number | SEQ ID NO: |
| NM_024081 | 22 |
| AA398364 | 23 |
| N34546 | 24 |
| AA659421 | 25 |
| AA682479 | 26 |
| AK024118 | 27 |
| AA923316 | 28 |
| BM309952 | 29 |
| AI093653 | 30 |
| AI131415 | 31 |
| AI263527 | 32 |
| AA282242 | 33 |
| CR740270 | 34 |
| BG191861 | 35 |
| AI301257 | 36 |
| AI310464 | 37 |
| AW964023 | 38 |
| AI351933 | 39 |
| AA100540 | 40 |
| AI362368 | 41 |
| AI817134 | 42 |
| AI381377 | 43 |
| AI520967 | 44 |
| AA253470 | 45 |
| AI559304 | 46 |
| AI565002 | 47 |
| AI587389 | 48 |
| AI609367 | 49 |
| AI635278 | 50 |
| AI702056 | 51 |
| AI707917 | 52 |
| AI733176 | 53 |
| AI769053 | 54 |
| AI798545 | 55 |
| AI801425 | 56 |
| AI801595 | 57 |
| AI809873 | 58 |
| AI862063 | 59 |
| AI923251 | 60 |
| AI925556 | 61 |
| AI932551 | 62 |
| AI932884 | 63 |
| AI933797 | 64 |
| AI933967 | 65 |
| AI935874 | 66 |

TABLE 3-continued

| Reference Genes (RNA Sequences) | |
|---|---|
| GenBank Accession Number | SEQ ID NO: |
| H06263 | 67 |
| H22921 | 68 |
| H54423 | 69 |
| N22551 | 70 |
| N73510 | 71 |
| R06107 | 72 |
| R42511 | 73 |
| R43088 | 74 |
| NM_181705 | 75 |
| R92455 | 76 |
| R93174 | 77 |
| T77995 | 78 |
| T79815 | 79 |
| T83946 | 80 |
| T95909 | 81 |
| T98779 | 82 |
| AK127462 | 83 |
| W80744 | 84 |
| W86575 | 85 |
| AJ297560 | 86 |
| NM_001562 | 87 |
| BU629240 | 88 |
| NM_001228 | 89 |
| NM_001993 | 90 |
| NM_002209 | 91 |
| NM_002392 | 92 |
| NM_000587 | 93 |
| NM_004379 | 94 |
| BC002715 | 95 |
| NM_003082 | 96 |
| AA664688 | 97 |

The primers in Table 2 may be used for producing amplification products containing the desired region (sequence) of the named genes. In customary implementation, the product has a length of 150-200 nucleotides.

The reference genes may be used singly or in combination of several ones. Customarily the activity of reference genes as presently described may be determined with the aid of hybridization probes for microarrays or PCR primers and real-time PCR. The reference genes and their expression products may, however, also be determined after amplification by other methods that are known to the person having skill in the art, such as e.g., NAsRA (Nucleic Acid Sequence-Based Amplification) and in various combination. They may also be determined with the aid of a number of further methods or visualization options such as, e.g., with the aid of monoclonal antibodies. Primers and probes may be employed for the gene, the expression product (mRNA), or intermediate expression products which are not processed entirely into mRNA.

In other embodiments the primers and probes bind a specific region of the presently disclosed reference genes or of transcripts thereof. The probes and primers may, however, interact with any region of the presently disclosed gene sequences or sequences transcribed therefrom. The primers and probes may interact via successive base pairing, however need not necessarily interact with the complete complementary sequence. The buffer compositions, salt concentrations, washing steps and temperatures may here be selected to be variable.

Likewise, these changes of the reference genes and of the test genes may be compared to the expression values (or data derived therefrom such as, e.g., average values) of one or several reference samples that are not determined concurrently with the target sample.

One embodiment of the invention is characterized in that expression values are determined by using reference genes in accordance with Table 3 as well as nucleic acids and transcripts of these reference genes from blood and from blood cells as reference genes by way of comparison of the expression values to one or several test nucleic acids and by quantification relative to the test nucleic acid.

One further embodiment of the invention is characterized in that nucleic acids and DNA probes having the sequences according to Table 1 and their binding of RNA, including microRNA, and of transcripts (RNA or mRNA) in blood or from blood cells of genes according to Table 3 in solution or immobilized on surfaces or particles or beads and the use of the bound transcripts of these genes are used for normalization by comparison of the bound quantities (expression values) of the nucleic acids to one or several test nucleic acid(s) bound to probes, and for quantification relative to the bound test nucleic acid.

One embodiment of the invention is characterized in that the method for ex vivo, in vitro differentiation between SIRS and sepsis (both in correspondence to [4]) based on establishing a relation between the RNA quantities from reference gene and test gene includes the following steps:

a) isolating reference gene RNA and test gene RNA from a blood sample,
b) marking the reference gene RNA and test gene RNA with a detectable marker and contacting with the DNA under hybridization conditions, the DNA being a gene fragment or oligonucleotide which specifically binds transcripts, amplification products, or in vitro transcripts of reference genes,
c) quantitatively detecting the marking signals of the reference gene RNA and test gene RNA in accordance with b), and
d) comparing the quantitative data of the marking signals in order to give a statement whether a specific gene or gene fragment are expressed more strongly or more weakly in comparison with the signals of the reference genes.

Another embodiment of the invention is characterized in that the reference gene RNA is hybridized with the DNA prior to measurement of the test gene RNA, and the marking signals of the control RNA/DNA complex are detected, in a given case transformed further, and in a given case stored in the form of a calibration curve or table.

Another embodiment of the invention is characterized in that RNA of the reference genes or parts thereof are identified and quantified by way of sequencing or partial sequencing, for instance by way of pyrosequencing.

Another embodiment of the invention is characterized in that mRNA or microRNA is used as reference gene RNA.

Another embodiment of the invention is characterized in that the DNA is disposed, in particular immobilized, for specific binding of the reference gene RNA or its in vitro transcripts in predetermined regions on a support having the form of a microarray.

Another embodiment of the invention is characterized in that the biological sample is that of a human being.

These sequences having SEQ ID NO: 1 to SEQ ID NO: 97 are encompassed in the scope of the present invention and are disclosed in detail in the annexed, 70-page sequence protocol including 107 sequences which thus forms part of the invention.

Another embodiment of the invention is characterized in that the immobilized or free probes are marked with sequences corresponding to Table 1. For this embodiment, self-complementary oligonucleotides, so-called molecular beacons, are employed as probes. At their ends they carry a fluorophore/quencher pair, so that in the absence of a complementary sequence they are present in a folded hairpin structure and furnish a fluorescence signal only with a corresponding sample sequence. The hairpin structure of the molecular beacons is stable until the sample hybridizes at the specific catcher sequence, resulting in a change of conformation and thus also in a release of the reporter fluorescence.

Another embodiment of the invention is characterized in that at least 1 to 14 nucleic acid probes or their complements are used for binding the transcripts, or the complements thereof, of the reference genes.

Another embodiment of the invention is characterized in that the synthetic analoga of the reference genes, or the synthetic oligonucleotides which bind the transcripts of the reference genes, in particular include approx. 60 base pairs.

Another embodiment of the invention is characterized in that the genes listed as DNA in the claims are replaced by sequences derived from their RNA, synthetic analoga, aptamers, and peptidonucleic acids.

Another embodiment of the invention is characterized in that a radioactive marker, in particular $^{32}P$, $^{14}C$, $^{125}I$, $^{33}P$ or $^{3}H$, is used as a detectable marker.

Another embodiment of the invention is characterized in that a non-radioactive marker, in particular a dye or fluorescence marker, an enzyme marker or immune marker, and/or quantum dots or an electrically measurable signal, in particular changes of potential and/or conductivity and/or capacity in hybridizations, is used as a detectable marker.

Another embodiment of the invention is characterized in that the sample RNA and reference gene RNA and/or enzymatic or chemical derivatives carry the same marking.

Another embodiment of the invention is characterized in that the test gene RNA and reference gene RNA and/or enzymatic or chemical derivatives carry different markings.

Another embodiment of the invention is characterized in that the DNA probes are immobilized on glass or plastic.

Another embodiment of the invention is characterized in that the single DNA molecules are immobilized through a covalent binding to the support material.

Another embodiment of the invention is characterized in that the single DNA molecules are immobilized to the support material by means of electrostatic and/or dipole-dipole and/or hydrophobic interactions and/or hydrogen bridges.

Another embodiment of the invention consists in the use of recombinant or synthetically produced, specific reference gene nucleic acid sequences, partial sequences singly or in partial quantities as a calibrator in sepsis assays and/or for the evaluation of effect and toxicity in active agent screening and/or for the production of therapeutics and of substances and mixtures of substances intended as a therapeutic, for the prophylaxis and treatment of SIRS and sepsis.

The person having skill in the art will be aware that the single features of the invention as set forth in the claims may be combined at will without any restrictions.

Reference genes within the meaning of the invention are understood to be any derived DNA sequences, partial sequences and synthetic analoga (e.g., peptidonucleic acids, PNA). The description of the invention relating to determination of the gene expression on the RNA level does not constitute a restriction but only an exemplary application.

One application of the method of the invention resides in the normalization of measurement data of the differential gene expression from full blood, for instance for the differentiation between SIRS and sepsis and their degrees of severity (both in correspondence to [4]). To this end, the RNA of the reference genes is isolated from the full blood of corresponding patients and from a control sample of a healthy test person or non-infectious patient. The RNA is subsequently marked, for instance radioactively with $^{32}P$, or with dye molecules (fluorescence). Any molecules and/or detection signals that are known for this purpose in the prior art may be utilized as marking molecules. Corresponding molecules and/or methods are equally known to the person having skill in the art.

The RNA thus marked is subsequently hybridized with DNA molecules immobilized on a microarray. The DNA molecules immobilized on the microarray represent a specific selection of the genes in accordance with the present invention for the normalization of gene expression data in the differentiation of SIRS and sepsis.

The intensity signals of the hybridized molecules are then measured by suitable measurement apparatus (Phosporimager, microarray scanner) and analyzed by further software-supported evaluations. The expression ratios between the test genes of the patient sample and the reference genes are determined from the measured signal intensities. From the expression ratios of the under- and/or over-regulated genes it is possible to draw conclusions as to the differentation between SIRS and sepsis as in the experiments represented hereinbelow.

Another application of the gene activities determined by way of microarray analysis with subsequent quantification for the normalization of gene expression data consists in the application for the differentiation of SIRS and sepsis for the further electronic processing for the purpose of producing software for diagnostic purposes (e.g., for the determination of the localization of an inflammation and for assessing the severity of affliction of an individual immune response particularly with infections, also in the framework of patient data management systems or expert systems) or for modelling cellular signal transmission paths.

The following applies to the implementation of the evaluation of the microarrays for the purposes of the present patent application:

Microarray Experimental Description (According to the Minimum Information About a Microarray Experiment [MIAME] Checklist—New edition January 2005, based on Brazma A et al., Minimum information about a microarray experiment (MIAME)—toward standards for microarray data, Nature Genetics 29, 365-371 (2001) [17], the contents of which are fully incorporated herein by way of reference)

Reading in of Slides/Scanner Technical Specifications

| | | |
|---|---|---|
| a) Scanner: | GenePix 4000B confocal incident-light fluorescence scanner (Axon Instruments) | |
| b) Scanning software: | GenePix Pro 4.0 | |
| c) Scanning parameters: | Laser power: | Cy3 channel - 100%<br>Cy5 channel - 100% |
| | PMT voltage: | Cy3 channel - 700 V<br>Cy5 channel - 800 V |
| d) Spatial resolution (pixel space) - 10 μm. | | |

Reading Out and Processing of Data

In the framework of the experiments, more than 1,000 blood samples of patients were hybridized. Each RNA pair (patient versus comparative RNA) was co-hybridized on a microarray. The patient RNA was marked with a red fluorescent dye, and the comparative RNA with a green fluorescent dye. The digitized images of the hybridized array were evaluated with the GenePix Pro 4.0 or 5.0 software by Axon Instruments. For spot detection, signal quantification and evaluation of the spot quality, the GenePix™ analysis software was used. The spots were marked, in accordance with the settings in the GenePix™ software, as 100="good", 0="found", −50="not found", −75="absent", −100="bad." The raw data was stored in a corresponding *.gpr file.

Normalization, Transformation and Data Selection Method e) Transformation and Normalization of the Signal Data For the normalization and variance-stabilized transformation of the raw data the method of Huber et al. [5] was used, in which the additive and multiplicative errors are estimated block by block. About 75% of all the spots are utilized for this. The signals are then transformed by the arsinh function. (Thus, the transformed ratio of ±0.4 about corresponds to a 1.5-fold change {for large numbers, arsinh (x) is nearly identical with Ln (2x)}.

Rocke D M, Durbin B, A model for measurement error for gene expression arrays, J Comput Biol. 2001; 8(6):557-69 [18], have developed a model for estimating the measurement error in gene expression arrays as a function of the expression level, the contents of which are hereby fully incorporated by way of reference. This error model in combination with further analysis methods, data transformations and weightings, already allows a more accurate comparison of the gene expression data and furnishes guidelines for background analysis, determination of confidence intervals and processing of the analysis data for their multivariate further processing or analysis, respectively.

Based on the above-mentioned error model by Rocke and Durbin [18], Huber W, Heydebreck A, and Sueltmann H, Variance stabilization applied to microarray data calibration and to the quantification of differential expression, Bioinformatics. 2002; 18 Suppl 1:pp. 96-104 [19], have developed a statistical model for microarray gene expression data, the contents of which are hereby fully incorporated by way of reference. The model includes a data calibration, the quantification of different expression levels, as well as the quantification of the measurement error. In this regard, Huber et al. [19] derived a data transformation for signal intensity measurements and a difference statistic, which results in a variance stabilization and normalization of a set of signal data across its entire intensity range by using the area function arsinh. This method was in particular demonstrated on microarray gene expression data but is also transposable to other methods for gene expression measurement in the framework of the present invention.

Hereby the dependency of variance on signal intensity, which is frequently observed in the evaluation of signals, is compensated by the mentioned transformation with the aid of the area function.

f) Filtration

The technical replicates (multiple spots of a same sample) on the microarray are filtered out from the corrected and transformed signal intensities in dependence on their spot quality. For each spot the replicates having the highest characterization are selected, and the associated signal intensity is averaged. The expression of spots having exclusively non-measurable replicates are designated "NA" (not available).

Another application of the method of the invention consists in measuring the differential gene expression for the determination, concurrently with the therapy, of the probability that patients will respond to the projected therapy, and/or for the determination of the response to a specialized therapy and/or to the fixation of the end of therapy in the sense of a "drug monitoring" in patients with SIRS and sepsis and their degrees of severity. To this end, the RNA (test RNA and control RNA) is isolated from the patient's blood samples that were collected at temporal intervals. The different RNA samples are marked jointly and hybridized with selected test genes and with reference genes immobilized on a microarray. From the expression ratios between single or several reference genes and test genes such as, e.g., TNF alpha it is thus possible to evaluate the probability that patients will respond to the projected therapy and/or whether the begun therapy is effective and/or how much longer the patients will have to be therapied correspondingly and/or whether the maximum therapy effect has already been reached with the dose and duration employed. Another application of the method of the invention consists in the use of the RNA of the genes in accordance with the invention for obtaining quantitative information through hybridization-independent methods, in particular enzymatic or chemical hydrolysis, Surface Plasmon Resonance methods (SPR methods), subsequent quantification of the nucleic acids and/or of derivatives and/or fragments of these.

The transcripts of reference genes amplified and quantified by means of PCR (and also additional amplification methods such as NASBA) constitute another embodiment in accordance with the present invention for the normalization of gene expression data in the differentiation of SIRS and sepsis and their degrees of severity. The intensity signals of the amplified transcripts are then measured by suitable measurement apparatus (PCR fluorescence detector) and analyzed with the aid of further software-supported evaluations. From the measured signal intensities the expression ratios between the test genes of the patient sample and the reference genes are determined. From the expression ratios of the under- and/or over-regulated genes it is possible—as in the experiments represented hereinbelow—to draw conclusions as to the differentiation between SIRS and sepsis and their degrees of severity.

Another application of the method of the invention consists in the use of the gene activities determined by way of PCR or other amplification methods with subsequent quantification for the normalization of gene expression data for the differentiation of SIRS and sepsis and their degrees of severity for the electronic further processing for the purpose of producing software for diagnostic purposes (e.g., for the determination of the focus of an inflammation and for an assessment of the severity of an individual immune response in particular with bacterial infection, also in the framework of patient data management systems or expert systems) or for modelling cellular signal transmission paths.

Another application of the method of the invention consists in the determination of an mRNA quantity in a sample, including a) isolation of the nucleic acids, b) a measurement of the expression value of one or several nucleic acids selected from SEQ ID NO: 22 to SEQ ID NO: 97; c) a comparison of the expression values of the selected nucleic acids to known percentage values of the nucleic acids in the total quantity of mRNA; d) extrapolation of the expression values of one or several nucleic acids selected from SEQ ID NO: 22 to SEQ ID NO: 97 to the total quantity of mRNA, and d) determination of the total quantity of mRNA in the sample.

Another application of the method of the invention consists in the normalization of an mRNA quantity—in a given case amplified—in several samples, including a) a comparison of the expression values of one or several nucleic acids selected from SEQ ID NO: 22 to SEQ ID NO: 97 across various samples; b) deriving a value for the normalization of expression values of one or several nucleic acids selected from SEQ ID NO: 22 to SEQ ID NO: 97 across several samples; and c) a normalization of the expression of other nucleic acids that were isolated from several samples, based on step b).

The invention may further relate to a kit containing a selection of sequences in accordance with SEQ ID NO: 22 to SEQ ID NO: 97 and/or gene fragments thereof including at least 1-100, in preferred embodiments 1-5 and 1-10 nucleotides, for the in vitro determination of gene expression profiles in a patient sample, for the use as reference genes.

The invention may further also relate to a kit containing a selection of hybridization probes in accordance with SEQ ID NO: 1 to SEQ ID NO: 7 and/or gene fragments thereof including at least 50 nucleotides for the in vitro determination of gene expression profiles in a patient sample, for the use as reference genes.

The invention may equally relate to a kit containing a selection of primer probes in accordance with SEQ ID NO: 8 to SEQ ID NO: 21 and/or gene fragments thereof including at least 15 nucleotides for the in vitro determination of gene expression profiles in a patient sample, for the use as reference genes.

In its broadest and most general formulation, the present invention relates to the following embodiments:

A) At least one reference gene for the normalization of gene expression analysis data from blood samples of a patient, wherein the reference gene is selected from the following RNA sequences: SEQ ID NO: 22 to SEQ ID NO: 97, in particular SEQ ID NO: 87, SEQ ID NO: 89, SEQ ID NO: 90, SEQ ID NO: 91, SEQ ID NO: 93, SEQ ID NO: 95, and SEQ ID NO: 96.

B) At least one primer, derived from the reference genes in accordance with A) for the normalization of gene expression analysis data based on nucleic acid amplification, from blood samples of a patient, wherein the primer is selected from the following DNA sequences: SEQ ID NO: 8 to SEQ ID NO: 21.

C) At least one probe, derived from the reference genes in accordance with B) for the normalization of gene expression analysis data from blood samples of a patient, wherein the set of probes includes the following DNA sequences: SEQ ID NO: 1 to SEQ ID NO: 7, as well as their complementary nucleic acid sequences.

D) A method for the normalization of gene expression analysis data with the aid of at least one control nucleic acid selected from the reference genes in accordance with A) or a set of primers in accordance with B) or a set of probes in accordance with C), wherein a) at least one gene expression analysis assay is carried out in vitro on blood samples of a patient;

b) at least one control nucleic acid in the same assay is jointly examined as a basis for the normalization of the gene expression analysis data of the samples to be examined;

c) signals from the gene expression analyses are detected, which reflect the degree of the gene expression of a plurality of genes and of the at least one control nucleic acid;

d) the signal data obtained in step c) is subjected to a mathematical transformation in order to at least weaken the technical variability of the signal data; and thereby e) to normalize the signal data of the samples to be examined.

E) Preferred embodiments of the method in accordance with D) are:

A method according to D), wherein the mathematical transformation of the signal data is carried out by means of the arsinh or by means of a logarithmic approach;

and/or the gene expression assay is selected from:

f) isolation of nucleic acids from a blood sample;

g) in a given case a co-amplification of a set of control nucleic acids and the nucleic acids to be tested; and h) probe hybridization;

and/or the nucleic acids include mRNA or microRNA;

and/or the nucleic acids are amplified by means of PCR, real-time PCR, NASBA, TMA, or SDA;

and/or the expression values of the control and test nucleic acids are determined by means of hybridization methods;

and/or the measurement of the expression values of the control and/or test nucleic acids takes place in solution or on nucleic acids immobilized on a support;

and/or the support is a microarray, particle, bead, glass, metal or membrane;

and/or the control and/or test nucleic acids are indirectly coupled to the support with the aid of other binding partners such as antibodies, antigenes, oligonucleotides, molecular beacons, or enzymes;

and/or the expression values of the control and test nucleic acids determined in vitro from a sample of a patient are utilized as input parameters for the production of software for the description of the individual prognosis of a patient, for diagnostic purposes, for therapy decisions and/or patient data management systems.

F) A use of at least one control nucleic acid, selected from the reference genes in accordance with A) or a primer in accordance with B) or a probe in accordance with C), for the normalization of a gene expression analysis method for the diagnosis of disorders involving systemic immune reaction.

G) Preferred embodiments of the use in accordance with F) are:

A use according to F), wherein the disorders are selected from: sepsis, severe sepsis, septic shock, or multiple organ failure;

and/or in a method for in vitro diagnosis of SIRS, sepsis, severe sepsis, septic shock or multiple organ failure in an individual by using sets of control nucleic acids and test nucleic acids, the expressions of which are specific for SIRS or sepsis, including the following steps:

a) concurrent isolation of the control and test nucleic acids from a sample of the individual, b) in a given case, amplification of the control and test nucleic acids, c) determination of the expression values of the control and test nucleic acids, d) a normalization of the gene expression of the test nucleic acids based on the expression values of the control nucleic acids, e) determination whether the normalized expression values of the test nucleic acid have reached a specific value for SIRS, sepsis, severe sepsis, septic shock, or multiple organ failure.

The following also fundamentally applies for data transformation/normalization in the framework of the present invention:

1st Variant (suggested for normalization in PCR experiments or also in small diagnostic arrays):

The signals of the reference genes are aggregated, and subsequently the ratio of the signals of the test genes to the aggregated signal of the reference genes is calculated. In the case of logarithmed signals the ratio then consists of the difference.

2nd Variant (e.g., Huber et al. [19] in "whole genome" approaches or large arrays): The signals of the reference genes are used to estimate the parameters of a suitable transformation or the transformation itself.

This transformation is then applied to the test genes

Further advantages and features of the present invention become evident from the description of practical examples.

PRACTICAL EXAMPLE 1

Identification of Reference Genes from Blood and from Blood Cells

Measurement of the Gene Expression:

The gene expression of 372 intensive therapy unit patients (ITU patients) was measured. All of the patients were under intensive-care medical treatment. A maximum of seven ITU days was considered for each patient. In patients with more than seven ITU days, seven days were selected randomly. All in all, the data of 1261 microarray experiments entered the analyses.

Selected characteristics of the patients are represented in Tables 4 and 5. Information is provided with regard to age, sex, and ACCP/SCCM categories. The total RNA from cell lines SIG-M5 served as reference samples. All of the patient samples were each co-hybridized with the reference sample on one respective microarray.

TABLE 4

| General data of the patients | |
|---|---|
| No. of patients (microarrays) | 372 (1261) |
| Mortality | 94 (25.3%) |
| Sex [F/M] | 113/259 |
| Age in years | 68 (15) |
| APACHE-II | 16 (9) |
| SAPS-II | 32 (15) |
| SOFA | 8 (4) |
| Duration of hospitalization in days | 8 (22) |

The respective indications are the median and the Inter-Quartile Range (IQR) in parentheses

TABLE 5

Indications subject to operations regarding the as-is analysis (multiple entries possible)

| Indication | No. of patients |
|---|---|
| Coronary vessels | 153 |
| Heart valves | 65 |
| Gastrointestinal | 34 |
| Thorax | 17 |
| Polytrauma | 13 |
| Peripherala hear vessels | 8 |
| Uro-genital | 8 |
| Neurosurgery | 6 |

Experimental Description:

Taking Blood and RNA Isolation

The patients' full blood was taken from the patients in the intensive care unit by means of the PAXGene Kit in accordance with the manufacturer's (Qiagen) specifications. Following taking of the full blood, the total RNA of the samples was isolated by using the PAXGene Blood RNA Kit in accordance with the manufacturer's (Qiagen) specifications.

Cell Cultivation

For the cell cultivation (control samples) 19 cryocell cultures (SIGM5) (frozen in liquid nitrogen) were utilized. The cells were each inoculated with 2 ml of Iscove's Medium (Biochrom AG) supplemented with 20% fetal calf serum (FCS). The cell cultures were then incubated for 24 hrs at 37° C. under 5% $CO_2$ in 12-well plates. Then the contents of 18 wells were divided into 2 parts each having a same volume, so that finally 3 plates of a same format (total of 36 wells) were available. Cultivation was then continued for 24 hrs under the same conditions. After this, the resulting cultures of 11 wells of each plate were united and centrifuged (1000×g, 5 min, room temperature). The supernatant was discarded, and the cell pellet was dissolved in 40 ml of the above-identified medium. These 40 ml of dissolved cells were evenly divided into two 250-ml test tubes and following 48 hrs of incubation and addition of 5 ml of the above-identified medium were incubated once more. Of the remaining 2 ml of the two remaining plates, 80 μl were placed in empty wells of the same plates which had already been prepared in advance with 1 ml of the above-identified medium. After 48 hrs of incubation, only one of the 12 well plates was processed as follows: From each well 500 μl was taken and united. The resulting 6 ml was placed in a 250-ml test tube containing approx. 10 ml of fresh medium. This mixture was centrifuged at 1000×g for 5 minutes at room temperature and dissolved in 10 ml of the above-identified medium. The subsequent cell count yielded the following result: $1.5\times10^7$ cells per ml, 10 ml total volume, total number of cells: $1.5\times10^8$. As the cell number was not sufficient yet, 2.5 ml of the above-identified cell suspension was placed in 30 ml of the above-identified medium in a 250-ml (75 $cm^2$) test tube (altogether 4 test tubes). After an incubation time of 72 hrs, 20 ml each of fresh medium was placed in the test tube. Following 24 hrs of incubation, the cell count was performed in accordance with the above description and resulted in a total cell number of $3.8\times10^8$ cells. In order to obtain the desired cell number of $2\times10^6$ cells, the cells were resuspended in 47.5 ml of the above-identified medium in 4 test tubes. After an incubation period of 24 hrs, the cells were centrifuged and washed twice with phosphate buffer without $Ca^{2+}$ and $Mg^{2+}$ (Biochrom AG).

Isolation of the total RNA takes place by means of the NucleoSpin RNA L Kit (Machery&Nagel) in accordance with the manufacturer's specifications. The above-described procedure was repeated until the required cell number was obtained. This was necessary in order to obtain the required amount of 6 mg of total RNA, approximately corresponding to an efficiency of 600 μg of RNA per $10^8$ cells.

Reverse Transcription/Marking/Hybridization

Following taking of the full blood, the total RNA of the samples was isolated and examined as to its quality by using the PAXGene Blood RNA Kit (PreAnalytiX) in accordance with the manufacturer's specifications. From each sample 10 μg of total RNA was aliquoted and rewritten, together with 10 μg of total RNA from SIGM5 cells as reference RNA, into complementary DNA (cDNA) with Reverse Transcriptase Superscript II (Invitrogen), and the RNA was subsequently removed from the batch by alkaline hydrolysis. In the reaction batch a part of the dTTP was replaced with aminoallyl-dUTP (AA-dUTP) in order to allow coupling of the fluorescent dye to the cDNA later on.

Following purification of the reaction batch, the cDNA of the samples and controls were marked covalently with the fluorescent dyes Alexa 647 and Alexa 555 and hybridized on a microarray of the company SIRS-Lab. On the microarray used there are 5,308 immobilized polynucleotides having a length of 55-70 base pairs each representing one human gene, and control spots for quality assurance. One microarray is subdivided into 28 sub-arrays having a raster of 15×15 spots.

Hybridization and subsequent washing and drying, respectively, were carried out in the hybridization station HS 400 (Tecan) in accordance with the manufacturer's specifications during 10.5 hrs at 42° C. The hybridization solution used consists of the respective marked cDNA samples, 3.5×SSC (1×SSC contains 150 mM sodium chloride and 15 mM sodium citrate), 0.3% sodium dodecyl sulfate (V/V), 25% formamide (V/V), and 0.8 μg μl-1 cot-1 DNA, yeast t RNA and poly-A RNA each. The subsequent washing of the microarrays was carried out with the following program at room temperature: 90 seconds each rinsing with washing buffer 1 (2×SSC, 0.03% sodium dodecyl sulfate), with washing buffer 2 (1×SSC), and finally with washing buffer 3 (0.2×SSC). Then the microarrays were dried under a nitrogen flow at a pressure of 2.5 bars at 30° C. during 150 seconds.

Following hybridization, the hybridization signals of the microarrays were read out with the aid of a GenePix 4000B scanner (Axon), and the expression ratios of the differenciated expressed genes were determined with the aid of the software GenePix Pro 4.0 (Axon).

Evaluation:

For the evaluation, the mean intensity of a spot was determined as the median value of the associated spot pixel.

Pre-Selection of Gene Samples:

For a first pre-selection of the gene probes the correction of systematic errors was performed in accordance with the approach of Huber et al. [5]. Additive and multiplicative bias within a microarray was estimated from 75% of the gene samples present.

Subsequently the normalized and transformed ratios of the signals of the patient samples were calculated versus the general control. I.e., for the j-th gene of the k-th array the calculation yielded the value $$G_{j,k}=\text{arsinh}(Scy5(j,k)-\text{arsinh}(Scy3(j,k))$$

wherein [Scy3(j,k), Scy5(j,k)] designates the related fluorescence signal pair. For all of the gene probes the median of the absolute deviations from the median (MAD), i.e. MAD ($G_j$, 1, . . . , $G_j$, 1261), was subsequently calculated, and the 10% gene probes having the lowest MAD were selected. As the second criterion for the pre-selection the mean signal intensity arsinh(Scy5(j,k))+arsinh(Scy3(j,k)) was employed. In the further analyses, only gene probes having a median of the mean signal intensity in the so-called dynamic signal range, preferably between 6 and 8 (on the logarithmic scale), were taken into consideration.

Selection of the Reference Genes:

For the gene probes selected in advance, relative quantities were calculated by setting the highest expression value to 1. Subsequently the gene stability measure M of Vandesompele et al. [6] was calculated. By means of the stepwise procedure, equally described in Vandesompele et al., in which the gene having the lowest stability is removed in each step, the gene probes were arranged in accordance with their stability. The upper threshold value for the selection of the gene probes was based on the (rounded) value 0.6 for the mean value of the stability measure M (Table 6).

The mathematical definition for the gene stability measure M in accordance with Vandesompele et al. is:

For each combination of two internal reference genes j and k, an array $A_{jk}$ of m elements is given which consists of the $log_2$-transformed expression ratios $a_{ij}/a_{ik}$ (Equation 1). The paired variation $V_{jk}$ for the reference genes j and k is furthermore defined as the standard deviation of the elements $A_{jk}$ (Equation 2), with SD being the standard deviation. The gene stability measure $M_j$ for the reference gene j then is the arithmetical mean of all paired variations $V_{jk}$ (Equation 3):

(For every j,k: [1,n] and j k):

$$A_{jk} = \left[\log_2\left(\frac{a_{1j}}{a_{1k}}\right), \log_2\left(\frac{a_{2j}}{a_{2k}}\right), \ldots, \log_2\left(\frac{a_{mj}}{a_{mk}}\right)\right] = \left[\log 2\left(\frac{a_{ij}}{a_{ik}}\right)\right]_{i=1\to m} \quad (1)$$

$$V_{jk} = SD(A_{jk}) \quad (2)$$

$$Mj = \frac{\sum_{k=1}^{n} V_{jk}}{n-1} \quad (3)$$

A cluster was determined on 76 specific sequences having unchanged gene activity corresponding to SEQ ID NO: 22 to SEQ ID NO: 97 that are part of the annexed sequence protocol.

TABLE 6

Determined reference genes (RNA base) and their stability values

| SEQ ID NO: | GenBank Accession Number | MAD of the Signal Ratios | Median of the Mean Intensities | Stability M |
|---|---|---|---|---|
| 22 | NM_024081 | 0.200 | 7.190 | 0.368 |
| 23 | AA398364 | 0.179 | 6.730 | 0.385 |
| 24 | N34546 | 0.171 | 6.265 | 0.401 |
| 25 | AA659421 | 0.212 | 7.127 | 0.380 |
| 26 | AA682479 | 0.218 | 6.209 | 0.373 |
| 27 | AK024118 | 0.172 | 6.601 | 0.457 |
| 28 | AA923316 | 0.197 | 6.891 | 0.374 |
| 29 | BM309952 | 0.205 | 7.533 | 0.417 |
| 30 | AI093653 | 0.156 | 7.120 | 0.355 |
| 31 | AI131415 | 0.156 | 6.881 | 0.413 |
| 32 | AI263527 | 0.173 | 6.614 | 0.379 |
| 33 | AA282242 | 0.181 | 6.758 | 0.381 |
| 34 | CR740270 | 0.191 | 6.360 | 0.346 |
| 35 | BG191861 | 0.191 | 6.292 | 0.377 |
| 36 | AI301257 | 0.244 | 6.039 | 0.401 |
| 37 | AI310464 | 0.202 | 6.229 | 0.423 |
| 38 | AW964023 | 0.204 | 6.776 | 0.380 |
| 39 | AI351933 | 0.171 | 6.478 | 0.414 |
| 40 | AA100540 | 0.196 | 7.180 | 0.365 |
| 41 | AI362368 | 0.199 | 6.967 | 0.397 |
| 42 | AI817134 | 0.167 | 6.592 | 0.362 |
| 43 | AI381377 | 0.193 | 6.179 | 0.401 |
| 44 | AI520967 | 0.188 | 6.534 | 0.386 |
| 45 | AA253470 | 0.182 | 7.002 | 0.365 |
| 46 | AI559304 | 0.195 | 7.408 | 0.369 |
| 47 | AI565002 | 0.182 | 7.149 | 0.381 |
| 48 | AI587389 | 0.197 | 7.006 | 0.355 |
| 49 | AI609367 | 0.206 | 6.648 | 0.354 |
| 50 | AI635278 | 0.200 | 6.629 | 0.427 |
| 51 | AI702056 | 0.208 | 6.370 | 0.391 |
| 52 | AI707917 | 0.177 | 6.392 | 0.414 |
| 53 | AI733176 | 0.209 | 6.211 | 0.411 |
| 54 | AI769053 | 0.210 | 7.570 | 0.383 |
| 55 | AI798545 | 0.167 | 7.289 | 0.394 |
| 56 | AI801425 | 0.174 | 6.780 | 0.406 |
| 57 | AI801595 | 0.188 | 7.061 | 0.409 |
| 58 | AI809873 | 0.200 | 7.207 | 0.413 |
| 59 | AI862063 | 0.173 | 7.001 | 0.347 |
| 60 | AI923251 | 0.197 | 7.085 | 0.359 |
| 61 | AI925556 | 0.178 | 6.924 | 0.329 |
| 62 | AI932551 | 0.177 | 7.191 | 0.415 |
| 63 | AI932884 | 0.182 | 7.430 | 0.409 |
| 64 | AI933797 | 0.204 | 6.834 | 0.423 |
| 65 | AI933967 | 0.193 | 7.007 | 0.443 |
| 66 | AI935874 | 0.203 | 7.166 | 0.388 |
| 67 | H06263 | 0.169 | 7.140 | 0.337 |
| 68 | H22921 | 0.241 | 6.445 | 0.408 |
| 69 | H54423 | 0.175 | 7.046 | 0.385 |
| 70 | N22551 | 0.205 | 6.830 | 0.387 |
| 71 | N73510 | 0.181 | 7.084 | 0.388 |
| 72 | R06107 | 0.164 | 7.067 | 0.352 |
| 73 | R42511 | 0.212 | 6.110 | 0.371 |
| 74 | R43088 | 0.215 | 6.067 | 0.398 |
| 75 | NM_181705 | 0.208 | 6.821 | 0.383 |
| 76 | R92455 | 0.203 | 6.629 | 0.410 |
| 77 | R93174 | 0.211 | 7.164 | 0.358 |
| 78 | T77995 | 0.201 | 7.251 | 0.423 |
| 79 | T79815 | 0.197 | 7.270 | 0.417 |
| 80 | T83946 | 0.196 | 7.388 | 0.363 |
| 81 | T95909 | 0.177 | 7.109 | 0.414 |
| 82 | T98779 | 0.186 | 6.964 | 0.416 |
| 83 | AK127462 | 0.198 | 6.784 | 0.367 |
| 84 | W80744 | 0.194 | 6.995 | 0.364 |
| 85 | W86575 | 0.236 | 6.761 | 0.438 |
| 86 | AJ297560 | 0.175 | 7.063 | 0.380 |
| 87 | NM_001562 | 0.192 | 7.021 | 0.516 |
| 88 | BU629240 | 0.214 | 6.696 | 0.401 |
| 89 | NM_001228 | 0.235 | 6.286 | 0.423 |
| 90 | NM_001993 | 0.192 | 6.874 | 0.451 |
| 91 | NM_002209 | 0.201 | 7.676 | 0.425 |
| 92 | NM_002392 | 0.197 | 6.969 | 0.431 |
| 93 | NM_000587 | 0.199 | 6.848 | 0.334 |
| 94 | NM_004379 | 0.222 | 7.135 | 0.415 |
| 95 | BC002715 | 0.182 | 6.685 | 0.502 |
| 96 | NM_003082 | 0.214 | 6.327 | 0.469 |
| 97 | AA664688 | 0.192 | 6.610 | 0.396 |

PRACTICAL EXAMPLE 2

Examination of Stability of the Reference Genes by Means of Gene Expression Examinations of Patients with and without Sepsis In this practical example we show that the reference genes determined in the first practical example are also stable in the cases of patients with and without sepsis under intensive-care treatment. To this end we considered microarray data of 118 patients. Altogether 394 patient days (microarrays) were analyzed, with a maximum of seven days being considered per patient.

TABLE 7

General data of the patients

| | |
|---|---|
| No. of patients (microarrays) | 118 (394) |
| Mortality | 31 (26.3%) |
| Sex [F/M] | 41/77 |
| Age in years [Median (IQR)] | 68.5 (14.8) |

TABLE 8

| Classification of the patient days according to ACCP/SCCM category, as well as additional diagnostic parameters | | | | | |
|---|---|---|---|---|---|
| | ITU Patients* | SIRS | Sepsis | Severe sepsis | Septic shock |
| No. of days | 33 | 158 | 24 | 90 | 89 |
| SOFA Score | 7 (3) | 7 (4) | 6 (3.25) | 8 (4) | 10 (3) |
| No. of ODFs | 2 (2) | 2 (1) | 1.5 (1) | 3 (2) | 3 (2) |
| PCT [ng/ml] | 1.6 (3.8) | 1.8 (5.4) | 1.2 (5.1) | 2.5 (4.9) | 6.4 (11.5) |
| CRP [mg/l] | 144 (53.9) | 112.5 (106.4) | 141 (87.1) | 133 (105.9) | 170 (146) |
| WBC [no/l] | 7750 (4075) | 11100 (7100) | 13350 (8800) | 12900 (6675) | 16100 (10600) |

*Patients under intensive medical care who did not develop SIRS or sepsis
The respective indications are the median and the Inter-Quartile Range (IQR) in parentheses.

In order to demonstrate the applicability of the reference genes by means of a comparison of SIRS and sepsis patients, the following test genes were selected (cf. Table 9).

TABLE 9

| Test genes for the comparison of SIRS and sepsis patients | | | |
|---|---|---|---|
| Name | GenBank Accession Nummer | Literature | SEQ ID NO: |
| CARD8 | NM_014959 | [7] | 98 |
| CCBP2 | NM_001296 | [8] | 99 |
| CCL26 | NM_006072 | [9] | 100 |
| FADD | NM_003824 | [10] | 101 |
| IL6R | NM_181359 | [11] | 102 |
| ITGB2 | NM_000211 | [12] | 103 |
| MAPK3 | NM_002746 | [13] | 104 |
| MYD88 | NM_002468 | [14] | 105 |
| TNF | NM_000594 | [15] | 106 |
| TREM1 | NM_018643 | [16] | 107 |

These test genes are described in the scientific literature in connection with sepsis.

For the statistical analysis, 6 patients with severe SIRS (SIRS+organ dysfunctions) and 9 patients with severe sepsis (sepsis+organ dysfunctions) were selected (Table 10).

TABLE 10

| Selected characteristics of the SIRS and sepsis patients | | |
|---|---|---|
| | Severe SIRS | Severe Sepsis |
| No. of patients | 6 | 9 |
| Mortality | 0 (0%) | 5 (55.6%) |
| Sex [M/F] | 4/2 | 7/2 |
| Age [years] | 70.5 (7) | 74 (7) |
| SOFA Score | 8 (2.25) | 10 (4) |
| No. of ODFs | 3.5 (1.75) | 3 (1) |
| PCT [ng/ml] | 3.1 (5.5) | 28.2 (38.8) |
| CRP [mg/l] | 71.2 (15.6) | 206 (180) |
| WBC [no/l] | 14250 (3800) | 15800 (4600) |

The respective indications are the median and the Inter-Quartile Range (IQR) in parentheses.

Normalization of the ten test genes was carried out by means of the following five, randomly selected reference genes. The method of Vandesompele et al. [6] was used (Table 11).

TABLE 11

| Selected reference genes (Set 1) | |
|---|---|
| GenBank Accession Nummer | SEQ ID NO: |
| AI263527 | 32 |
| AW964023 | 38 |
| AI933797 | 64 |
| T98779 | 82 |
| NM_004379 | 94 |

A comparison by means of the two sample t-test yields the following result (Table 12).

TABLE 12

| Gene activity of the test genes normalized with Set 1 of the reference genes | | | | |
|---|---|---|---|---|
| Gene symbol | SEQ ID NO: | Mean SIRS | Mean Sepsis | p-Value |
| CARD8 | 98 | 1.85 | 4.32 | 0.045 |
| CCBP2 | 99 | 1.25 | 2.69 | 0.004 |
| CCL26 | 100 | 1.52 | 2.69 | 0.041 |
| FADD | 101 | 1.26 | 3.45 | 0.028 |
| IL6R | 102 | 1.58 | 2.15 | 0.175 |
| ITGB2 | 103 | 1.04 | 2.60 | 0.074 |
| MAPK3 | 104 | 1.26 | 2.49 | 0.052 |
| MYD88 | 105 | 1.11 | 2.34 | 0.025 |
| TNF | 106 | 1.41 | 2.47 | 0.055 |
| TREM1 | 107 | 1.09 | 1.52 | 0.154 |

In order to demonstrate the repeatability of the results, the statistical comparison was repeated, with reference genes (Set 2) again being selected randomly (Table 13)

TABLE 13

| Reference genes (Set 2) | |
|---|---|
| GenBank Accession Nummer | SEQ ID NO: |
| AI609367 | 49 |
| AI862063 | 59 |
| H06263 | 67 |
| R92455 | 76 |
| BC002715 | 95 |

Following normalization by means of the method of Vandesompele et al., we obtain the following results for the two sample t-test (Table 14):

TABLE 14

| Gene activity of the test genes normalized with Set 2 of the reference genes | | | | |
|---|---|---|---|---|
| Gene symbol | SEQ ID NO: | Mean SIRS | Mean Sepsis | p-Value |
| CARD8 | 98 | 1.67 | 3.71 | 0.029 |
| CCBP2 | 99 | 1.15 | 2.35 | 0.001 |
| CCL26 | 100 | 1.37 | 2.34 | 0.033 |
| FADD | 101 | 1.15 | 2.98 | 0.015 |
| IL6R | 102 | 1.44 | 1.88 | 0.210 |
| ITGB2 | 103 | 0.97 | 2.27 | 0.050 |
| MAPK3 | 104 | 1.15 | 2.34 | 0.065 |
| MYD88 | 105 | 1.03 | 2.05 | 0.028 |
| TNF | 106 | 1.28 | 2.20 | 0.057 |
| TREM1 | 107 | 0.99 | 1.34 | 0.145 |

The results indicate very good repeatability of the results. In both comparisons identical markers at the 5% or 10% level, respectively, are significant.

PRACTICAL EXAMPLE 3

Determination of the Stability Values of Selected Reference Genes Through their Specific Primer by Means of Real-Time PCR RNA Isolation RNA was isolated from full blood with the aid of the PAXgene Kit (PreAnalytiX) in accordance with the manufacturer's specifications.

Quantitative Reverse Transcriptase-PCR (RT-PCR)

By means of reverse transcription, mRNA was rewritten to cDNA with the aid of an oligo-dT primer independently of its sequence. The cDNA strands formed in the process complementarily to the mRNA used were subsequently used as templates for various PCR reactions.

a) For the batch, the following components were pipetted together:

5 µg concentrated RNA

10 µl $H_2O$

1 µl dNTP (dGTP, dATP, dCTP, dTTP)

1 µl oligo dT (0.5 µg/µl)

b) 5 min at 70° C., subsequently 5 min on ice c) The following mix was added afterwards:

4 µl RT buffer

2 µl 0.1M DTT

1 µl RNase out (RNase inhibitor)

1 µl SuperScript reverse transcriptase d) incubate during 1 h at 42° C.

e) incubate during 15 min at 70° C.

Polymerase Chain Reaction

The selected DNA portion was amplified with the aid of the PCR and subsequently quantified, to thereby determine the strength of the gene expression of the reference genes:

For the PCR, the AccuPrime Taq DNA Polymerase System by invitrogen was used.

For a 25-µl batch, the following components are pipetted together into a 200-µl tube:

2.5 µl 10× AccuPrime PCR Buffer I

20 µl RNase free $H_2O$

1 µl Template DNA 1:10 diluted (approx. 0.82 ng/µl)

1 µl Primer mix (0.5 µl forward-/reverse-primer each, corresponding to Table 2)

0.5 µl AccuPrime Taq DNA polymerase

The following program is performed in the real-time PCR thermocycler (corbett research RG 3000):

| | |
|---|---|
| 94° C. 2 min | |
| 94° C. 30 sec | |
| 58° C. 30 sec | 30 cycles |
| 68° C. 1 min | |
| 68° C. 2 min | |

At first the template DNA was denaturated completely at 94° C. and the enzyme was activated. This was followed by 30 amplification cycles consisting of denaturation at 94° C., annealing at 58° C., and elongation at 68° C. Subsequent to the PCR, the samples were transferred onto a 1.5-% agarose gel in order to examine correctness of the products by way of fragment sizes.

TABLE 15

| Stability values of selected reference genes (RNA base) determined by specific primer and real-time PCR | | |
|---|---|---|
| SEQ ID NO: | GenBank Accession Number | Stability M |
| 87 | NM_001562 | 1.1028295 |
| 89 | NM_001228 | 1.0377301 |
| 90 | NM_001993 | 1.9214240 |
| 91 | NM_002209 | 1.1226082 |
| 93 | NM_000587 | 1.1679851 |
| 95 | BC002715 | 1.1285312 |
| 96 | NM_003082 | 0.9456845 |

REFERENCES

[1] Warrington J A, Nair A, Mahadevappa M, et al., Comparison of human adult and fetal expression and identification of 535 housekeeping/maintenance genes, Physiol Genomics. 2000 Apr. 27; 2(3):143-7

[2] U.S. Ser. No. 10/551,874, Method for recognising acute generalized inflammatory conditions (SIRS), Sepsis, Sepsis-like conditions and systemic infections

[3] O'Dwyer M J. Mankan A K, Stordeur P, The occurrence of severe sepsis and septic shock are related to distinct patterns of cytokine gene expression. Shock. 2006 December; 26(6):544-50.

[4] Bone R C, Balk R A, Cerra F B, et al. (1992) The ACCP/SCCM Consensus Conference Committee (1992) Definitions for Sepsis and organ failure and guidelines for the use of innovative therapies in Sepsis. Chest 101:1656-1662; and Crit Care Med 1992; 20: 864-874.

[5] Huber W, Heydebreck A, Sueltmann H, et al. (2003) Parameter estimation for the calibration and variance stabilization of microarray data. Stat. Appl. in Gen. and Mol. Biol. Vol. 2, Issue 1, Article 3

[6] Vandesompele J, De Prefer K, Pattyn F, et al., Accurate normalization of real-time quantitative RT-PCR data by geometric averaging of multiple internal control genes. Genome Biology 2002, 3(7):research0034.1-0034.11

[7] Razmara M, Srinivasula S M, Wang L, et al., CARD-8 protein, a new CARD family member that regulates caspase-1 activation and apoptosis. J Biol Chem. 2002 Apr. 19; 277(16):13952-8. Epub 2002 Jan. 30.

[8] Coelho A L, Hogaboam C M, Kunkel S L. Chemokines provide the sustained inflammatory bridge between innate and acquired immunity. Cytokine Growth Factor Rev. 2005 December; 16(6):553-60. Epub 2005 Jun. 20.

[9] Yamamoto T, Umegae S, Kitagawa T, Matsumoto K. Intraperitoneal cytokine productions and their relationship to peritoneal sepsis and systemic inflammatory markers in patients with inflammatory bowel disease. Dis Colon Rectum. 2005 May; 48(5):1005-15.

[10] Oberholzer C, Oberholzer A, Clare-Salzler M, Moldawer L L. Apoptosis in sepsis: a new target for therapeutic exploration. FASEB J. 2001 April; 15(6):879-92.

[11] Andrejko K. M., Chen J., and Deutschman C. S. Intrahepatic STAT-3 activation and acute phase gene expression predict outcome after CLP sepsis in the rat. Am J Physiol Gastrointest Liver Physiol 275: G1423-G1429, 1998.

[12] Piguet P. F., Vesin C., Rochat A. â2 Integrin modulates platelet caspase activation and life span in mice. European Journal of Cell Biology, Volume 80, Number 2, February 2001, pp. 171-177(7).

[13] Riedemann N C, Guo R F, Hollmann T J, et al., Regulatory role of C5a in LPS-induced IL-6 production by neutrophils during sepsis. FASEB J. 2004 February; 18(2): 370-2. Epub 2003 Dec. 19.

[14] Weighardt H, Kaiser-Moore S, Vabulas R M, et al., Cutting edge: myeloid differentiation factor 88 deficiency improves resistance against sepsis caused by polymicrobial infection. J. Immunol. 2002 Sep. 15; 169(6):2823-7.

[15] Hedberg C L, Adcock K, Martin J, et al., Tumor necrosis factor alpha—308 polymorphism associated with increased sepsis mortality in ventilated very low birth weight infants. Pediatr Infect Dis J. 2004 May; 23(5):424-8.

[16] Gibot S, Kolopp-Sarda M N, Bene M C, et al., A soluble form of the triggering receptor expressed on myeloid cells-1 modulates the inflammatory response in murine sepsis. J Exp Med. 2004 Dec. 6; 200(11):1419-26.

[17] Brazma A, Hingamp P, Quackenbush J et al., Minimum information about a microarray experiment (MIAME)—toward standards for microarray data, Nature Genetics 29, 365-371 (2001)

[18] Rocke D M, Durbin B, A model for measurement error for gene expression arrays, J Comput Biol. 2001; 8(6):557-69

[19] Huber W, Heydebreck A, Sueltmann H, Variance stabilization applied to microarray data calibration and to the quantification of differential expression, Bioinformatics. 2002; 18 Suppl 1:S96-104.

The invention claimed is:

1. A set of reference genes for the normalization of gene expression analysis data from blood samples of a patient, wherein the set of reference genes comprises the following RNA sequences: SEQ ID NO: 87, SEQ ID NO: 89, SEQ ID NO: 90, SEQ ID NO: 91, SEQ ID NO: 93, SEQ ID NO: 95, and SEQ ID NO: 96.

2. A set of primers derived from the set of reference genes according to claim 1, for the normalization of gene expression analysis data based on nucleic acid amplification, from blood samples of a patient, wherein the set of primers comprises the following DNA sequences: SEQ ID NO: 8 to SEQ ID NO: 21.

3. A set of probes derived from the set of reference genes according to claim 1, for the normalization of gene expression analysis data from blood samples of a patient, wherein the set of probes comprises the following DNA sequences: SEQ ID NO: 1 to SEQ ID NO: 7, and/or their complementary nucleic acid sequences.

4. A method for the normalization of gene expression analysis data with the aid of a set of control nucleic acids, comprising:

a) carrying out at least one gene expression analysis assay in vitro on a set of test nucleic acids in blood samples of a patient;

b) examining a set of control nucleic acids jointly in the same assay as a basis for the normalization of the gene expression analysis data of the samples to be examined, wherein the set of control nucleic acids is selected from the set of reference genes according to claim 1 the set of primers according to claim 2, or the set of probes according to claim 3, c) detecting signals from the gene expression analyses which reflect the degree of gene expression of a plurality of genes and of the set of control nucleic acids;

d) subjecting the signal data obtained in step c) to a mathematical transformation in order to at least weaken the technical variability of the signal data; and e) normalizing thereby the transformed signal data of the samples to be examined.

5. The method according to claim 4, wherein the mathematical transformation of the signal data is carried out by means of the arsinh or by means of a logarithmic approach.

6. The method according to claim 4, wherein the gene expression assay is selected from:

a) isolation of nucleic acids from a blood sample;

b) co-amplification of a set of control nucleic acids and of the nucleic acids to be tested; and c) probe hybridization.

7. The method according to claim 6, wherein the nucleic acids comprise mRNA or microRNA.

8. The method according to claim 4, wherein the nucleic acids are amplified by means of PCR, real-time PCR, NASBA, TMA, or SDA.

9. The method according to claim 6, wherein the expression values of the control and test nucleic acids are determined by means of hybridization methods.

10. The method according to claim 4, wherein the measurement of the expression values of the control and/or test nucleic acids takes place in solution or on nucleic acids immobilized on a support.

11. The method according to claim 10, wherein the support is a microarray, particle, bead, glass, metal, or membrane.

12. The method according to claim 10, wherein the control and/or test nucleic acids are indirectly coupled to the support through other binding partners.

13. The method according to claim 4, wherein the expression values of the control and test nucleic acids determined in vitro from a patient sample are used as input parameters for the production of software for the description of a patient's individual prognosis, for diagnostic purposes, for therapy decisions, and/or patient data management systems.

14. A method as in claim 4, wherein the method for normalization of Rene expression analysis data involves the diagnosis of disorders involving systemic immune reaction.

15. The method use according to claim 14, wherein the disorders are selected from: sepsis, severe sepsis, septic shock, or multiple organ failure.

16. The method use according to claim 14 in a method for in-vitro diagnosis of SIRS, sepsis, severe sepsis, septic shock, or multiple organ failure in an individual by using sets of control nucleic acids and test nucleic acids having an expression that is specific for SIRS or sepsis, comprising the following steps:

a) concurrent isolation of the control and test nucleic acids from a sample of the individual;

b) in a given case, amplification of the control and test nucleic acids;

c) determination of the expression values of the control and test nucleic acids;

d) a normalization of the gene expression of the test nucleic acids based on the expression values of the control nucleic acids; and e) determination whether the noraialized expression values of the test nucleic acid have reached a specific value for SIRS, sepsis, severe sepsis, septic shock, or multiple organ failure.

17. The method according to claim 12, wherein the binding partners are antibodies, antigens, oligonucleotides, molecular beacons, or enzymes.

* * * * *

SEQUENCE LISTING

```
<160> NUMBER OF SEQ ID NOS: 107

<210> SEQ ID NO 1
<211> LENGTH: 67
<212> TYPE: DNA
<213> ORGANISM: Homo sapiens

<400> SEQUENCE: 1

gagttagagg ccagcctggc gaaaccccat ctctactaaa aatacaaaat ccaggcgtgg     60

tggcaca                                                               67


<210> SEQ ID NO 2
<211> LENGTH: 69
<212> TYPE: DNA
<213> ORGANISM: Homo sapiens

<400> SEQUENCE: 2

ttataggtgt gagctactgt acccagcctt aacctgtttc acagttgatt atacttcatg     60

ctgttttcc                                                             69


<210> SEQ ID NO 3
<211> LENGTH: 69
<212> TYPE: DNA
<213> ORGANISM: Homo sapiens

<400> SEQUENCE: 3

ccacactacc acattaaaaa aattagaaag tagccacgta tggtggctca tgtctataat     60

cccagcact                                                             69


<210> SEQ ID NO 4
<211> LENGTH: 64
<212> TYPE: DNA
<213> ORGANISM: Homo sapiens

<400> SEQUENCE: 4

cccaaatgct gggattacag acatgaacca ccacgcctgg ctggaatact tactcttgtc     60

ggga                                                                  64
```

<210> SEQ ID NO 5
<211> LENGTH: 65
<212> TYPE: DNA
<213> ORGANISM: Homo sapiens

<400> SEQUENCE: 5
acgtagatag aggtggagac aggaaaaaga ctaagccaga cgtggtggct cacacctgta 60
atccc 65

<210> SEQ ID NO 6
<211> LENGTH: 70
<212> TYPE: DNA
<213> ORGANISM: Homo sapiens

<400> SEQUENCE: 6
gttcaaaacg aagactagct attaaaattt catgccgggc gcagtggctc acgcctgtaa 60
tcccagccct 70

<210> SEQ ID NO 7
<211> LENGTH: 70
<212> TYPE: DNA
<213> ORGANISM: Homo sapiens

<400> SEQUENCE: 7
cttggcctcc caaagtgcta gtattatggg cgtgaaccac catgcccagc cgaaaagctt 60
ttgaggggct 70

<210> SEQ ID NO 8
<211> LENGTH: 19
<212> TYPE: DNA
<213> ORGANISM: Homo sapiens

<400> SEQUENCE: 8
tgacagagcc agtgggaag 19

<210> SEQ ID NO 9
<211> LENGTH: 19
<212> TYPE: DNA
<213> ORGANISM: Homo sapiens

<400> SEQUENCE: 9
aggtgtgagc tactgtacc 19

<210> SEQ ID NO 10
<211> LENGTH: 20
<212> TYPE: DNA
<213> ORGANISM: Homo sapiens

<400> SEQUENCE: 10
gctaaattcc acactaccac 20

<210> SEQ ID NO 11
<211> LENGTH: 20
<212> TYPE: DNA
<213> ORGANISM: Homo sapiens

<400> SEQUENCE: 11
ccacgctcgt ctccaactcc 20

<210> SEQ ID NO 12
<211> LENGTH: 20
<212> TYPE: DNA

<213> ORGANISM: Homo sapiens

<400> SEQUENCE: 12
cactgtgcct gagctctgac 20

<210> SEQ ID NO 13
<211> LENGTH: 20
<212> TYPE: DNA
<213> ORGANISM: Homo sapiens

<400> SEQUENCE: 13
gatgaattgg gggatagatc 20

<210> SEQ ID NO 14
<211> LENGTH: 19
<212> TYPE: DNA
<213> ORGANISM: Homo sapiens

<400> SEQUENCE: 14
gagatggggt ttcaccatc 19

<210> SEQ ID NO 15
<211> LENGTH: 19
<212> TYPE: DNA
<213> ORGANISM: Homo sapiens

<400> SEQUENCE: 15
caattctcct acctcaacc 19

<210> SEQ ID NO 16
<211> LENGTH: 19
<212> TYPE: DNA
<213> ORGANISM: Homo sapiens

<400> SEQUENCE: 16
ggattacagg catgcaacc 19

<210> SEQ ID NO 17
<211> LENGTH: 20
<212> TYPE: DNA
<213> ORGANISM: Homo sapiens

<400> SEQUENCE: 17
ttgagtgcag cggtgtgaac 20

<210> SEQ ID NO 18
<211> LENGTH: 21
<212> TYPE: DNA
<213> ORGANISM: Homo sapiens

<400> SEQUENCE: 18
ccacagcata atgaattctg c 21

<210> SEQ ID NO 19
<211> LENGTH: 20
<212> TYPE: DNA
<213> ORGANISM: Homo sapiens

<400> SEQUENCE: 19
tgttggccag gctggtttcg 20

<210> SEQ ID NO 20
<211> LENGTH: 19
<212> TYPE: DNA

<213> ORGANISM: Homo sapiens

<400> SEQUENCE: 20
cctgacctct ggtgatctg 19

<210> SEQ ID NO 21
<211> LENGTH: 21
<212> TYPE: DNA
<213> ORGANISM: Homo sapiens

<400> SEQUENCE: 21
ttagaaaagt cctagaaatg c 21

<210> SEQ ID NO 22
<211> LENGTH: 2015
<212> TYPE: DNA
<213> ORGANISM: Homo sapiens

<400> SEQUENCE: 22
cccggaccga ggcaggacct caccccgcgc gtgttccccg ggcgcccctc tgcgaacccc 60
aggcccttcc caggtttgcg cgcgggggcc atccagaccc tgcggagagc gaggcccgga 120
gcgtcgccga ggtttgaggg cgccggagac cgagggcctg gcggccgaag gaaccgcccc 180
aagaagagcc tctggcccgg gggctgctgg aacatgtgcg gggggacaca gtttgtttga 240
cagttgccag actatgttta cgcttctggt tctactcagc caactgccca cagttaccct 300
ggggtttcct cattgcgcaa gaggtccaaa ggcttctaag catgcgggag aagaagtgtt 360
tacatcaaaa gaagaagcaa actttttcat acatagacgc cttctgtata atagatttga 420
tctggagctc ttcactcccg gcaacctaga aagagagtgc aatgaagaac tttgcaatta 480
tgaggaagcc agagagattt ttgtggatga agataaaacg attgcatttt ggcaggaata 540
ttcagctaaa ggaccaacca caaaatcaga tggcaacaga gagaaaatag atgttatggg 600
ccttctgact ggattaattg ctgctggagt atttttggtt atttttggat tacttggcta 660
ctatctttgt atcactaagt gtaataggct acaacatcca tgctcttcag ccgtctatga 720
aagggggagg cacactccct ccatcatttt cagaagacct gaggaggctg ccttgtctcc 780
attgccgcct tctgtggagg atgcaggatt accttcttat gaacaggcag tggcgctgac 840
cagaaaacac agtgtttcac caccaccacc atatcctggg cacacaaaag gatttagggt 900
atttaaaaaa tctatgtctc tcccatctca ctgactacct tgtcattttg gtataagaaa 960
tttgtgttat ttgataggcc gggcatggtg gctcatgcct gtaatcccag cactttggga 1020
ggccaggagt tcgagaccag cctggccaac atggtgaaac ccggtctcta ctaaaaattc 1080
aaaaattacc taggcgtcat ggggcatgcc tgtagtccca cctacttggg aggctgaagc 1140
aggagaattg ctcgaacctg ggaggcagag gttgcagtaa gctgagatca cgccactgca 1200
ttccagcctg ggcgacagag caagactcca tctcaaaaat aaaataaaaa aagaaagaaa 1260
gaaaagaaga agaaaagaga agaaggagaa ggagatgaag gaggaggagg aggagaagga 1320
gaagaagaag aagaagaaga ccacaaaaga catgactatc caacttttta tgacaaactg 1380
caaggaataa aggaagaata agtccatgta ctgtaccaca gaagttctgt ctgcatcttg 1440
gacctgaact tgatcattat cagcttgata agagactttt tgactctata tccttgcagt 1500
taagaagaaa gcactttttt gtaatgtttg ttttaatggt tcaaaaaaaa tctttcttat 1560
aaagagcata ggtagaatta gtgaactctt tggatccttt gtacagataa aggttataga 1620
tttcttgtgt tgaatattaa aaaagcaagg atgtctaacc attaagatta tccaaagtca 1680

```
ggctgggcgc agtggctcac gcctgtaatc ccagcacttt gggagggata ggtgggcgga   1740

tcacctgagg tcaggagttt gagaccagcc tggccaacat ggcaaaaccc cgtctctaca   1800

aaaatacaaa agaaattagc cagacatgat ggcgggtgcc tctaatccca gctactgggg   1860

aggctgaggt gggagaatcg cttgaactcg ggaggtggag gttgtagtga ggcgagattg   1920

tgccattgca ctccaacctg ggcgacagag tgagactcca tctcaaaaaa aaaaaaaaaa   1980

aaaaaaaaaa aaaaaaaaaa aaaaaaaaaa aaaaa                              2015


<210> SEQ ID NO 23
<211> LENGTH: 356
<212> TYPE: DNA
<213> ORGANISM: Homo sapiens

<400> SEQUENCE: 23

gttttgtttg ttttgttttt ttttttaata ttttttaaga gctgtaaaga aggagaagag     60

gaatgagaaa atgagaaaga attattatta ttattggtgg tagtagtgat agagactgta    120

tgtggcctat aaaggctaac atattcactg tctgaccctt tagagaaagt ttgtcaaccc    180

ctggcctaga acatgggtgg cttcttacta gggctcagta agtgtctgaa tgaaggaagg    240

aacagtttaa aactcagctt tgccgggcgc agtggctcac gcctgcaatc ccagcaccct    300

gggaggccga ggcgggcgga tcatgaggtc aggagttcga gaccagcccg gccaac        356


<210> SEQ ID NO 24
<211> LENGTH: 451
<212> TYPE: DNA
<213> ORGANISM: Homo sapiens
<220> FEATURE:
<221> NAME/KEY: misc_feature
<222> LOCATION: (451)..(451)
<223> OTHER INFORMATION: n is a, c, g or t.

<400> SEQUENCE: 24

aatggagacg agttcttact atgttgccca ggcaagtctc aaactcctgg gttcaagcga     60

ctctcccacc tcactctccc aaagtgttgg gattacaggc gtgaggcact gcacctggcc    120

taatccacaa actgtctaga agcaaacaac caaacatatc gagaattttt ctgagtgtaa    180

aaataaatct ctttgtggca tgattctatt acagatcact ggtatgcctg attaaagtgg    240

actacaataa agattacata caccagactt taaataattg caatccactg aaataacagc    300

atttactaat ctcagcgaat gctcaattta ttgagcattt acacctgacc aaatgtctta    360

attcaacctt ttactcaatc ctgaatcatc tgtataaatt ggaaataaca gttgtcatac    420

aaactttaag taattccttc actgggtacc n                                   451


<210> SEQ ID NO 25
<211> LENGTH: 397
<212> TYPE: DNA
<213> ORGANISM: Homo sapiens

<400> SEQUENCE: 25

tttttttttt tttttgagac gtagtctttc tctgtcacct aggttgaagt gcagtggtgc     60

aatcttggct cactgcaacc tccacctccc aggttgaagc gattctcctg cctcagcctc    120

ctgagtagct gggattacag gcatgcacca tcacacctga ctttgtattt ttagtagaga    180

cggggtttcg ccatgttgcc aggctggtct caaactcctg agctcagcca atctgcccgc    240

cttggcctcc caaaatgctg ggattacagg cgtgacacta gtgcctggcc tggtctttca    300

gtaccatata caagcctgca ataaatctgt ttagacataa tgtcatagaa gtgagtgtat    360
```

ctgtgggaca aatccctaga attgctgggt caaaggg 397

<210> SEQ ID NO 26
<211> LENGTH: 457
<212> TYPE: DNA
<213> ORGANISM: Homo sapiens

<400> SEQUENCE: 26
tgaccaggat ctcactcagt cactcaggct agagtgcagt ggcatgatca tggctcacca 60
cagacttgac ctcccagact caggtgattc tcccacctca gcctcccgag tagctacgac 120
tacaggcgtg cgccaccacg cctggactaa tttttccata gaaacggggt tttaccatgt 180
tgccccaggc tggtctcgaa ctcttgtgct taagagatcc tcctgcctca cactcccaaa 240
gtgctgggat tacaggtgtg agccacggtg cctggcctat actatctctt tcaactctct 300
caataactta caaatgaaga aactagggct tacagaggtt aagggttaag taggggcaca 360
tggtaggaaa tcagaattct aacctacatc tatgcaaccc cgacatctgt gctccttcca 420
ttccattaaa aacatgtagg ctgcaaaaaa ccacagg 457

<210> SEQ ID NO 27
<211> LENGTH: 2811
<212> TYPE: DNA
<213> ORGANISM: Homo sapiens

<400> SEQUENCE: 27
acaaggcagg atgtgtgcgt gggaggaaga ttgacagtga ctgagcctgg acgggggaga 60
ccaggtatga ggtctgaagc acctggaaca gaaaggacag gacagatgtg ggcacactgc 120
acgtgtagaa tcaaaggact gacagcaggt cgaatgtgag gaatgaggga gggaaagaat 180
caggactcaa gtgccatcct ggctgcctca aaaaatgata ctgtcttcca gagggaaagg 240
aaagataaca atagttactg ctttgtggcg tacatgtgat gaatttcatt ttggacattc 300
cagtaggata tccaagtgga aatgcccagt aagccttaga cataaggatc tggatctcaa 360
gagaaaaatt gaggttgaac cataatatgt ctttcccctc gaatcatgta ggtttctctt 420
ttgccttctt tcattggcct aagtggtcct aaatgctact gctgatgctg tcttagtttg 480
cgactgttgt ttgcacccca ccttttccca aaggtaatct gtagacttgc atggattggg 540
ttaaggtggt taacctgcag ctttgctgtt caaagcttgg cttcccacta ccagtttgcc 600
aacttaatga gtacttcaac ttgagtcaaa ttagtattgt tccaaatatc ctaatagtat 660
cctctatgtg tgactctagg tcttacaaaa tcaaggtgtc ctttctcatt gagacttcct 720
tattaataaa atatttcttc tattaaattc aacctggcac caagcatagt aggtaatagg 780
cacacacaat gactgtttat tgaatgaatg aataaaatga ttatgttagg gcattctgag 840
caattcatcc taagcagcta attttctcct acttctttta ttatagtgtg tgtttgtgtg 900
tgtgtgtgtg tgtgtctgaa atgtcccatc ctacaggttc attaatattt aatagaaatg 960
aaagaagaaa aatacctatt aagtgttttg atttcatcct tttcattgaa ttgaaaaagt 1020
atatcattta ttcctgaaga gaaatctaga ttttgctcta tattaaacat ttgacattta 1080
ttggtcctta atgctaatat agataccagc ctgctggttg tcacattcta tctgtttata 1140
cgaaggttgt agacacacag cgtatgtaca tatgcctagt tgctctcatt ccttttgttt 1200
cacatctcaa gcctaaccca gactgaaaag gttttgaagg ctgagattat tcatcacccc 1260
atcattatag aaagcagggc tggcccaagg ttctcacagt gggagcaagg tggattttaa 1320
ctctgatcag tgttgtagct caaatataaa aagaactgca gcacaaaagt cacaaggata 1380

```
aatgatcccc tcgttcttct cccataaaaa taagcagcca attgaaggtg gaagtcagta   1440

cagtgcggca ttcccagagg cgacagaacc taagattcca tttctaaaga cactgctcaa   1500

caagaagacc acctgggatg tcttacataa aaccattggc ctggcagctt ttggctgagt   1560

tctctattct ggttcaagcc agcatcacag cctatctgtg gttttaacaa ctgatggaat   1620

ttgtattttg agaaccctca tccgttagca tgaagcaaac tcaaagcatt gttgctcatc   1680

agttgtcatc tgtttgagaa agattttgat ttgtttactt gtagtgaagc ttgaccatac   1740

ttctccaggg gctttttaaa aagatgaatg tgtcagcttg tagatttgtc cccatgaatg   1800

aaaccacaag caaattctct tctctcttcc agcctccctt cctccctctt gtttcttcag   1860

tggccatctg tgcattatgt tcccattgcc aggccctctt caagcagctt atctatgagt   1920

gaattcagaa acttcaaatt ataaaggaca cccagataat tggcctgttc tccaaagtat   1980

ctgtcccctg tgctgctgcc agattccttc ttaatgaata catccagtga cagtgggatt   2040

cttgagcttg tccgtatctg tgagaaaatg agctctcctg ctttgtaaca gcttgtggct   2100

cagggaaaaa aatgacagcc attgcacaag tttcctttga atgtagtttt ctttcccata   2160

aatgatactt tgagaataca gttaaggggt tattagtttt ctatttcatg cctggcctgt   2220

gtgtgagaat aacacaagct gtcactgcaa atcagtagct aaaaatgctt tgtctggtta   2280

atgtgaacat ttaatatttg gctcaattaa aaattaaccg atgaaagtac atgtcattgg   2340

aatttgaaaa taccttttgt acggaatact taaagggcat cacccatgac taaaccagtg   2400

cttttaaaat atggagaata tggggaaatt taatatgagt tgggatactt gactcttttt   2460

taaaacctct ctacctgttt ggcacaacag ggtattgata aagagtgggc tcattgttat   2520

ggcaaaggat tcacttgcat ctctgtgttt ttaagtgggt aattgttttt ttgcactcag   2580

tcacatgatt aaagcagaca gaacaagaga tcagttattc atttatacca tacttttaaa   2640

aaaatattga gccaggccct ggggaagtgg gaagtgagag ccagagcggc gtggctgata   2700

gtctagggca gtgctatcca atcttttggc ttccctgggc cacattggaa gaagaagaat   2760

tgtcttgggc cacacgtaaa atacgctaac acgaatgata gctgatgagc t            2811
```

<210> SEQ ID NO 28
<211> LENGTH: 394
<212> TYPE: DNA
<213> ORGANISM: Homo sapiens

<400> SEQUENCE: 28

```
tttttggag acggagtcgt ccccgtcacc caagctggaa cgcatggtgt ggatctcggc     60

tcactgcaaa ctctgcctcc caggtttaag tgattctcct gccccagcct cccaagtagc    120

tgggattaca gaagcgcgcc actacaccca gctaattttt gtatttttag tagagacagg    180

gtttcagtat gttggtcagg ctggtctcga actcttgacc tagtgatcca cccgcctcgg    240

cctcccaaag tgctgggatt acaggcgtgc gactgcgtcc ggcctgattc acatatattt    300

taagagacta aacataggaa agctaggaga tcttgtgtgg tggcaggttt cttctgccac    360

tcaggggtag gacactgggg cagggggagt ggcc                                394
```

<210> SEQ ID NO 29
<211> LENGTH: 497
<212> TYPE: DNA
<213> ORGANISM: Homo sapiens

<400> SEQUENCE: 29

```
gcacgagaag agtctcattc caggaaccct ttgtagttag ttggctggca tgtttacttg     60
```

```
ctgctgtagc cagccaagat gagtgcacct aggccctcaa aaaggatttt tttttacctc    120

aatctagcct gaccctcata tctgtggttg cctctgagac gaacatccat gctagtataa    180

aaatagttag gaatgccctt ggcagaactg aagctcttat taaatggtgg acagagctct    240

tgccagcttt gatccagccc ctcagtctcg gagttatggg gcagggttgg ggggcagtgc    300

tacactgtaa agaatttcca ggctgggcgc ggtggctcat gcctgtaatc ccagcacttt    360

gggaggccga ggagggcgga tcacaaggtc aagagattga gatcatcctg gccaacatgg    420

tgaaactccg tctctactaa aaatacaaaa attagctggg catggtggca cgtgcctgta    480

gtcccagcta cttggga                                                    497
```

<210> SEQ ID NO 30
<211> LENGTH: 206
<212> TYPE: DNA
<213> ORGANISM: Homo sapiens

<400> SEQUENCE: 30

```
tgagacagtg tcttactcag ttgggactac aagtgtgtgc caccatgccc ggctatctta     60

tctacctatc gacctgagac agggtctccc cttctgttgc ctgggctgga gtgcaccggt    120

gtgatctcgg ctccctatag cctccacctc ttgggcccaa gtgatcctcc aacctcagtc    180

tcacgagtag ctgggattac agctgc                                         206
```

<210> SEQ ID NO 31
<211> LENGTH: 376
<212> TYPE: DNA
<213> ORGANISM: Homo sapiens

<400> SEQUENCE: 31

```
tttttttttt taagtgtcag tgttcataaa ggcccttttt ctttttcaag gatgggtata     60

aagtgttact cggccgaacg cggtggctca cacctgtaat tccaacactt tgggattaca    120

ggcgtgagcg accgcgccca gccgaacttc tgcctcttaa atccagggtt ctccctgtca    180

gtacagtgag gtggtaacta gcaaaagcta tgagatatga ctgcctgggt acatatccca    240

gctctttcac ttatctttgt ggctttacgc aaattactta acctctttat gattgtttct    300

tcatttgtaa aaggaagata ataacagtgc ctatatatag ggtttttatg aagaataaat    360

gagatagtat atataa                                                    376
```

<210> SEQ ID NO 32
<211> LENGTH: 337
<212> TYPE: DNA
<213> ORGANISM: Homo sapiens

<400> SEQUENCE: 32

```
tttttttttt ttttattttt agacaaagtc ttgctctatt gcccaggctg tagtgcagtg     60

gcacaatcat agctcactat aaccctcgac ctcccgggct caagcaatcc tcccacctca    120

gcctcccgaa tagctgggac tacaggcatg caccaccaag cctggctaat ttgctatttt    180

tgtttttcat agagacagag tctggccatg ttgcttaggc aggtttcgaa ttccttgcct    240

cagcctctca aggaatttgc attgttttta atgaaaaaac acacatatgg tgaacagtaa    300

aagtgggaga attgaacagc cctaaaatca agtagtc                             337
```

<210> SEQ ID NO 33
<211> LENGTH: 381
<212> TYPE: DNA
<213> ORGANISM: Homo sapiens

<400> SEQUENCE: 33

```
aagatggagt cttactctgt cgcccagact ggagtggtgc gatctcggct cactgcaacc     60
tccaactcct gggttcaagc aattctcctg cctcagcttt ccaagtagct gggactacag    120
gtgtgcgccg ccacacccag ctaatttttg tattttttag tagagacagg gcttcactat    180
atgttggcaa gactggtctc gaacccctga cctcaggtaa tctgcctgcc ttggcttccc    240
taagtgctgg gattacagtt gtgagccacc acgcccagcc agcactacct tttctattgt    300
gcatcctaat ggtctgtagt atagacatat ttatagggga aagaaaggaa tagatgtggg    360
caaaaagaag ctaaaaaaca t                                              381
```

<210> SEQ ID NO 34
<211> LENGTH: 494
<212> TYPE: DNA
<213> ORGANISM: Homo sapiens

<400> SEQUENCE: 34

```
ttatttggct aaattattga tcctacttca gagggaaagt gtaccaggca gttttggtgg     60
gtggtgctga agtctgggga gtgagtttag tcttcagact attcttggcg acatcaccag    120
tgttgcaagc accaccattc ccagttaggc actttttgtc cctggtaaga cttgaccttt    180
atctggaaca ctccttttgt ccctagagtg gggacctaag gctcagcaaa agggcagaat    240
caggaaagcc tttatggtgt ggctaaagga gtggccagag ccttgggact cctttgctgc    300
cttctccctg gttccagttg tctttagatt ttcacggctc ttactgctgt tacttaacag    360
tattttccag ccaggcatgg tggttcacgc ctctggtccc tgcactttgg gaggccgagg    420
caggcggatc acctgggatt gggagttcgg gaccagcctg tccaacatgg cgaacctcgt    480
ctcttctgag agta                                                      494
```

<210> SEQ ID NO 35
<211> LENGTH: 521
<212> TYPE: DNA
<213> ORGANISM: Homo sapiens

<400> SEQUENCE: 35

```
tttttttttt tttttacttg ataatagatt aagatttatt tattcagtaa gcgataacaa     60
ttttgaattt ttatgcctaa tggtattaac ttaaaataat aatacaagca atattgagaa    120
atctataaga aataacagac aaatctataa tcatagaagg aaatttcagc cactgctaga    180
taaggtagac acaaaagtca gtaaggttgc aaaaggtgag cagaatgatt aaaaatttaa    240
caagttggca gggcacagtg gctcatgcat gtaatcccag cactttagga ggccgaggca    300
ggctgatcac gaggtcagga gttcaagacc agcctggcca acatggtaaa accccatctc    360
tactaaaaat acaaaaatta tccgggtgta gtggtgcatg cctgtaatcc cagctactcg    420
ggaggctgag gcaggagaat tgcttgaatc caggagggag agattgtggt gagccaagat    480
tgcctcactg cactccagcc tggggaacag agaaaggccc t                        521
```

<210> SEQ ID NO 36
<211> LENGTH: 351
<212> TYPE: DNA
<213> ORGANISM: Homo sapiens

<400> SEQUENCE: 36

```
tttggtctct ctttttatat ttattaactt ttgtagtaaa taagtataat tttataaatt     60
gtctgaacag aatgggcatg gtggctcatg cctgtaatgc caacacatcc agccttgtat    120
```

```
gtgttcttga ccggcatata ttgttagtgt gcatgtattt taactgatat aaatgataag    180

ttccctattg ctatgtgaac atataatcca ttactttgaa tcactacaca ttttcacatt    240

ttacttacct tccccataca gacttccaat tcctgccccc aacaattaat attgtgacca    300

gcatccatac tgtgcctctt gcggtcctct gtgagagctt cctgagagac g             351


<210> SEQ ID NO 37
<211> LENGTH: 451
<212> TYPE: DNA
<213> ORGANISM: Homo sapiens

<400> SEQUENCE: 37

tttttgagac acagtcttgc tctgtcaccc gggctggaat acagtggtac aatcttggcc     60

tccacctccc aagttcaagc aattctcctg cctcagcctc ccaagtagct aggattacag    120

gcacccacca ccacgcccgg ttaacttttg gttttaagac ggtgtcttgc tctgttgccc    180

aggctagggt gcaatggtgc catcttggct caccgcaacc tccacctcat gggttcaagc    240

aattctcctg cctcagcctc ccgagtagct gggattacaa gcgcacccca ccacacccgg    300

ctaatttttg tatttttagt agagacggag tttcaccatg ttggccaggc tggtctggaa    360

ctcctgacct caagtgatcc gcccgcctcg gcctcccaag gtgctaggat tacaggcgtg    420

agccaccgct cccagccgca ccgttttttt c                                   451


<210> SEQ ID NO 38
<211> LENGTH: 674
<212> TYPE: DNA
<213> ORGANISM: Homo sapiens
<220> FEATURE:
<221> NAME/KEY: misc_feature
<222> LOCATION: (552)..(552)
<223> OTHER INFORMATION: n is a, c, g or t.
<220> FEATURE:
<221> NAME/KEY: misc_feature
<222> LOCATION: (556)..(556)
<223> OTHER INFORMATION: n is a, c, g or t.

<400> SEQUENCE: 38

ttatttggtg ttaaacaggt ttaatgacgg tcatggcaac tttttggcac aatgaaaaat     60

atcgcccatg atcaacgtgt tctgttctgg ggaagggggc aaaggcaggg tgaatcactt    120

tcttaaaaag tatagctcaa gttgggagtg cagagggaat ggggagaaaa cccttccgct    180

gcctgtgtcg aagtgcagga gcccccaccc ccatactcac ctgagtccag cccctctggg    240

gaaagaaggg gtgcatgaac tccccttagt ccacaggcgc ctccctgtgg cccaaggccc    300

tcttcacact ccatcttgta gccccagcag gagctatttt ccgaaaagtg ctgggattac    360

aggcgtgagc cactgtgccc agctgagatc tgatggtttt aaaaagagga gctcccctgc    420

atgagatctc actttttgcc tgctaccatt tatgtaagat gtgacttgct ccttcttgcc    480

ttccatcatg actgtgaagc ttcccccacc atatggaatt gtaagttcaa ttaaacttct    540

tttctttgga anttcnaaag ccctcccttt acacttgcaa agggtcccaa aatacttcct    600

tgaggggggg gccccgtacc ccaattcgcc ctttggtgga gtcgttttaa caattccctg    660

gcccgccgtt ttaa                                                      674


<210> SEQ ID NO 39
<211> LENGTH: 330
<212> TYPE: DNA
<213> ORGANISM: Homo sapiens

<400> SEQUENCE: 39
```

-continued

```
tttttttaga aagaagtggg gtctcacatg ctgtccaggc tagtctcaaa ctcctgggct     60

caagccatcc tctcacctcg gcctcccaaa gtgctgggat tcaggcatga gccaccactc    120

ccggccctca attaataact tgacttaaga taatctagtt catattaact taatttcata    180

gcatacaaaa actatgcttc atttcttcct tccattattc tatcatgaat atggcacctt    240

tttgtgttat aagcccattg acacagttta taattattgc ttatgcaggt gggtgtcttt    300

taaatcagag ataagagaat aaaatatcta                                     330


<210> SEQ ID NO 40
<211> LENGTH: 446
<212> TYPE: DNA
<213> ORGANISM: Homo sapiens
<220> FEATURE:
<221> NAME/KEY: misc_feature
<222> LOCATION: (446)..(446)
<223> OTHER INFORMATION: n is a, c, g or t.

<400> SEQUENCE: 40

ccagtttgta tttatttatt tatttattta tttagagaca gagtctcgct ctgtcgccta     60

ggggggtgca gtggcgcaat ctcagctcac tgcaacctcc acctcccggg ttcaagcgat    120

tctcctgcct cagcctcctg agtagctggg attacaggcg tgtgccacca tgcccagcta    180

atttttgta ttttagtag agacagggtt tcaccgtgtt agccagggtg gtcttgatct      240

cctgacctca tgatccgtcc gcctcagcct cccagagtgc tgggattaca ggcatgagcc    300

actgcgcctg gcccaattta tttttttttg tagtttcatt ctcctcacat ccaaacagct    360

acagctttcc ctccttttgt ggggtcccca aaccaagtct cttttcagga gagcagacat    420

gtgcctccac acagttctga agttcn                                         446


<210> SEQ ID NO 41
<211> LENGTH: 406
<212> TYPE: DNA
<213> ORGANISM: Homo sapiens

<400> SEQUENCE: 41

tttttctga gacggagtct tgctctgtcc cccaggccgg agtgcagtgg cgccatctca      60

tctcactgca agctccgcct cccgggttca cgcccttctc ctgcctcagc ctcccgagtt    120

gctgggacta caggcgcccg ccaccacgcc cggctaattt ttgtattttt agtagagaag    180

ggtttcacc gtgttagcca taatggtctc gatctcctga cctcatgatc cacccgtctc     240

agcctcccaa agtgctagga ttacaggcgt gagccagcgc gcccggccta ccctccctat    300

tttcaaaaac attgtggcaa tggacaaaat tcacatgtac aaccgatcat tacaatcaga    360

cgctctgtga tacgtgtacc aacgacaagg gctgaaataa tgactg                   406


<210> SEQ ID NO 42
<211> LENGTH: 320
<212> TYPE: DNA
<213> ORGANISM: Homo sapiens

<400> SEQUENCE: 42

cacacccagc taactttttg tattttttgt agacagggtt tcaccttatt tctcaggctg     60

gtcttcaact tctgggctca agcaatccac ccgcctcagt cacccaaaat gctaggatta    120

caggcgtgag ccattgcgcc cagcctcaaa actcttctac ctaaaatcac cttcagagcc    180

atgctagaaa attagtatca ttcctttaca atcggaatcc aacttggcca ctaaaatgtt    240

tccttagact tggtcctaaa tgatttttgg attgtttcaa aacctgaaaa acaccttcac    300
```

```
aggataaaga taaaagaatg                                                320


<210> SEQ ID NO 43
<211> LENGTH: 448
<212> TYPE: DNA
<213> ORGANISM: Homo sapiens
<220> FEATURE:
<221> NAME/KEY: misc_feature
<222> LOCATION: (167)..(167)
<223> OTHER INFORMATION: n is a, c, g or t.
<220> FEATURE:
<221> NAME/KEY: misc_feature
<222> LOCATION: (181)..(182)
<223> OTHER INFORMATION: n is a, c, g or t.
<220> FEATURE:
<221> NAME/KEY: misc_feature
<222> LOCATION: (219)..(219)
<223> OTHER INFORMATION: n is a, c, g or t.
<220> FEATURE:
<221> NAME/KEY: misc_feature
<222> LOCATION: (299)..(299)
<223> OTHER INFORMATION: n is a, c, g or t.
<220> FEATURE:
<221> NAME/KEY: misc_feature
<222> LOCATION: (346)..(346)
<223> OTHER INFORMATION: n is a, c, g or t.
<220> FEATURE:
<221> NAME/KEY: misc_feature
<222> LOCATION: (401)..(403)
<223> OTHER INFORMATION: n is a, c, g or t.
<220> FEATURE:
<221> NAME/KEY: misc_feature
<222> LOCATION: (420)..(420)
<223> OTHER INFORMATION: n is a, c, g or t.
<220> FEATURE:
<221> NAME/KEY: misc_feature
<222> LOCATION: (428)..(433)
<223> OTHER INFORMATION: n is a, c, g or t.
<220> FEATURE:
<221> NAME/KEY: misc_feature
<222> LOCATION: (442)..(442)
<223> OTHER INFORMATION: n is a, c, g or t.
<220> FEATURE:
<221> NAME/KEY: misc_feature
<222> LOCATION: (445)..(445)
<223> OTHER INFORMATION: n is a, c, g or t.

<400> SEQUENCE: 43

tttcttttag acagggtctc actctgttgc ccagactgga atgcagtggt gcagtcttgg     60

ctcactgcag cctcaacgtc ttgggctcaa gcgatcctcc catctcagcc tttcaagtac    120

ttgggactac aggcatgctc caccacatcc agctaatttt tgtattntgc gtaaagatgg    180

nngttttgcc atgctgcttc tcgaactcct ggagggggnc aagtaattct gtccacctca    240

acctacaaaa gtgccggaac tataagcatg agccactgac ccagcttgaa atggtaatnt    300

aataaaatat atcatttatt tttcaaagac tagatctacc catganccac agatctgaat    360

attttaaatt gtcttccctg gtacatcatt gccattacct nnnaatggta cactctacan    420

tatgctannn nnnggtgcat anaangaa                                       448


<210> SEQ ID NO 44
<211> LENGTH: 270
<212> TYPE: DNA
<213> ORGANISM: Homo sapiens

<400> SEQUENCE: 44

ttttttttt tttttgctca cagaatgtat acgtttattt tttaacggag ttaattcatg      60

gccgggtgtt gtggctccca cctgtaatcc cagcactttg ggaggctgag gcgggtggat    120

cacctgaggt caggagttca agatcagcct ggccaaaatg gtgaaacctc atctctacta    180
```

aaaatacaaa aattagccag gtgtgatggc atgtacctat aatcccagct actcaggagg 240
ctgagacagg agaatcgctt gaatctggga 270

<210> SEQ ID NO 45
<211> LENGTH: 386
<212> TYPE: DNA
<213> ORGANISM: Homo sapiens

<400> SEQUENCE: 45
taaaataata gaggcatagt ctctctatgt caggctggtc tcaaaactcc tggcctcaag 60
caatcctccc acctcagcct cccaaagtgc tgggattaca ggcatgagcc actgtgccta 120
gccaacatgg gacatttcta actcgagggt attgtcaggc catgtaggaa agggagcaga 180 gattgcccctt gaggagatgc tcccaggtgg cagatttgtc ctacttgata gattccaaaa 240
tggaaaacgg atttttctgc tgcctctggg gacactgaaa aaagaacctc cacatgagtt 300
cagaggcagc accggcagct taggggaagt catggcttcc actgcgtgtc taggaagcgc 360
tctttcagga tgctctgagg ctgcca 386

<210> SEQ ID NO 46
<211> LENGTH: 413
<212> TYPE: DNA
<213> ORGANISM: Homo sapiens

<400> SEQUENCE: 46
tggtgagaca gagatttact cttgttgccc aggctggagt gcaatggcat gatctcagct 60
caccgcatcc tccacatcct ccgcctccca ggttcaagtg attctcctgc ctcagcctcc 120
tgagtatctg ggattacagg catgtgccac cacgcccggc taattttgta ctttttttagt 180 agagacgggg tttcatagtg ttgcctaggc tgatctcaaa ctcctgacct caggtgatct 240
gcccgcctct gcctcccaaa gtactgggat tacaggcgtg agccactgcg cccggcctac 300
cagaactaat ttttaatcaa atttcataaa taaatctagc caatcttagc tggttcatta 360
aggaccagca aaatcatctg ttgggacttg ttagtggagc tctcctagat agt 413

<210> SEQ ID NO 47
<211> LENGTH: 438
<212> TYPE: DNA
<213> ORGANISM: Homo sapiens

<400> SEQUENCE: 47
ttcttttctc cttttttttt tttctttttt tgagtcagag tctgtcgccc agcctggagg 60
gcagtggtgg gatcttggct cactgcaatc tctgccttcc aggctcaagc aattctcctg 120
cctcagcctc ctgagtagct gggactacag gcctgcacta ccacacctgg ctaacttttg 180
tatttttagg agacagggtt tcaccatgtt ggccaggctg gtctcgaact cctggcttca 240
agtgattcgc ctgcctccca aagtgatggg attacaggcg tgagccactg tgcccggcca 300
gggttttttt ttcctgaagg gctgatcatg gctttgttcc actcactgtg cccttcttcc 360
tctgcttgga actggacaga agttccaata agctactgtc ttctattaag taaggaccag 420
acatgaaaaa ctttatgg 438

<210> SEQ ID NO 48
<211> LENGTH: 651
<212> TYPE: DNA
<213> ORGANISM: Homo sapiens
<220> FEATURE:
<221> NAME/KEY: misc_feature
<222> LOCATION: (448)..(448)

<223> OTHER INFORMATION: n is a, c, g or t.
<220> FEATURE:
<221> NAME/KEY: misc_feature
<222> LOCATION: (590)..(590)
<223> OTHER INFORMATION: n is a, c, g or t.

<400> SEQUENCE: 48

```
tccatttgaa agacactcat ttatttgtta ataacacaag ccaaacaaaa acatatctgg     60

ggatgaatct gcgaaaccta ctagggttaa aattttactt ctcttaattg tttggcttcc    120

aaaacatatt tggcttccaa aacagattca aattcaaaaa atatttacgg ccagctgtgg    180

tggctcatgc ctgtaatccc agcactttgg gaggccaagg tgggcggatc acgaggtcag    240

gagatggaga ccattctagc caacatggtg aaaccccgtc tctactaaaa atgcaaaaat    300

tatctgggta tggtggtacg tgcctggagt cccagctact tcggaggctg aggctggaga    360

atcactttca cctggaaggg cgaggttgca gtgagctgag atttgccact gcactccaac    420

ttggtgacag agtgagactc tgtctcanaa aaatggaata attaaataaa aaataattgt    480

tcagagtgcc actagggaga ggtatattca ttagaatgga caatgccttt taatggtatg    540

gttgccggtg gctggctcac gcctgatccc acaactttgg agggcgaggn gggcgaacaa    600

gaggtcaggt cgaaccagcc tgacccaaat gtgaaacctg cttactaaaa a             651
```

<210> SEQ ID NO 49
<211> LENGTH: 428
<212> TYPE: DNA
<213> ORGANISM: Homo sapiens

<400> SEQUENCE: 49

```
ccactgttgc tgagacattt ttattggcat aggttatatg tttgtgtgtg tgtgtgtgtg     60

tgtccctaaa caatatttag caagttgact gtttttaaac tttatatcaa tggtgtatat    120

taaatatgat cgtctacagt ttgcttttac agctcaatag tttaaaaaca aaacaaaaca    180

aaaagctgca gtaatccccc tgccgttatt catgaggatt acatttcacg acccccagtg    240

gatgtctaaa actagattag tactaaatcc tgtatacatt ttcctataca tatgtaccta    300

tgatggttta atttataatg tttgcacggg agattaaaaa caataactaa taataaaata    360

gaataactag agcaggccag gcaaggtgac tcacgcctgt aatcccagct ctttgggagg    420

ctgaggtg                                                             428
```

<210> SEQ ID NO 50
<211> LENGTH: 436
<212> TYPE: DNA
<213> ORGANISM: Homo sapiens

<400> SEQUENCE: 50

```
ttttttttta aaggatgaga aaaaattggt acacacgaac aatgctcaca aaacggctgg     60

gagaaaggca aaatctaagc atattataag ggtgggattc agaatacagg agggcagagg    120

gggctgccac tgtgatgggt gggaatgaag aaagggaact gctactgctc tgaaggagaa    180

gggaaagccc gctgtcgggc agtgtgtgtg cagagacagg aaactggctg aagcatccac    240

tgtgaagaat ggaagactgg gactacattt cccaaattct acttgtgtat tataaactgc    300

tacccatgaa gatggttcta tttgaaagta atatttaggc cgggcgtaat ctcagcactt    360

tgggattaaa cgcgtgagcc accacacccg gcccaagtct taaaaagaaa aaacaaaacg    420

acagggatat attatt                                                    436
```

<210> SEQ ID NO 51

<211> LENGTH: 475
<212> TYPE: DNA
<213> ORGANISM: Homo sapiens

<400> SEQUENCE: 51

```
tatgagatgg gggtcttact atgttgccca ggatggattt gaaatcctgg gcttaaggga     60

tcctcctgct caggctctgg actagctggg attacaggtg tgtgccacca caccttgctt    120

tcccactaat tctgttcctg ctagtttctt cccttacaag taaggtgggt catatttacc    180

tgtgagaaac tcagaaatac tcacttttcc aggacagctg ggtgaagag aatatgtagt    240

ggccactgta ctttgtagga aagacctagg gctgcccagc cagatgcagg ggcttcccgg    300

ggagaagttt cccgagaagg cccttctctt gcctgagtag catctttgtg ctcctttccg    360

tgatactcga ttgtcaagtg caacagaggg agaaggttgt catcatctag caataccttg    420

tgtgctgact gttgaaaggc cacattcaca tcatgctcag ttactgcagt gggtg         475
```

<210> SEQ ID NO 52
<211> LENGTH: 439
<212> TYPE: DNA
<213> ORGANISM: Homo sapiens

<400> SEQUENCE: 52

```
tggagagttg gatctcgtat cctgcctaga ctggtcttga acacctgggc taagcgatcc     60

tccacttcag cctccccaag ttcttggact acaggcgtca gccaccatgc ccagctccta    120

gtgtcctttt tagggtctta agcaccacaa agggaatctt gattaactag tgacaatcac    180

aacaagtcca cagccttgct cctagcctgc ctccatacag acagcaatta aataccacct    240

gtgtaaactg caggagagta gttcaaattt ggctgagtaa ctttttcctg gcatgaaaga    300

accggctcta atgactagtt cattccagat ttcactggac attagatcta gtgctttgtt    360

ttgtttgcaa catttcctat ttgcccacac ataaatggac tttggggtct aaggccccac    420

tgctcttcaa atggacatg                                                 439
```

<210> SEQ ID NO 53
<211> LENGTH: 519
<212> TYPE: DNA
<213> ORGANISM: Homo sapiens
<220> FEATURE:
<221> NAME/KEY: misc_feature
<222> LOCATION: (483)..(483)
<223> OTHER INFORMATION: n is a, c, g or t.

<400> SEQUENCE: 53

```
tctttcctca aatctttatt gtcagtctat cacctatata tctatagtta gggaagcttt     60

catatagagc aagggtgcac tccagatata tgattcatct actaattaat aatgaataac    120

ttgcaatgtg ccaggtgctc ttttaaaagc atttagatgt tttaacttat ttaaatctgt    180

aaacatttct tttaaaagta tgttatcagt aatgaaaatg gcctacatcc tactctataa    240

aggccagtag tttacttctt ggaatatcat cttggtcagt catgatctga ggagaatata    300

cacctgtttc aacagtgatt atcattgtat aaaatttttg aaacaccttt tggaattact    360

aaagggttgt gacacatctc tatgtacatt ctcagtaatg aaaattttta acttcaggga    420

gaattaaatt ttggaaagaa taaaaaatat ctaggccagg catggtggct ctaaaggtaa    480

ttntaaaagt cctcaaaatg ttttaattgt agcattgcg                           519
```

<210> SEQ ID NO 54
<211> LENGTH: 319
<212> TYPE: DNA

<213> ORGANISM: Homo sapiens

<400> SEQUENCE: 54

```
tttttaatg tgacccattt atttatttat ttatttatga tggagtctca aaaaaaaaaa     60
aaagaaagaa aaacaattct tgtaatccca gcactttggg aggcatatca cttgaggtca    120
ggagttggag acgagcctga ccaacatgaa accctatctc taaaaaagaa aaagacctct    180
ttgcaaacaa ccttggtgca aaagtttact actaccattt cattctcaac attaaggacc    240
tagtgtgctt ggtgggtgga caagaaaaca aatctaggaa agggaaagct tttctacaca    300
aagagtagta gcacctcaa                                                 319
```

<210> SEQ ID NO 55
<211> LENGTH: 352
<212> TYPE: DNA
<213> ORGANISM: Homo sapiens

<400> SEQUENCE: 55

```
ttttttttt tttttttaat ttttttttat ttatttattt tgagacagag tctcattctg     60
tcccccaggc tggagtgcag tggtacgatc ttggctcact gcagcctccg cctcctggat    120
tcaagcgatt ctcctgcctc agcctgccga gtggctggga ttacaggtgt gcaccaccat    180
gcccggctaa tcttttgtat ttttagtaga tatggggttt caccatgttg gccaggttgg    240
tctcaagctc ctgacctcaa ggatccgccc accttggctt cccaaagtgg ctgggttaca    300
ggcgtgagcc accatgccca gccagaatgc aaccatatgt ttaaagataa ta            352
```

<210> SEQ ID NO 56
<211> LENGTH: 232
<212> TYPE: DNA
<213> ORGANISM: Homo sapiens

<400> SEQUENCE: 56

```
ttgagacgaa gtgtcgctct tgttgcccag cctggagtgc aatagcgcaa tctccaccca     60
ctgcatcctc cacctcctgg gctcaagtga ttctcccgcc tgagcctccc gagtagctag    120
gactacaggc gcccaccacc gggcccagct aattttttgt atttttagta gagatggggt    180
ttcaccatgt tggccaggct ggtctggaac ttctgacctc aggtgatcca cc            232
```

<210> SEQ ID NO 57
<211> LENGTH: 446
<212> TYPE: DNA
<213> ORGANISM: Homo sapiens

<400> SEQUENCE: 57

```
tgagacggag tcttagttgt ccaggctgga gtgcagtggt acgatctcag ctcactgcaa     60
ccactgactc ccaggttcaa gcaattcttc tgtgtcagcc tcctgaggag ttggggctgc    120
aggcaagtgc caccacgcct ggctaacttt tgtattttta gtagagacgg ggtttcacca    180
tatcgctcag gctggtctca aacttctgac ctcatgacct gcccgcctct acctcccaaa    240
gtgttgggat tacaggcgtg agctaccacg cctggccaga actatcattt gattcagaaa    300
tctcatcatt gggtatctac ccaaagaaaa atagtttatt atatgaaaat gatacgtata    360
cttgcacatt tattgcagca tgctcacaac agcaaactgt atatatcaga aaagcttaat    420
attcaaaata tatagaaaat tcaaag                                         446
```

<210> SEQ ID NO 58
<211> LENGTH: 510
<212> TYPE: DNA

<213> ORGANISM: Homo sapiens

<400> SEQUENCE: 58

```
aattagctgg gcatggtggt gcacacctat agtcctaact acttaggagg ctgaggtggg     60

acgactgctt gagccgagga gtttgaaggc aatagagaga gactctgttt caaagaaata    120

aaatgtaaag acaaatttct ccttcctctt caaatatgag aatcatcata gccctcccta    180

actcctatat tttttagatt aatcaaactc agatttctca aacattctag aacacaactt    240

gatcttgcct cccaagatta acccttccag aactttttaa ctttgttaaa gtgcctgtct    300

ttccatcttt ttaaaataga gcttatcaaa gaatttctgt gaaagtttcc ctttgcttcc    360

tcaccggaat gatctgtgat cacattagga ttccatcttt gaaaactact atctaagcca    420

tctttccatt ttaagatttc tgaatacaaa aaaaaaatcc ctttttctta atttctctaa    480

aattcactga cttaatgggt cttattcttt                                     510
```

<210> SEQ ID NO 59
<211> LENGTH: 245
<212> TYPE: DNA
<213> ORGANISM: Homo sapiens

<400> SEQUENCE: 59

```
ttctttaaga gatggggcct ctctatgttg ctcaggctgg tcatgaattc cagccctcaa     60

atgatcctcc caccttggct tctccaagtg ctgggattac aggtgtgact caccatgctc    120

ggccagatca tcacttttct gtcacttaaa tctcttgata aaggtgcttg atctcaaatt    180

ttctcttctt taccttagct cctataccac taaagtcttc tttgaaaaaa aaaaaaatca    240

ctttt                                                                245
```

<210> SEQ ID NO 60
<211> LENGTH: 479
<212> TYPE: DNA
<213> ORGANISM: Homo sapiens

<400> SEQUENCE: 60

```
ttttttgag atggggtctc gctctgtcgc ccaggctgga gtgcgtgcag tggcacaatc     60

tcggctcacg gcaaactctg cctcccagat accacacaag gacttctccg agccagcttt    120

ctgagggtta actgagggct gaggggttca agaaggagga cacgggcaca gggactcacg    180

ggcagtgaga ggcagtgggg ccaatggcgt gaggagcacc agagagcagg agggaacggg    240

cccggggcgt gaatccggcc ccatgagtgc tcttcggccg cccaaaaccg gtcccatggg    300

taacagcgtg gccttcggca agtgactaaa gggcttcctg cctcagcttc cccacctgta    360

aacagaggat aacaatggca tgtactggat ctggcataaa gtaaatgttc aatagatagc    420

tagaaaagaa tgttttaaaa cctcagagat acattaggcg aaaataaaag ctgggctac     479
```

<210> SEQ ID NO 61
<211> LENGTH: 480
<212> TYPE: DNA
<213> ORGANISM: Homo sapiens

<400> SEQUENCE: 61

```
tgagacagag tctcaccctg tcacccaggc tggatggagt gcagtggtgt gatctcggct     60

cactgcaagc tccgcctcct gggttcacac ttctcctgcc tcagcctcct gagtagctgg    120

gactacaggc gcccgccacc acgcccagct aatttttttt gtagttttag tagagtcggg    180

gtttcaccgt gttaaccagg atggtctcga tctcctgccc ttgtgatccg cccgcctcgg    240
```

```
cctcccaaag tgctgggatt acaggcgtga gctaccacgc ccggccgtct tgtgtcttct    300

ttactgtgac tgggtcgttt ttaagaaagg ttatcagctt tgtgtttggt ttcccacagt    360

tgataaaaat ctatcaaaaa cattataatt tgcaaggaaa aaggtttttc aatggctgca    420

ggaaccagaa agaaatagca tttcttatct gtataaacac aaacatttaa agctagtcac    480
```

```
<210> SEQ ID NO 62
<211> LENGTH: 179
<212> TYPE: DNA
<213> ORGANISM: Homo sapiens
<220> FEATURE:
<221> NAME/KEY: misc_feature
<222> LOCATION: (165)..(165)
<223> OTHER INFORMATION: n is a, c, g or t.

<400> SEQUENCE: 62

ttttttttta atttcagaca gaatctcact cggtcgccca ggctggagtg caatggtgcg     60

atctcggctc actgcaacct ctgcctcctg gattcaggca attctcctgg ctcagcctcc    120

tgagtagctg ggattacagg cacccaccac catgcccagc tattntctgt atttttagt     179
```

```
<210> SEQ ID NO 63
<211> LENGTH: 307
<212> TYPE: DNA
<213> ORGANISM: Homo sapiens

<400> SEQUENCE: 63

gtatttttag tagagacggg gtttcaccat gttggttagg ctggtctcga acccctcacc     60

ttgtgatcca cccacctcgg cctcccaaag tgctgggatt acaggcatga gccaccgcac    120

ccggccctaa acatttgtta gacaatactt ccgaatgttt tgtctatgta atttagttca    180

caaatcattc agctcataaa tcaacttgtc tagactcatg ccctgggttc acagaattag    240

aaataatact attttacatt agggactact aagaacaacc aggatgatga taatagtcat    300

cactaaa                                                              307
```

```
<210> SEQ ID NO 64
<211> LENGTH: 275
<212> TYPE: DNA
<213> ORGANISM: Homo sapiens
<220> FEATURE:
<221> NAME/KEY: misc_feature
<222> LOCATION: (176)..(176)
<223> OTHER INFORMATION: n is a, c, g or t.
<220> FEATURE:
<221> NAME/KEY: misc_feature
<222> LOCATION: (245)..(245)
<223> OTHER INFORMATION: n is a, c, g or t.

<400> SEQUENCE: 64

tgtattttca gtagagacaa ggtttcagtc ttgaattcct aacctccggt gatccacctg     60

cctcagcctc ccaaagttct gggattacag gcatgagaaa ccatgcccag ccgatttctc    120

tcattttttt tttttttttt ttttaagaga caaggtgctc gctgtgttgc ccaggnctgg    180

tctcaaactc ctgggctcaa gcaatcctcc tgccttggcc tcctgagtca aaaagtgcat    240

ctcanatagt tttaaaatgg atgtgcaata tttag                               275
```

```
<210> SEQ ID NO 65
<211> LENGTH: 306
<212> TYPE: DNA
<213> ORGANISM: Homo sapiens
<220> FEATURE:
<221> NAME/KEY: misc_feature
<222> LOCATION: (231)..(231)
```

<223> OTHER INFORMATION: n is a, c, g or t.
<220> FEATURE:
<221> NAME/KEY: misc_feature
<222> LOCATION: (233)..(233)
<223> OTHER INFORMATION: n is a, c, g or t.

<400> SEQUENCE: 65

```
tttttttttt ttgagacagt ctcactttgt cgccaggctg gagtgtggag tgcagtggca     60

caatcttggc tcactgcaac ctctgcctcc tgggttcaag cgattctcct gcttcagcct    120

cctaagtagc tgggattaca ggcacacccc accacacccg gctaattttt atatttttag    180

tagaaagggg gtttacccat gttggccagc tgggtcttga actcctacct ntntggatcc    240

acccgcctcg gcttccaaaa gggggaagtc actgcaccca gccttgctgg atttttctaa    300

aacctt                                                               306
```

<210> SEQ ID NO 66
<211> LENGTH: 444
<212> TYPE: DNA
<213> ORGANISM: Homo sapiens

<400> SEQUENCE: 66

```
tttttttttt tttttttttt ttttgagatg gaattttgtt cttgttgtcc aggctggagt     60

gcaatggggt gatctcggct caccgaaacc tccagcctgg gtgacagagt gacaccctat    120

ctcaaaaaaa aaaaattctt cattgctcat atacgtcaga ttattacaat tttggtatgc    180

ttaaaaatca cagagagcca aataaggtgg ccaagagaga agaaaatgat aagttgtcca    240

cacaagcgct ctgatccaag ttaaaaacaa gcaaagtaag gtatgggagt acaaaatcac    300

aaaaatattt tagagcattt taaaaagggg gctattataa ttatcttctt ttaattatta    360

attttaatat cttaacatgc caccaaatta aattcttcct gaatagagaa agataagctt    420

ttaaaaattc tgcatcatta ctgg                                           444
```

<210> SEQ ID NO 67
<211> LENGTH: 311
<212> TYPE: DNA
<213> ORGANISM: Homo sapiens
<220> FEATURE:
<221> NAME/KEY: misc_feature
<222> LOCATION: (64)..(64)
<223> OTHER INFORMATION: n is a, c, g or t.

<400> SEQUENCE: 67

```
tttttttttt tttttttttt tttttttttt atttagagat ggggttttgc tctgttgccc     60

aggntggagt gcagtggcat gatcatagct cacagcagcc tctaactcat gggctcaagc    120

aactcttaca cttcagcctc caaagtagct gggactacag gcatgagaaa ccacacttgg    180

ctaacacaca cacacacaca cacacacaca cacacataat tgctatcatc tctatcaaat    240

atacacatat atttgatata tatgtatatt tgtgtgtgtg tgtgtgtgtg tatatatata    300

tatatatatg t                                                         311
```

<210> SEQ ID NO 68
<211> LENGTH: 441
<212> TYPE: DNA
<213> ORGANISM: Homo sapiens
<220> FEATURE:
<221> NAME/KEY: misc_feature
<222> LOCATION: (282)..(282)
<223> OTHER INFORMATION: n is a, c, g or t.
<220> FEATURE:
<221> NAME/KEY: misc_feature
<222> LOCATION: (356)..(356)

<223> OTHER INFORMATION: n is a, c, g or t.
<220> FEATURE:
<221> NAME/KEY: misc_feature
<222> LOCATION: (368)..(368)
<223> OTHER INFORMATION: n is a, c, g or t.
<220> FEATURE:
<221> NAME/KEY: misc_feature
<222> LOCATION: (373)..(373)
<223> OTHER INFORMATION: n is a, c, g or t.
<220> FEATURE:
<221> NAME/KEY: misc_feature
<222> LOCATION: (394)..(394)
<223> OTHER INFORMATION: n is a, c, g or t.
<220> FEATURE:
<221> NAME/KEY: misc_feature
<222> LOCATION: (404)..(404)
<223> OTHER INFORMATION: n is a, c, g or t.
<220> FEATURE:
<221> NAME/KEY: misc_feature
<222> LOCATION: (413)..(413)
<223> OTHER INFORMATION: n is a, c, g or t.
<220> FEATURE:
<221> NAME/KEY: misc_feature
<222> LOCATION: (424)..(424)
<223> OTHER INFORMATION: n is a, c, g or t.
<220> FEATURE:
<221> NAME/KEY: misc_feature
<222> LOCATION: (435)..(435)
<223> OTHER INFORMATION: n is a, c, g or t.

<400> SEQUENCE: 68

```
ttttttttt tttgagacag ggtctcactc tgtcacccag gctagagtac agtggcacaa     60

tctcggctta ctgcaacctc tgcctcccag gttcaagcga ttctcctgcc tcagcctccc    120

gagtaactag gaccacaggc acacaccacc atgcccggct aatttttgca tttttagtag    180

agacagggct tcaccatgtt ggccagggct ggtctcaatt tcttgacctc atgatccacc    240

agcatcggcc tcatgatgtg ctggggatta cagggcatga gncaacgcac tcgggcctag    300

tattcaattt tacagggcag ggccacctct tacctatttt cacaggaaaa ccagtnttta    360

cacagganca gtnaggaacc actggaattc agtnggtctt ttcngggggg ttntaggttc    420

acantggatt taaantacag g                                             441
```

<210> SEQ ID NO 69
<211> LENGTH: 435
<212> TYPE: DNA
<213> ORGANISM: Homo sapiens
<220> FEATURE:
<221> NAME/KEY: misc_feature
<222> LOCATION: (360)..(360)
<223> OTHER INFORMATION: n is a, c, g or t.
<220> FEATURE:
<221> NAME/KEY: misc_feature
<222> LOCATION: (372)..(372)
<223> OTHER INFORMATION: n is a, c, g or t.
<220> FEATURE:
<221> NAME/KEY: misc_feature
<222> LOCATION: (390)..(390)
<223> OTHER INFORMATION: n is a, c, g or t.
<220> FEATURE:
<221> NAME/KEY: misc_feature
<222> LOCATION: (395)..(395)
<223> OTHER INFORMATION: n is a, c, g or t.
<220> FEATURE:
<221> NAME/KEY: misc_feature
<222> LOCATION: (401)..(401)
<223> OTHER INFORMATION: n is a, c, g or t.
<220> FEATURE:
<221> NAME/KEY: misc_feature
<222> LOCATION: (415)..(415)
<223> OTHER INFORMATION: n is a, c, g or t.
<220> FEATURE:
<221> NAME/KEY: misc_feature
<222> LOCATION: (423)..(423)

<223> OTHER INFORMATION: n is a, c, g or t.

<400> SEQUENCE: 69

```
tgttgttgaa tattccttaa tggagtcgat gaatttgcag agacccctcc aagattcttt     60

tgtttgattc ctttcatgac catcacccta gaccttcaag tttgctgact agatttgggg    120

gttgtgtgtt tagaaaggat aacaagcttg tcatgggcta gaacctgtgg tcttcataaa    180

tagcttagta ggatatatgg ctttttctat gaaaggtgga gaacatgcat taaaaatggg    240

caaattctgg cctggggcat ggtggcttat gcctgttaat cccagcactt ggggaggctg    300

aagcgggcag gtcgtctgag ggtcagggag ttttgagacc agcctggccc aaaataatgn    360

aatcctgtct cntgctaaaa ctaccaaaan tagcntgggc ntggtagcac acccntagtc    420

ccngctactt gggga                                                     435
```

<210> SEQ ID NO 70
<211> LENGTH: 348
<212> TYPE: DNA
<213> ORGANISM: Homo sapiens
<220> FEATURE:
<221> NAME/KEY: misc_feature
<222> LOCATION: (212)..(212)
<223> OTHER INFORMATION: n is a, c, g or t.
<220> FEATURE:
<221> NAME/KEY: misc_feature
<222> LOCATION: (269)..(269)
<223> OTHER INFORMATION: n is a, c, g or t.

<400> SEQUENCE: 70

```
ttttttttt ttttttttt ttttttttt aaagagatgg agtcttgcca tcttacgcag     60

gatggtctca aactcctggg ctcaagcgag tctcctgcct tggtgtttca aagtgctggg    120

attacaggtg tgagccactg tgcccagcca acttctcatt ttaaaagaat ttcagattta    180

aaaaaattgc aaaaatactg cgagagaatc cncatatact tttcacccag atccaccaaa    240

tgttaacatc ttaaataacc atattatgnt gatcaaaacc agaaatacta ttaactactc    300

tacagacttg actcaaaatt caccaactgt ctgcctaatt ttagtcca                 348
```

<210> SEQ ID NO 71
<211> LENGTH: 304
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g or t.

<400> SEQUENCE: 71

```
tgtagagaca ggcgcttact atgttgccca ggctcggttt taaactccaa gcctcaagtg     60

atcctcctgc cttggattcc aaagtgctgg gattatagtt gtgagccact gcgcccaaca    120

ttcccatgac tttttgtga aggaggcatt caccaagctt ttcctaatct ttaccataag    180

ccaggctctg cggtaaacac cccacaataa atgtttatca gaggacttag cagggaagta    240

cattaaatgt taacgcctta atctgatact gaaaataaaa gataatttca acttggtttt    300

tnaa                                                                 304
```

<210> SEQ ID NO 72
<211> LENGTH: 192
<212> TYPE: DNA
<213> ORGANISM: Homo sapiens

<400> SEQUENCE: 72

```
gggcgtctcc ctatgttacc caggctggtc ttgaagtcct gggctcaagc aatgctcctg     60

cctcagcctc ccaaagtact gggattatgg gcatgagcac tgccctgcac ccagtcagaa    120

atgcttctct tgaataagca gttattagag gaattaaaca ttcaagaacc ctaacatgcc    180

cccaaacatc gt                                                        192
```

<210> SEQ ID NO 73
<211> LENGTH: 487
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is a, c, g or t.
<220> FEATURE:
<221> NAME/KEY: misc_feature
<222> LOCATION: (276)..(276)
<223> OTHER INFORMATION: n is a, c, g or t.
<220> FEATURE:
<221> NAME/KEY: misc_feature
<222> LOCATION: (300)..(300)
<223> OTHER INFORMATION: n is a, c, g or t.
<220> FEATURE:
<221> NAME/KEY: misc_feature
<222> LOCATION: (367)..(367)
<223> OTHER INFORMATION: n is a, c, g or t.
<220> FEATURE:
<221> NAME/KEY: misc_feature
<222> LOCATION: (384)..(384)
<223> OTHER INFORMATION: n is a, c, g or t.
<220> FEATURE:
<221> NAME/KEY: misc_feature
<222> LOCATION: (390)..(390)
<223> OTHER INFORMATION: n is a, c, g or t.
<220> FEATURE:
<221> NAME/KEY: misc_feature
<222> LOCATION: (475)..(475)
<223> OTHER INFORMATION: n is a, c, g or t.

<400> SEQUENCE: 73

```
ttttttttt tntctatttt tagcagagac ggggtttcac catgttggtc aggctggtct      60

agagctcctg acctcaggcg atccacccgc ctcagcctcc caaaatgctg gtataacagg    120

catgagccac agcgtctggc cagaatcata tcttaatagc aatcccataa tgtagtttta    180

ccagaaatac catagtcaat tttacagggt gggttcagtt tttcttaaat tacttacccc    240

taagattaaa gaatatttta aaatattgtt ataagngaca taactaaact attaggtttn    300

tgcaaaagta attgtagttt ttgccattaa aaggcaatta taaaggaaaa cggggatatt    360

aataggngtt acttctaggc ttgnaagggn taacattctt ttttggctac ttaaaagtaa    420

tgggcaaaaa ctggcaattg tttttggcac caacctatta gggcaagaga acccnatggg    480

ctttttg                                                              487
```

<210> SEQ ID NO 74
<211> LENGTH: 446
<212> TYPE: DNA
<213> ORGANISM: Homo sapiens
<220> FEATURE:
<221> NAME/KEY: misc_feature
<222> LOCATION: (381)..(381)
<223> OTHER INFORMATION: n is a, c, g or t.
<220> FEATURE:
<221> NAME/KEY: misc_feature
<222> LOCATION: (390)..(390)
<223> OTHER INFORMATION: n is a, c, g or t.
<220> FEATURE:
<221> NAME/KEY: misc_feature
<222> LOCATION: (442)..(442)
<223> OTHER INFORMATION: n is a, c, g or t.

<400> SEQUENCE: 74

```
ttttttttt aatagagatg gggatctca tcgtcaccca ggttggaatg cagtgatacc     60
atcacagctc gctgcagcct ccacctcctg ggatcaaccc ctacctcatt ctcctgactg   120
ggactacagg cactcaccac cacactgggc taattaaaaa aaaaaattct tttttgtagg   180
gaagtggtct tgctatgtca cccaggttga tctagaactc ctgacctcaa gtcacccgtc   240
cgcattatcc tcccaaagtg ctgaggatta cagacgtgag gccactgcac ttgggcctat   300
ttaggggctt ctaattcact ttccttttcc ttcttgtcta aattcttgtg tttttagaat   360
ctggcatttt attttaaggt natcttcaan tccttttggg aagtagtgag gggagtaaat   420
gcttaacctg tgtaggaaac cntttt                                        446
```

<210> SEQ ID NO 75
<211> LENGTH: 6213
<212> TYPE: DNA
<213> ORGANISM: Homo sapiens

<400> SEQUENCE: 75

```
cagtctttga ttggttgctg agaggcgggg ctactcgact gctctggagg tagcggccgc     60
ggtgaggaga gccatgggac gggcagtcaa ggttttacag ctctttaaaa cactgcacag   120
gaccagacaa caagttttta aaaatgatgc cagagcatta gaagcagcca gaataaagat   180
aaatgaagaa ttcaaaaata ataaaagtga aacttcttct aagaaaatag aagagctaat   240
gaaaataggt tctgatgttg aattattact cagaacatct gttatacaag gtattcacac   300
agaccacaat acactgaaac tggtccctag gaaagacctt cttgtagaaa atgtgccata   360
ttgtgatgca ccaactcaga agcaatgagt tttctagaat acaacaagtc tttgtacttt   420
ttaactttaa aatctacaac tctggcaaaa gtcctggaaa tgcagacatt ttccctgaac   480
tggcatattg aaaatgaatg aattacagaa tagcttcata tttaaatttc atgttaaaag   540
gtcattactg agaactaaag aacataatta agtatttcta aaggaaatta gataagaaaa   600
catttcattt tcattgaaaa tcaaatttca taaagcaaag taaatgctta gggagatata   660
ttcaatcttt gaccttgatg agtatttgat cttaccatag ctatttgaga atgtggtgct   720
tttacaaatt ggtgagtttt cctgccatgt gaaatgcaat tattacattt aaattgttag   780
attaaaatga tatttagtcc tgaaaaatat taaattggtc aaaaaaatca cagtgtatgc   840
cagctctcta cagaaagtgg cctttgtttt ctaaagcact gggattattt ctgtagctaa   900
tatataattg tacagtttct ttttagagat agagagtatc tctgtgttct tatgaagaca   960
ttttttatca gttttctgaa aatagatgaa taaaatatta tagtcaccta gggtcactat  1020
ggaataaaga aatcctagtt taaagaggaa atagtggccc ttgatcaaac tatttaatat  1080
ggccttagta gaattagctg tatttagaca aagttagact ttagtgtgaa atgtaatcgg  1140
tggctacatt ctcatcgttt taattaatga aacttaaatg gcttctcttc ttccacatgt  1200
cctgtccttg acaagatggg cagtatcaca aaaggtcctg gcattctacc atctaacact  1260
aggaactgta aaatactgtt taatattctt cttgtttctc ttttatctgt gtatctttgc  1320
cattctattt tctcagtgaa tagtatgttt tctcccattc actgataaat tctctcattt  1380
gatgatgata cagggttttt aatttttgca agattctcaa tgcaagcatt gttatgtatc  1440
tagaaattat acctagagaa aaatgaaagt cgtttcaaat ttgaaatttg cccttttaag  1500
agaatgctga atgtcatcgc agtatataat cactatataa atgtgctgac ttacagttat  1560
tttagtgtct atatgacata ttttgaggaa agttggctga cgttatttaa atttaatata  1620
```

-continued

```
tattctatat tttagtgtta ttgaatattt tatcactgag ctttttttctt taacctgaat   1680
tccctgttcc atttttcatt catattaatt taaataactc cagatttctt tcttatagtc   1740
attattagta gcagatgaga ttaataattc acatgtttat taaagatagt ggcttagaaa   1800
ttttaagata tattgatata ggcccgggcg ctgtggctca cacctgtaat cccgcacttt   1860
gggaggctga ggcgggcaga tcacaaggtc aggagttcga gaccagcctg gccaatgtgg   1920
tgaaacccca tctctactaa aaacacaaaa attagccagg tatggtggcg ggcgcctgta   1980
gtcccagcta ctcgggaggc tgaggcagga aaatcacttg aacccgggag gtggaggttg   2040
cagtgaactg agattgtgcc actgcactcc agcctggggg acagagtgag actctgtctc   2100
aaaaaaaaaa aagaaaaaaa aaggaaaaag gaaaaaaaaa agatatattg atacagatag   2160
gtagatatga tattgtactt tcatgccata agactacaca ataaagttcc tgaaagttcc   2220
tggctgggcg cagtggctca cgcctgtaat cccagcactt tgggaggccg aggcaggcag   2280
atcacctgag gtcaggagtt ctagaccagc ctgaccaaca tggggaaacc ctgtctctac   2340
taaaaaaaat acagaattag ccaggtgtgg tggcacatgt ctgtaatccc agctactcgg   2400
gagactgagg caggagaatt gcttgaaccc aggagacgga ggttgcagtg agccgagatc   2460
gcaccattgc actccagcct aggcaacaag agtgaaactc cgtctcaaaa ataaataaat   2520
aaataaagtt cctgtgaagt atataaacat gtcaacaaca ggcttgactg tcacaaaatt   2580
ctgaaagatg tcgcactcta ttcttatata gcatatgcta atttatttat ttatttttg   2640
agattgagtt ctgctgtgtc acccaggttg gagtgcagtg gcatggtcat ggtccactaa   2700
agccttgacc cctggggctc agcagttatg ccaactaagc ctcccaaata gctgagacta   2760
gaggtatgcg ccaccacacc tagctatttt ttttattttt agtaaggaca aggtctcatt   2820
atgttggcca ggctggtctc aaattcctga gctcagttga tcctcccacc tcagcctccc   2880
aaagtgctgg gattacaggt gtaagccact gcaccctgcc tattcttata atcatatatt   2940
tatatttcaa atggatttta actggttatt taatagttta attagataaa gtaattcatg   3000
gctgggtgtg gtggctcacg cctgtaatcc cagcactttg gcaggctgag gcaggtggat   3060
tacctgaggt cggaagttcg agaccagccc aaccaacgtg gagaaacccc atctctatta   3120
aaaatgcaaa attagcagga catggtgata cacacctgta atcccagcta gtcaggaggc   3180
tgaggcagga gaattacttg agccagggaa gcagaggttg tggtgagcta agattgtgcc   3240
actgcactcc agcctgagag aacaagactc cgtctcaaaa aaagaaaaaa agaaaacttt   3300
tttacacatg ggtatctcac catgttgccc aggctggagt gcagtagcta ttcataggca   3360
cagtcatagc acactgcagc ctagaatttc tgacctcaag caatcatcct gcctcagcct   3420
cctaagtagc taggactaca ggtgcatacc accataacca gctttaatta aatgtttttt   3480
atttggttat tttttttaag ttttctgtat tcacacaagg ggttgcccaa atataatttt   3540
gctttgacta ttgagatcta gtgaaagtgg ggtatatgaa ttctaattgc aaatatccag   3600
gctcagaggc ccagcaggac tttctaacac aatcttttag cggaagttag aaatggtata   3660
tagcaggaga gtcagatttg agaagcatat gtagattcga agctggggga atatggcagg   3720
tagtttgtac aacatctaat tcagaacatt aaaattaaga ttttagtcaa actgtgttta   3780
agttagttct tattttcctg tagatgcatc tcacagcatc agtacaatac caaaaaagca   3840
cacaagaata agaatatgtg gaatttctat acctattgac aaagcacata atttaaccat   3900
aaacacaaag ccataggtca acaaagaaat gaagattcca gttctgaagg tgagttttct   3960
gaagccaaag tggatacatg caaaattaat atagttttac tgtatatcag ttgtcaccaa   4020
```

tcagaaatgg aaaacagatc ctatttataa ttgcaaacaa aactgtaaaa tagacttttt 4080
aaagtctggg aatagacttc taaaataagc tataacactt aaaaaggaga gatatactat 4140
gttcctagat aggacaattg aaaattctgg agatgacagt ttttcaaaaa tctattgagg 4200
ccaggtgcag tggcccatgc ctgtagttcc agtactttgg gaggcctagg tgggtggatc 4260
acctgaggtt gggagtttga gaccagcctg accaacatgg agaaaccccg tctctactaa 4320
aaatacaaaa ttagccaggc gtggtggtgc atgcctgtaa tcccagctac tcgggaggct 4380
gaggcgtgag aatcgcttga acccggtagg cagatgttgc agtgagccga gatcgcacca 4440
ttgcactcca gcctaggcaa caagagcgaa actccatctc aaaaatagaa aaaacattta 4500
tcgaaatccc aacaagttga caaatatatc cacataaaaa tataaaactt ctgtattctg 4560
tgaaagctac tataaataaa gtttagagaa agttatttgc cacctatgtc atgattgaaa 4620
tagttaattg atcctgtgaa tcagttagca aaacataact caatggaaag ataggcaaat 4680
gatacaaata agaaattcac aaaagaagaa atactaagtc tctagtgatg agagaaatgt 4740
aaattaaaat gaaacatgtt tgttcatcaa gttgtcacaa gttagacaat catatccaat 4800
atttttaaag gttgtaagac tataaggaaa tagccactgt catatcattt ttaaaggaat 4860
ataaattata gggccttttg tttctttggg tttttttttt ttagagacaa gatctctccg 4920
tgttgtctag gctggactca aacttctgga ctcaagcaat cctcgcaaca tcattaatag 4980
ctgagagtag agacttgagc caccacacct gactataggg cctttttgaa aggaaaattg 5040
acatcatcaa aattttaaat atattcagtc tatttctcaa aaactcaaag aatactaata 5100
aatgtgtact caggtatatg tacagaaatt gctgtaacat tataatttta aacaatttaa 5160
aacagactga gtttccaaag ttagggtaca atgaaagaaa aggtggctta tttatactct 5220
ggaatatttt ccaagagttg aaaaggatga ggatacacac acacacacac acacacacac 5280
acacacacac acacacacac agtttgggta tccctaatcc agaaattcaa atgctccaaa 5340
gtccaaaact ttctgaccca ccaacatgac tgatgctcaa aggaaatggc cactggaaga 5400
tttcagattt tcagatttgg agtgctcaac cagtaagtat ataatgcaaa taatccaaaa 5460
tacaaaaaaa aaaaaaaaga aatctgaaac acttctgatc ccaagcattt cagaaaacgg 5520
atgttcattt gtgtgtgtgt gtgtgtgtaa gcaggtgttg ctagaaattc acttatatac 5580
aagaaaactt tttgtgtaca tatttgcata tatatgtaca aatgggtaga aacgatacat 5640
gattaatctt aatcgggaag gaaaagagat ttagggaagg aagcagtaag tgagaacttt 5700
tattctattt actcctgcac gtttaaatat tgtttacagt gagtatatca acatgtaagt 5760
gttaaaagac aataagctac tagtgatttt taatataaaa ttaactataa aatattttaa 5820
atattagcaa ataatatagc acactcatga acctaattcc cacatttgat agttgttaca 5880
ttttgccatg tttgtttaaa ggtctaagtc ataaaatctt ataaagctaa accccaccct 5940
tctctttctc ctctctctcc aggataatta ctgttttata gtttgtggat atcattccct 6000
tacttgtgtt tatactttta ccaagtgtgt atgtattcaa aaaacagttg ttttgtgatt 6060
ttaaaatgta aatgaatggc gttatgctcc atgtattctg caacttttca tcatacatta 6120
ggttttggcg atttagccat aatttggcat gaattcaggt cttttaagtt ttattccatt 6180
gtaagaataa acaagtttgt tcattcatgt ctc 6213

<210> SEQ ID NO 76
<211> LENGTH: 354
<212> TYPE: DNA
<213> ORGANISM: Homo sapiens
<220> FEATURE:

<221> NAME/KEY: misc_feature
<222> LOCATION: (184)..(184)
<223> OTHER INFORMATION: n is a, c, g or t.
<220> FEATURE:
<221> NAME/KEY: misc_feature
<222> LOCATION: (343)..(343)
<223> OTHER INFORMATION: n is a, c, g or t.
<220> FEATURE:
<221> NAME/KEY: misc_feature
<222> LOCATION: (351)..(351)
<223> OTHER INFORMATION: n is a, c, g or t.

<400> SEQUENCE: 76

```
gtaaaaggca aaaatttgag acttataagc tatatggtag cttatttttg ggtggggaag     60

aaatgagaaa agaatataac atctcttact ggcatgacac attttgataa aaaatcttat    120

tgtcctttcc tactaggaat gatccactgt aagggcaaaa ataatataca aggcaaagtt    180

tttntttggg aggacagagt ctcactctgt cacccgggct gggagtgcag tgggtacgat    240

tcttgggctc actggcaacc tctccctccc ggggttcaag gtgattcttc gtgcctcagc    300

ctcttgagta gctgggggtt tacagggcgc gtgccactgc gtnccggcta nttt          354
```

<210> SEQ ID NO 77
<211> LENGTH: 399
<212> TYPE: DNA
<213> ORGANISM: Homo sapiens
<220> FEATURE:
<221> NAME/KEY: misc_feature
<222> LOCATION: (175)..(175)
<223> OTHER INFORMATION: n is a, c, g or t.
<220> FEATURE:
<221> NAME/KEY: misc_feature
<222> LOCATION: (261)..(261)
<223> OTHER INFORMATION: n is a, c, g or t.
<220> FEATURE:
<221> NAME/KEY: misc_feature
<222> LOCATION: (336)..(336)
<223> OTHER INFORMATION: n is a, c, g or t.
<220> FEATURE:
<221> NAME/KEY: misc_feature
<222> LOCATION: (361)..(361)
<223> OTHER INFORMATION: n is a, c, g or t.

<400> SEQUENCE: 77

```
gcgtgtgtgt aaccttgaac tcctaggctc aagtgatcct cccaccttag cctctcaagt     60

agctgggtct acaggtgtgt accaccatgt ctggctaatt tattaatttt ttttgtagag    120

acagggtctc actatgttgc ccaggctggt cttgaattcc tgggcttcaa gtgancctaa    180

tgcctcagcc tcctaaagct ctgggactac aggcatgagc tatcatgccc agccagtact    240

aaataatttt taacaaaaga ntaaatcatt attttttata taaggtttct gtaagggggg    300

ctacaggatt tattatactt ttctgacatc caaagntttc aaatttggtt atatttttcc    360

ngatatatgg agggcccaaa atactttttt aataacctt                           399
```

<210> SEQ ID NO 78
<211> LENGTH: 510
<212> TYPE: DNA
<213> ORGANISM: Homo sapiens
<220> FEATURE:
<221> NAME/KEY: misc_feature
<222> LOCATION: (270)..(270)
<223> OTHER INFORMATION: n is a, c, g or t.
<220> FEATURE:
<221> NAME/KEY: misc_feature
<222> LOCATION: (361)..(361)
<223> OTHER INFORMATION: n is a, c, g or t.
<220> FEATURE:
<221> NAME/KEY: misc_feature
<222> LOCATION: (376)..(376)

<223> OTHER INFORMATION: n is a, c, g or t.
<220> FEATURE:
<221> NAME/KEY: misc_feature
<222> LOCATION: (492)..(492)
<223> OTHER INFORMATION: n is a, c, g or t.
<220> FEATURE:
<221> NAME/KEY: misc_feature
<222> LOCATION: (500)..(500)
<223> OTHER INFORMATION: n is a, c, g or t.

<400> SEQUENCE: 78

```
ttttgtagat aatggggtct taccatattg cccatgctgg tgtcaaactc ctgggctcaa     60

gcaatcctcc cacctcagcg tcccgagtag ctgggaccac aggcacccac caccatgcca    120

cactaaaatt tttttttgg gggggagggt agagaagggg tcttaccatg ttgcccaggc     180

tggtgtcaaa ctcctgggct caagcgatcc tcccacctca gcctcccgac atgtaaacgg    240

tggctacatt tccgcacaat ccccgcggtn tccctcattc tgttttacaa ctactcccac    300

ataaagtaac gtaggaaaga cggagccccg ttattccctt aggaagggta ggactgggag    360

ntttgcaggg aagctntagg ggattaaaca ttcagagggc caacttgagg attaaaacgg    420

aaacacccgg ggtgattttt aaggttaatt caagaggccc cttttcacgt gggggtgatt    480

ttttaaactt antcaggggn ctttttttca                                      510
```

<210> SEQ ID NO 79
<211> LENGTH: 392
<212> TYPE: DNA
<213> ORGANISM: Homo sapiens
<220> FEATURE:
<221> NAME/KEY: misc_feature
<222> LOCATION: (134)..(134)
<223> OTHER INFORMATION: n is a, c, g or t.
<220> FEATURE:
<221> NAME/KEY: misc_feature
<222> LOCATION: (374)..(374)
<223> OTHER INFORMATION: n is a, c, g or t.

<400> SEQUENCE: 79

```
ttcagagata gggtctagct ctgtcactta ggctggagtg cagtagatga tttatagctc     60

actgcaacct tgaactcctg acctcgtgat ccgcccacct tggcctccca aagtggtggg    120

attacaggcg tgcnccgttg cctggccatg ccagctaatt taaatttttt tttttgtaga    180

ggaaggagtc atgctacatt ccccaggctg gtcttaagct cctggcctca agtcggcctg    240

ggcttccaaa ttctgggatt atgggtttta cctgggccag agaagatata tttgaatcaa    300

acttaggggg acaaggattt ctgtacatca gtgttgtcct tgaggaaact gaaatgcagc    360

tttggggaaa gatnttttca gagcagagag aa                                   392
```

<210> SEQ ID NO 80
<211> LENGTH: 498
<212> TYPE: DNA
<213> ORGANISM: Homo sapiens
<220> FEATURE:
<221> NAME/KEY: misc_feature
<222> LOCATION: (33)..(33)
<223> OTHER INFORMATION: n is a, c, g or t.
<220> FEATURE:
<221> NAME/KEY: misc_feature
<222> LOCATION: (298)..(298)
<223> OTHER INFORMATION: n is a, c, g or t.
<220> FEATURE:
<221> NAME/KEY: misc_feature
<222> LOCATION: (328)..(328)
<223> OTHER INFORMATION: n is a, c, g or t.
<220> FEATURE:
<221> NAME/KEY: misc_feature
<222> LOCATION: (426)..(426)

<223> OTHER INFORMATION: n is a, c, g or t.
<220> FEATURE:
<221> NAME/KEY: misc_feature
<222> LOCATION: (479)..(479)
<223> OTHER INFORMATION: n is a, c, g or t.
<220> FEATURE:
<221> NAME/KEY: misc_feature
<222> LOCATION: (487)..(487)
<223> OTHER INFORMATION: n is a, c, g or t.

<400> SEQUENCE: 80
tttttaagta gagatggggt tttgccatgt tgncagggtg gtctcaaact catagcctca 60
tgtaatccac ctgcctcgac ttccaaaagt gctgggatta caggtgtgag ccactgtgac 120
cagcctgact tcaaatcctg tgttgaatag aagtagtgag atcgggcatc cttctcttat 180
tcctgatctt ggaggcaaag atttcagtct ttcacctaaa atgactgaaa gactttcagc 240
catgggcttt gcatgactgg cctttatttt gttgctgtac attccttctt ttcctggntt 300
tgggagtgtt ttaccagggg aaagggtntt caaggctggg ggcaccgtgg gcctcaagcc 360
ttgcaaattg cccagcactt ttggggaggg ccaagggtgg ggcgctccgt gcccaatttc 420
ttgggncctc gagggccaaa atttccccaa taagtgaagg ccgtatttta aaattccgna 480
aatcaangtc aaaaggct 498

<210> SEQ ID NO 81
<211> LENGTH: 325
<212> TYPE: DNA
<213> ORGANISM: Homo sapiens
<220> FEATURE:
<221> NAME/KEY: misc_feature
<222> LOCATION: (4)..(5)
<223> OTHER INFORMATION: n is a, c, g or t.
<220> FEATURE:
<221> NAME/KEY: misc_feature
<222> LOCATION: (273)..(273)
<223> OTHER INFORMATION: n is a, c, g or t.
<220> FEATURE:
<221> NAME/KEY: misc_feature
<222> LOCATION: (278)..(278)
<223> OTHER INFORMATION: n is a, c, g or t.
<220> FEATURE:
<221> NAME/KEY: misc_feature
<222> LOCATION: (293)..(293)
<223> OTHER INFORMATION: n is a, c, g or t.
<220> FEATURE:
<221> NAME/KEY: misc_feature
<222> LOCATION: (303)..(303)
<223> OTHER INFORMATION: n is a, c, g or t.
<220> FEATURE:
<221> NAME/KEY: misc_feature
<222> LOCATION: (311)..(311)
<223> OTHER INFORMATION: n is a, c, g or t.

<400> SEQUENCE: 81
cccnnctggt ttcaaactcc tgacctcaga tgatccaccc acctcagcct cccaaagtgc 60
tgggattaca ggcgtgaggc accacaccca gcccagatga gcttcttttc ttgtttattg 120
ccaaataaga gtcctttgaa ttatacatca tgttgttttg agccattcac atgctgatga 180
acatttgagt tgtttttcac tttttgacta ttattgatgc tgctgtgaac gttcacctgc 240
gtgtgcttgt gtggggcatt ctgaggacca gancacgngt aagcaaaagt gangctacat 300
ttngttggga natgatgctg gtatc 325

<210> SEQ ID NO 82
<211> LENGTH: 431
<212> TYPE: DNA
<213> ORGANISM: Homo sapiens
<220> FEATURE:

<221> NAME/KEY: misc_feature
<222> LOCATION: (10)..(10)
<223> OTHER INFORMATION: n is a, c, g or t.
<220> FEATURE:
<221> NAME/KEY: misc_feature
<222> LOCATION: (26)..(26)
<223> OTHER INFORMATION: n is a, c, g or t.
<220> FEATURE:
<221> NAME/KEY: misc_feature
<222> LOCATION: (41)..(41)
<223> OTHER INFORMATION: n is a, c, g or t.
<220> FEATURE:
<221> NAME/KEY: misc_feature
<222> LOCATION: (43)..(43)
<223> OTHER INFORMATION: n is a, c, g or t.
<220> FEATURE:
<221> NAME/KEY: misc_feature
<222> LOCATION: (270)..(270)
<223> OTHER INFORMATION: n is a, c, g or t.
<220> FEATURE:
<221> NAME/KEY: misc_feature
<222> LOCATION: (282)..(282)
<223> OTHER INFORMATION: n is a, c, g or t.
<220> FEATURE:
<221> NAME/KEY: misc_feature
<222> LOCATION: (377)..(377)
<223> OTHER INFORMATION: n is a, c, g or t.
<220> FEATURE:
<221> NAME/KEY: misc_feature
<222> LOCATION: (389)..(389)
<223> OTHER INFORMATION: n is a, c, g or t.
<220> FEATURE:
<221> NAME/KEY: misc_feature
<222> LOCATION: (397)..(397)
<223> OTHER INFORMATION: n is a, c, g or t.
<220> FEATURE:
<221> NAME/KEY: misc_feature
<222> LOCATION: (410)..(410)
<223> OTHER INFORMATION: n is a, c, g or t.
<220> FEATURE:
<221> NAME/KEY: misc_feature
<222> LOCATION: (417)..(417)
<223> OTHER INFORMATION: n is a, c, g or t.

<400> SEQUENCE: 82

```
cggagtcccn tcgttgttgc ccaggntgga gtgcaatggc ngntctttgg ctcaccacaa     60

cctccgcctc ccgggttcaa gagattctcg tctcaaactt ccgagtagct gggattacag    120

gcatgcacca ccacacccgg ctaattttgt atttttagtg gagacagggt ttctccatgt    180

tggtcaggct ggtcttgaac tcccgacctc aggtgatccg cctgcctcgg cctcccaaag    240

tgctggggat tacaggcgtg cgacccacgn cccagccacc tnttaaattt cttaatcacg    300

gattgttttc agctcaggac atacacaagg gcaagtagga attactaata aaatcacttt    360

taccctcaac cattcanggt ctctaaggng catgcanagg ggttacatgn cgggggnaag    420

ggaaggcact t                                                         431
```

<210> SEQ ID NO 83
<211> LENGTH: 2350
<212> TYPE: DNA
<213> ORGANISM: Homo sapiens

<400> SEQUENCE: 83

```
atatgccttt ttaaaaaaat tatcttttcc attggtgact atgaggttga gagatgattc     60

tcctacattt ctggctgctc ctcttcaagt accttccctg gctcctctgg atttttttgt    120

tttgttttgt tttgttttgt tttgtttttg agacaaagtc ttgctttgtt gcccaggctg    180

gagtgcagtg gcaggatctt ggctcaccag ctcactgcag cctccacctc ccgggttcga    240

gggattctgg tgcctcagcc tccagagtag ctgggactac aggcccggct agtttttgta    300
```

```
cttttggtag agatgggggt ttcaccaggc tggtcttgaa ctcctgcctc gggtgatctg    360

cccgcctcgg cctcccaaag tgctgggatt ctaggcatga gccaccgcgc ctggcctggc    420

tcctcttctt cttccactca gatatgcctg accctgtcaa cactttggtt gaggtcttct    480

ttcttctttc ttttttgctc cgcacattta gcttatgact tcaaccatca tttctcagag    540

catgggtctg gctcaacctc tctcctgaat ttcagaccta caagtctagc tacttggtgg    600

agacctcccc agaatgacct gctgcttccc aaaagcagac tctccaaatt acagtcagta    660

tctcccccgg aagcattccc ccaggcattt ctctttctgc cttcaattcc ccattctcct    720

acattgcctt gccagaagcc tgctggtcag cttggatttc tttttgtcct tttttttcta    780

tattttgctg gtgcctagtc atgtagttgc tgcctctaca ctttctcttc tttaaaaaaa    840

attattaaag caccacgtgc ttgttgtaaa catttccaga aaatacagaa gtgctcaaag    900

tgaaaaaatg gaaatgcctt gtcccttcct cattccctgc cctaacctca cgccccagat    960

tcagctatgt aatagtctgt catgccaagt cttatttcca gctcctcttt tccatcccca   1020

ctgccatcat ctgaactaaa cggattgttt tccatctggt ctccttggct tttcctttca   1080

gtgcagctca acagacatta atcaagtgcc ttccacacac caaagtccta ccctagatcc   1140

tagaggttca gagacaagta agatagttaa agagatccac attccagagc tgtttaactt   1200

tgggcaagtt acttaatctc tctgaccctt acttccttat ctgtaaaatg atgctaatcc   1260

cagcaccttt ttcatgggtt tggacgagca ttaatgagat gatccatgta aaactctttg   1320

tactaactac ctggtacact gtatctgctc cataaatgtc agtgacaaca atgataataa   1380

tgacaatgtt tggaggagtt tatagcttaa tggagagact taaagcataa gaattatcta   1440

ggcgaagaat gatgagaaaa tatttttgga aaaggaaaac aaacagttct actaaaatta   1500

aaaggctgat gtagaggctt gggaaactgg gaggtaagag ctcggactgt gtcctctaag   1560

acagtaattc ccgaagtgtg agcaaaagtc cacctgcatc agtcttactt ggggtgattg   1620

ctcaaaatga ggatttaatg gctgcacctc cgagcaagtt ggtaatttac atatcggaat   1680

gctatccatc aaggaaaatg ggcagactac agttacatgc atcaacacag acaagcttca   1740

aacaatattg agtgtaaaaa gcaagacata gaaatatata tttagtaaga gtaaaaatac   1800

agtaaaggta aaaaagaggc aaaactaaac aatatattgc ttaagcaata aggatacaca   1860

aactaatgaa aatcaaagga tttactaata caaacttcag tatagtaatt aattggaatg   1920

ggagagaaag atgcaaagtt tctatttctt tttttgtttt gttttgagac agtgtctcat   1980

tctgttgcca aggcaggagt gcggtggcag gatctcagat cactgcaggc tcagcctcct   2040

gggttcaggt ggttcttctg cctcggcctc ccgagtggct gggattgcag gcatgcacca   2100

ccacgcccgg ctgatttttg taattttggt agagatggag tttcaccgtg ttggccaggc   2160

tggtctcgaa ctcctggtct taagtaatcc gcccacctct gccatcaaag tttctgtttc   2220

ttaagttggc tgccgagtac acaggttttc tttgtaaaat aattatttaa attgttaata   2280

tgcattactt atatgctttt catttacaat gtatttcaca agaaaaataa aacaaagcaa   2340

ataagaaaac                                                         2350
```

<210> SEQ ID NO 84
<211> LENGTH: 184
<212> TYPE: DNA
<213> ORGANISM: Homo sapiens

<400> SEQUENCE: 84

```
gttgcagaga tggtgaggat gtcttgcttt gttacccagg ttggtcttga atttgtggct     60
```

```
ttaagtgatc ctcccacctt ggcctcccaa agtgctcggg ttacaggcgt acaacagtgc    120

ctggcctgta ttttattgta attccttttt ccattctcat ctcaatgcat ttccaaatta    180

gaga                                                                  184
```

<210> SEQ ID NO 85
<211> LENGTH: 410
<212> TYPE: DNA
<213> ORGANISM: Homo sapiens

<400> SEQUENCE: 85

```
aaaatatcag ctttattacc aaggatgact gtgctgcagg aggcggctca gtgtgaagaa     60

ctacgggttt cctgatgttg aagctcagaa ttagccacac tgaccttctc agtcatgcat    120

gatgccagga aaatcacagg cttccattct acagtgaagg gcttggagga gcaggcaata    180

atctgtagtc cccagctact tggaggcagt ggacgggaag atggcttgag cccacggagt    240

tccaagttgt agtgcactat catcatgcca ctgcatctgc actccagcct gggtgacaga    300

atgaaactct gtgtctccat tccccgtggt ttgcttggtt tggtttgatt tgggtctggt    360

cttactactg ctgcctctcc gtttgactgg caaagtgtgg actgggcact               410
```

<210> SEQ ID NO 86
<211> LENGTH: 16459
<212> TYPE: DNA
<213> ORGANISM: Homo sapiens

<400> SEQUENCE: 86

```
gtgcaatggt gcaatctcag ctcgctgtaa cctccgcctc ctgggttcaa gcaattctcc     60

tgcctcagcc tcctgagtag ctgggattac aggtgcctgc caccatgcct ggctaatttt    120

ttgtattttt agtagacaca gggtttcagc ttgttggcca ggctggtctc gaacccctga    180

tctcaggtga tccacctgcc tcggccaccc aaagtgctgg gattacaggc atgagccacc    240

gtgcccggat gaaaagtgct tttaaaaaag cataccccgt ctctactaaa aatacaaaaa    300

aaaaaattag ccagacatgg tggcaggcgc ctgtagtccc agctactcgg gaggctgagg    360

caggataatg acgtgaaccc gggaggtgga gcttgcagtg agccgagatt gcgccactgc    420

actccagcct gggcgacaga gcgagactct gtctcaaaaa ataaataaat aaataaaata    480

aaaataaata aaaaagcata aaataattca atttttttga aggactttta gaaactgttt    540

aattttagaa actatctgat tgtgatacat gctaacacac tcatatactc cctcctcccc    600

acaacacaca cacagcctct ctttgtcgct cataaagtct tcggaagctt tctcagtgct    660

tttaggagta tgacagaagt ccttacatgg ccaacaggaa cctgcatggt cttttcacca    720

cttactgtgt cttcctcatc tttctgttgt gctccccctt gtgctctcct ccagccctgc    780

tgtcattcct ccacatggaa gtcttttttt tttttttttt tttttgaga cagagtctcg    840

ctctgtcgcc aggctggagt gcagtggcgc aatctcggct tactgcaacc tccgcctcct    900

gggttcaagc gattctcctg cctcagcccc cccaagtagc tgggactata ggagcacacc    960

accacgtcca gctaattttt gtatttttag tagagacagg gtttcaccat gttggccaga   1020

tctgctgacc tggtcgtgat ctcctgacct tgtgatccac ccacgttggt ctcccaaagt   1080

gctgggatta caggtgtgag ccaccgcacc cggccaggaa gtctttttttg actcctgcca   1140

tgttctcctg gcacttcttc cttatacaga gatcacacat gcacattgta catttgctca   1200

gtgagtgtag ggactgctgc tctggttttc ttgtttgttt gttgcttatt tctgtatcac   1260

caggatctaa cacaatgctt ggttagctgt acccgagtat ttactgagtg catgaattcc   1320
```

```
atccattgta ttttctgtag ctacctgatc tttatttgaa cctttcaaga tatctcattc   1380
cattttggtg ttcttattat aatagaaatt agagaaaata tttgcaacca aaatgagaaa   1440
aaggtaatat taatatacaa aaagctcata taagttactg aagaaaatgt ctaaagccct   1500
aataaatagg caaagaatgt aaatagctaa gtcacaaaag aaatcttaga atgcttaaaa   1560
gatccaggtg caatggttca tgcctgtaat cccaacactt taggaggcca aggcagtagg   1620
atcacttgaa gccaggagtt acaagcttag caacaaagca agacctcatc tctacaaaaa   1680
acaaaaaaat aaaaaaacta gccaggcgta gtggcactca cctgtagtcc cagctattct   1740
agagccaagg gagggaggat tgccttgagc ccagggattt gacgctatgg tgagctatga   1800
tcgtgtcact gcactcagcc tgggcaataa agagacacac tgactcttaa aaaaaatggc   1860
caaaagagat ctgagaataa ttatctttac taggcatcaa ataagtgcaa atcaaagcaa   1920
actgccacct attaattgag caaaacattt aattgataat ctatttttca gaatgtattg   1980
gtctagttag aatatcaatt cttacctttc tgacagatga ctagtccttt gtaaataccc   2040
agtcacctct tttcagttaa agttgctgtc tccaaggagt ttgcaatcta attggggagg   2100
taaaatctca actcaagaaa tgagaagtca gcatgaaaac ccattgatgt cgtattgctt   2160
ttgctgctct gatgtggtgg ctcacacctg taatcccagc actttgggag gctggggtga   2220
gaggatcact tgaacccagg agttcaagag cagcctgggt aacatggcca aaccctgtgt   2280
caaaaaaagt ttttaaaaat tagcccggcg tggtggcaca tgcctgtagt cccagctact   2340
caggaggctg aggtgagagg atggctggag gctggcaagt agaggctgta atgaactgag   2400
atggtgccac cagaaggacg gagtttccct taaccaagat aatatgtata gtggctagtc   2460
tggcacatgg cacttactgg gtattccata aagagtagtt tatttcccca aaatgtagag   2520
taagagtgaa agactttgat ccaatgtact tctgtccacc tacacaagca aatagaatgt   2580
ttcaccagaa taattagaca aaaaatttta tatgtaattg gcacattgga atccttgtaa   2640
attactcctt ctgttggcca agagatttac tcctttggtg gaacttgtgt ttttccatat   2700
gacaataata tagtaatggc aagtatatca ataataataa aactttttt  aaaaagtaaa   2760
gggaaaatct taccaaatta atgtttcatt ttaaggaaaa tatgactcta tgcccatttt   2820
tttccttcca ggatgttgcc ttatggctgt ttagcaacag gagatcgctc tggcctcatt   2880
gaagttgtga gcacctctga aacaattgct gacattcagc tgaacagtag caatgtggct   2940
gctgcagcag ccttcaacaa agatgccctt ctgaactggc ttaaagaata caactctggg   3000
ttagtttatt ctgtttaatt atcatttttc tgtacaaaca gccaaacaaa tactgtatgc   3060
tcccaataga agtcagcagt gtgttagagg aaatattagt gtttttatc tattgcttca   3120
tttcttgtta gaacaaaatg acacatagcc cttcgtaaag tcttgtaaat ggtgaatgtt   3180
gaattctact ttatctaaat caaattttgg agccccgcag taaagttaca atctatgaat   3240
ttaagtattt aaagataaca tactgaagcc tttgttcaag tgcatcagct tctctaatta   3300
tgtgaatata tgaacttaag tgagttttta atgagttggt agattgtgat ttctccaaac   3360
taaaaaatgc aatgtttgga attatggcta tggtgttaga aaagcactaa tatataggaa   3420
ataaaagaac ttcacagtgt gagggggaaa tggtctgcaa gtatttttgg ctaaagactt   3480
cagagtcaga cacattttat cgagaacttg taatatgcaa atcagtttcc aaattttgat   3540
cttaaggcct tgtctccagg gaatctctat tacttacttc taattgaaat cagtgactta   3600
aatgtttgaa actgcagtgc ttaactctta aacatgaaat tgtagtcagt ctttggtcaa   3660
aactaactaa aatgttccca accoctagca tgatctagca aagccatggt ctcttctaag   3720
```

-continued

```
tactgtgaac atgagtctac tcacagcccc accgaaacac agctcccagg acgtttgaat   3780
atctaaggcc cagttattta atgtctttga aggcagctct ctcagcccag cccctgtgaa   3840
gaccacccac actccccttg gctgatccac atgttctctc atacggtttt ggcagctctg   3900
tgttctcctc acaattaaaa aggaaacaga ggtatggttt gggtctcact ctacacgctt   3960
ggaggctgaa aacctttttt gcttctgttc ttttctcttg ttcagggatg acctggaccg   4020
agccattgag gaatttacac tgtcctgtgc tggctactgt gtagcttctt atgtccttgg   4080
gattggtgac agacatagtg acaacatcat ggtcaaaaaa actggccagg tgagctgctc   4140
ctcaggatct gccaagggcc ttagtaatgc tatttcttat gtatagcata atctcttgtg   4200
caactcagcc agattctttt gtgattctta gtgtcatatc tttgtcttta cttcaatttc   4260
tcactacctc tcgtttcata tatagtctac tacatgtatt catttgtttg cttgcttgat   4320
ggtaagcatt tatttgttta aaaaattact aaaggctgtg tgtggtggct cacgcctgta   4380
atcccagcac tttgggatcc cgagccggcc ggattacctg aggtcaggag tttgagacca   4440
gcctggtcaa catggcgaaa ccccgtctct actaaaaata taaaaattag ccaggcatgg   4500
tggcaggcgc ctgtaatccc agctacttgg gagactgagg caggagaatc acttgaacct   4560
gggaggcgga ggttgcagtg agccgagatc gcctcactgt gctccagcct gggcaacaag   4620
agtgaaactc catctcaaaa aaaaattatt gaaaaaattt ttgtagttaa agtggcctgt   4680
tcttcaatat aagaaatagt atttgggata catttgtacc taacagaagg agcggataat   4740
gtactggatg tattaaattt aaagattacc aatgctattc atatcctttg cccacttttt   4800
gatggggttg tttgtttttt tcttgtaaat ttgtttgagt tcattgtaga ttctggacat   4860
tagccatttg tcagatgagt aggttgcgaa aattttctcc cattttgtag gttgcctgtt   4920
cactctgatg gtagtttctt ttgctgtgca gaagctcttt agtttaatta gatcccattt   4980
gtcaattttg gcttttgttg ccattgcttt tggtgtttta gacatgaagt ccttgcccat   5040
gcctatgtcc tgaatggtaa tgcctaagtt ttcttctagg gtttttatgg ttttaggtct   5100
aacgtttaag tctttaatcc aaaagaagac atttatgcag ccaacagaca catgaaaaaa   5160
tgctcatcat cactggccat cagagaaatg caaatcaaaa ccacagtggg ataccatctc   5220
acaccagtta gaatggcaat cattaaaaag tcaggaaaca acaggtgctg gagaggatgt   5280
ggagaaatag gaacactttt acattgttgg tgggactgta aactagttca accattgtgg   5340
aagtcagtgt ggcgattcct cagggatcta gaactagaaa taccatttga cccagccatc   5400
ccattactgg gtatataccc aaaggactat aaatcatgct gctataaaga cacatgcaca   5460
cgtatgttta ttgcggcact attcacaata gcaaagactt ggaaccaacc caaatgtcca   5520
acaatgatag actggattaa gaaaatgtgg cacatatata ccatggaata ctatgcagcc   5580
ataaaaaagg atgagttcat gtcctttgta gggacatgga tgaaattgga aatcatcatt   5640
ctcagtaaac tatcacaagg acaaaaaacc aaacaccgca tgttctcact catagatggg   5700
aattgaacaa tgagaacaca tggacacagg aaggggaaca tcacactctg gggactgttg   5760
tggggtgggg ggagggggga gggatagcat taggagatat acctaatgct aaaggacgag   5820
ttaatgggta cagcacacca gcatggcaca tgtatacata tgtaactaac cggcacattg   5880
tgcacatgta ccctaaaact taaaataaaa aaaaaaaaaa agattaccaa tgctaaaaaa   5940
aaaaagttgg gatgaacccc acttgagtta ttttctcttt tagaacatca tacctaatta   6000
tatatgggag aagggagaac agtcgtgtga gtaatagcat tctggggtac ctagggaatc   6060
tagaccatgt tgtttataaa gtacttaagt tttcaaatga aaatttcatt tttcagagtg   6120
```

```
acatatttgt aaacactttt tatgttaagc aaaaacagat gagatatctt agataatttt   6180
tcagtttagc cccccctagga attcccacat tagaggcata ctagaatgaa aatctctctg   6240
ggtcactgtg tgaactttgg ttctatgagg gacccacagt tttgtatctc cttggaaatc   6300
tggattagtt ctggcttggg ctttgagagt tgatgtggaa tgaatttgta atgcactata   6360
atacatgaat gcaccatgta cgattgagga atctcgtgtc catacttaaa aggagtccct   6420
tggacttccg tccaatcaca ttaaacactt agatttatct ccattttctt cttttacacc   6480
tctaaaacaa taataaggaa ttaagaaata tataaactca agaagtcaaa gatgatagga   6540
aaataggcca cagtgggtga aacctattac cagacttcgg ggtgatagaa agtgagatag   6600
agaagtggca gtgacttagc agaactgaga aaatagaaag tcagtacttg taaaggggta   6660
cgcaagtccc ataaaagctc tggaatcaga ggcaccatgt atactgttca aggagggata   6720
cagaaagagg ctgaaacaga actagttggc agcttatata tggaaccagt taggcactca   6780
agtccccttc ccttatgcca agaaggagac agatttattc tctgaagaaa ctggttctga   6840
ctcaagcaca cttatttcta cagagactac aagaaagggt cccatattaa aaatggagat   6900
ggagtgaaag tcggcgtagt aaatggtaca atctgcagcc acttccactt gctttattct   6960
aagaacagtg gcagccagat gtatagttga ccctcatcaa aagactaggt gattctattc   7020
tagaaatctg attggttcca ttgaaaagtc ctgcagatct gacagttgag atttctccct   7080
agtttctata caaggaagtc caccaatcaa caagcaagcc taccatgtac atagaatttt   7140
cattcagctt tttagtgatt cattgttaaa tatgaatggt cagctaagga ttaatatact   7200
tttaaaaaat gacaaaaatt gaatatgttt atcatgtacg acatattgtt ttgaagtatg   7260
tcttcattgt ggacttgata aattgagctg acctgtgtgt tacctcacat acttatcttt   7320
ttttgtgatg ataacattta aaacctagtc tttcagcagt tttcaggaat acaatatatt   7380
gttgttaact atagttgcca tgttgtaaga cagatctgtt gaacttattc ctcctaagtg   7440
aaattttgta ttatttgacc agtatctccc cagcacctgc agccaccatt ctactctcta   7500
ctggattagc agacatttaa gggaaacctc taccatgaaa gatagaaacc aaataggcaa   7560
aatagggaag aaaagaaaag aactctggga aaacagggta actgcagtaa acagagggtg   7620
attttaaaaa tcaaagcaaa aaaatatatt gtatctttaa agtaataata ggattctgtt   7680
ttttacaatc agcacataga ggtcttgaaa attagaaata ggaacaaaca aaaagttaaa   7740
atagaaatag tgtaaatatt ttgtggcagg catagttgta agtgctttat atataatcta   7800
atgccttcag gcctgatgac aaccttatag agtggcggca atagccccat tttacaagtg   7860
aggatattaa ggcaacagag agtagacata tcaggatttt aaccctggga gtttggctca   7920
tattcttttt ttttaatcca ccatgcctta atatctccaa aaaatatgat aaatagagag   7980
aagatccaga aacaatagag actcagtcca gggaggtata ctctcagcct aatggatatt   8040
ccagaaagaa ggagaatggc gtgaacctgg gaggtggagc ttgcagtaag ctgaaatcac   8100
gccactgcac tctagcctgg gcgacagagc gagactccgt ctcaaaaaaa aaaaaaaaaa   8160
aaaaaaagaa gaggaaagaa gggcacttac taagcaaata atatactaag acatttccca   8220
gagccaatgt tcatgaatat ccagtcaaaa tagcacaaaa attttctgag aacggaagaa   8280
aaacaccctt actaagtacc tgcactatga aatttcagtg catcagacgt aaagagaaag   8340
tcttaaaact ttcacagaga cacagcaggc cacataccag agtttagaag tcaaaatgac   8400
ttggctcctc aatagctaca ttggcaatta taagacagtg cacgttagcc ttcataattt   8460
tgagggaaaa tgatttctaa cctaaaattc gataaccaaa cttttttttt tttttctgag   8520
```

-continued

```
acggagactt gctctgtcgc ccaggctgga gtgcagtggc gtgatcccgg ctcactgcag   8580
cctccgcctc ctgggttcaa gtgattctcc tgcctcagcc tccccaggca gctgggggac   8640
cacaggcatg cgccaccacg cccagtcaag tataaagggt agaatgaaga catttttcca   8700
acttgcaggg tcacaaaact tgtcactcct ctgcatcttt tctcagaggc tgccagaata   8760
aggacatcta ccaaaacaag tgcctaaacc aataattatc aagtggggtg atttttcact   8820
caggggacat ttgttaatat atgaaaacag ttttagttgt cataactggg gggtggggta   8880
gtccagtgga tagaggccag ggatgctgct aaacacccat acaggacaga accccatatc   8940
aaagaattat atggcctatg tcagtgtgtg ccagtattga gaaaccctgg tctcaaccaa   9000
aagagaatgt gatgtggaca caaaacgggc tccaaatggg agaagaggaa agggaaggcc   9060
caggatgatg gctctgcagc aacaccggag aacaaccagc ccagctagaa accagtagat   9120
tacctgactg tctggaaaac agttttgaaa atgatttgta gatttgttgt tgtttgattt   9180
gtagattttt aaggagagtt tgggaagaat taatgctaag gtcatagaac actaagctaa   9240
atgaatgaat gaatacatgc gtacagtttt ctaaaggaaa aaaaggtgaa catgtgaaaa   9300
ataaaaacac tgaatattga tgtaaccaga aattatgaca taatgtgcca cagtgtgtag   9360
cattatgtta gcataaaagt actaaatctt tatcttccat aataagaata gtaatataca   9420
attagggagc aaaaataaat ataaacatat tatttagaaa aatggaggca gacaccagga   9480
aaaacaccta gtgagaagag taagaagtta cctctaaaga gtagcactca atgtggggag   9540
ctagtagggc aaggatgtac ttttttgtgg ttgttgttgt tgttgagaca gggtcttact   9600
ctgtcaccca ggcaagagcg tagtggcatc atcatggccc attgcagcct cgacctccta   9660
ggctcaagca attcccccac ctcacccccc ctgagtagct gggaccacag gtgtgtgcca   9720
ctatgcctga ctaatttttt ccttcatttg tagagatggg gtctcgctat gttgcctagg   9780
ctggccttga actcctggtt tcaagtgatc ctcctgcctc agcttcccaa agtgctggga   9840
ttgcagacat gagccaccac aaccaacctg tactcttttc ttgttatgtt ttatagaact   9900
atttgacttt ttaaaaatca gacattttaa ttctttggat gtatttttct ttctaaagcg   9960
tctccttttc cactagatat ctacagttta atatcagggt tatttattat tgattgtaaa  10020
agtcttaaga gtgttagata tggtctcttc tcacctggct cagtgggcta taaacagagg  10080
gagaagggct cagatgtgga tgggtatagt tcctgggggt ctaggactat ggaggttttg  10140
cctttatatt tggaacccac cagaaaaatg aaggaaatta aatcccattt gttttccagc  10200
tcttccacat tgactttgga catattcttg gaaatttcaa atctaagttt ggcattaaaa  10260
gggagcgagt gccttttatt cttacctatg atttcatcca tgtcattcaa caaggaaaaa  10320
caggaaatac agaaaagttt ggccggtgag tactgccctt gtgccaaggc tgaacacttc  10380
taacattttc ttatctgacc aggtggacca gcatttctta gctgagatat atttggatct  10440
gggagatatt cagtctgatt ataggaagct tttgggggaa tttgcctgtc agattattgt  10500
gctggttcag aaattcccag ataggagaaa cagaatgcta gaaatttaaa atagttatta  10560
tattttattc caataatata ctacctttta cctgtttcag aacattctct gaaactatta  10620
agacagttga taggaagatg ctgaaaagac atctgctgtc attgtgtatg gagtacagta  10680
agggaactag aattcagggc aaattttttta atctctgatc tattactggc tacctacatg  10740
ttcccaagca taatacttgt ctttttgcct ttgtatcatc ttaaaatggg gacaaaaata  10800
tgaaattaag ggctactatg atggttagag acatatcatg taaccaacac atacttaaca  10860
aatcattgtc actatccttt atagttctgt ttgggtttct gcagaatata cctcagtggg  10920
```

```
tctagttttc tctttggcaa aataagggga tacgattgga tggtcctcag cctggcgcgg  10980
taggtcatgc ctgtaatctc agcactttgg gaggccaagg cacacagatc actggaggtc  11040
ggagtttgag accagcctga ccaacatggt gaaaccccgt ctctactaaa aatacaaaaa  11100
gtagccaggt gtggtggcac acgcctgtaa tctcagctac tcaggaggct gaggcagaat  11160
tgcttgaacc tggaaggcag aagttgcagt gagccaagat cacgccactg cactccagcc  11220
tgggagacag agcaaggttc catctcaaaa aaaaaacatt ggatgatctt cttgagggac  11280
catcttgaag aggagagaga gggaaggcag gatgacagga aggagcaaaa gcactgacac  11340
tgattgaggg gacttttaaa aaattagttt ctggaatcag accacaaata tagaacccag  11400
aagtatgttc agaaatcctt gtggattata attataactg atttaataat cagttcttgt  11460
gtctcataga attaaaaagt ctagattatt attaaaaatg taatagcctt tcgtcataga  11520
atttctattt agttttgttt ttgaaaaata tatctgtgat gttagagaga ttgattgttt  11580
tatgtagatt ttagtcctgg gacaattttc gcagaagtaa aaatcagaaa tgaaccttta  11640
gttcagtagg aattttctta ttctaataga aagtctagct gtgttttctt aatttcctgt  11700
atgaaatgtg ctctctcccc tctaacactg tgctcatgtg gtttgctgca tcacccaaag  11760
gttccgccag tgttgtgagg atgcatatct gattttacga cggcatggga atctcttcat  11820
cactctcttt gcgctgatgt tgactgcagg gcttcctgaa ctcacatcag tcaaagatat  11880
acagtatctt aaggtataaa accacttttc cttctctctt ggactttgtg ggcattgagc  11940
tcagttttag ctgcctgttt tattcaagtg gctgaaggaa gtagaacaaa gtcatttcct  12000
ctaagatggt tcttagccag gagggaaaga atctgggaag tacataaagg aggaattttg  12060
tagagtagct tgtaacccag aagattttcc catcagtaga aggggcgtaa agaagactgg  12120
tattgggctg tagccttctt actcacatta ctgaaagacc gcagatcagg agcgggttgc  12180
caccttgatt ttccacagtc tgcctttttc ttgccaggat cttagtaggt cttgagtcat  12240
cttactggat ttgggtggta gtggcaagca gctgtgcatc ctgcagtaat tataaattat  12300
tttcatcttc aaaaaccttt tggaagaagt catattatct ccctatcttg ggttctgcc   12360
tcctgcagat gatatttaaa taagaacatg aagcatgctg cctgatggtg gctggggagg  12420
cacaaccaat ccagcctcct gcagactttg atatttgcac atctctacta aagttatata  12480
aaatcatatt ttccccctc cattttagga ctctcttgca ttagggaaga gtgaagaaga   12540
agcactcaaa cagtttaagc aaaaatttga tgaggcgctc agggaaagct ggactactaa  12600
agtgaactgg atggcccaca cagttcggaa agactacaga tcttaacgat cagccttcgc  12660
tcctaatgta tttgttggtt tcatttcatt ttcattttgc acttgcacta aattgaacat  12720
gaccctgtta gagatgttat aaagggaatg aaatcctgga actcagagtt aaattaagaa  12780
caaggcatcc cacagaacct aatctgaaca atccccgatg attccctctg ctttttgaat  12840
gcttccaaga cttatcatga aaactgtcaa tggataatca tttcctgctg actttgcacg  12900
ccaaggaatg ctactaggga ttgtttccgt ttttgtttgt tttttctaat atttggtact  12960
tcccagaatg gtgtaaatac ttcttttcaa tgttgtgacc aagtattgtc actcagccaa  13020
caacttttcc acacctgggg gttggtggct gttcttactg tccaaatgaa gctaaaaaga  13080
aaggcatctt tcttcccttt taaaattgtg taaactgcaa attataatat aatttgaatt  13140
tatgattatt ttccagaaga aatcttgtaa acctgtggat actcattaat tcttttgtta  13200
atatttattt ccatgatagc atcattccag ccagacttgc tgaaaatcta ctggtgaggc  13260
aaatataata tatataaata tgctacatat atatttataa aatttctagt gggagttcta  13320
```

```
tataaatgtt tctttggtat tcttcagcct gtgatttaaa gttttacaaa aagcagagct  13380
ttttcctaag ttacttttca gttaggtaac tgtgtgatcc agttcttcca gctgcttcta  13440
taatgaggca catattaata cagtttttat atggtatcta tgaaagagtt cacttcatag  13500
agaataatac ttgagcaaat gtatccaaga aagcaagcaa atgaaaagaa acctatttat  13560
ggaataaact ccagatctga aattcagtat tttagaaaaa tgccagctct tcttactgta  13620
tttattaaaa cttgtaataa tgtgattttt ttcaaggata ttagttcaaa ttgaaatggt  13680
ttcacgccac acggaaatct ttaagttatt tgttgaggta ccatatattt agggtgctag  13740
gggcaagtaa tgttaatatg tgcaatagga actactggtt tgaatgtgta aatgggtgat  13800
ctctctgagt cctggcaaca tccagcaaaa ctactgctta ttctccaaag aatattggga  13860
gctctcaatc ctcggtgata tgggaaagag aactgagtat ttgccctatg actgagcttt  13920
ctataggaat tttattaaag aatgtttaat tttgttgtcc ttcttaatgt tctcagtcaa  13980
ataaatgagt gagctggttt cggctgctct tggaatgggt gagcctcttc tttatgggta  14040
gactgggcct ttggaacttg gcactggaac tccaagaaat ggccaagtca gtagacaaac  14100
caacctcagg aataggctaa ggcttattat ggcctcttcc ctgacttctc cccttgtttc  14160
ccagcctcat caggcatggt ataggaggcc ccctggactt tggtgggagc ctgaggtaag  14220
gagccatgca tatgggaggt gtcctgaagt ctgggtagtt acttggcact gagccaaggc  14280
cagactctgc tgctttggag ctcttgttca tggggcagat gctggagcag tccagttcct  14340
tggaaataac tcagctgagg atgggagttg gcccctgaat tcctcatttc cagggctggt  14400
gtagactcac tgagacttcc aggaatagaa ctatggaagg acaggtttgt tcagagatct  14460
ttgtctagta gccacccacc atttcatgaa ccaggccgca ggtcagtggt ttggagaatg  14520
gtgaacactg ccaggaagaa atggatacca ttctttccag aggggtctcc tcagccaaaa  14580
ggagggcctt gataaataca tgccaaatca gtgaagttca agtcaactgt ttttcccata  14640
tgggcaccaa attgtatctt tcctgttttc tttgaagggt taagtaacgt gaccatagtc  14700
acagagtagt tgatggagcc agtattcaaa cccagaaagt aagaagccta ttttaattat  14760
ctgtgctctt tactcacaat gcctcagtat acatttcaga tttattgggt tccacaaata  14820
gaaacctatg gaaattttga atcaaattgc attaagctat agacaaggtt gagacaaatt  14880
gacatctcca gaatattgag ttttccaaaa tatgtaagtg gagtacccat ttatttagat  14940
tatctttcat ttatatccgc aatgatttat agtattctgt gtttacatat tatgcatcgt  15000
ttgttagatt cctgggtaag tgacttttatt gtaagtttca ttgttgttaa tctatagcaa  15060
tcattctcca agtgtggtcc cctgatgagg agcatcagca tcaccagaga gaactggtta  15120
aaaatgcaaa ttcttaattt ttaatttttg tgagtacata gtagatatat atatgggata  15180
catggaatat tttgatacag gcatataaca tgtaattatc gcatcagggt aattggggta  15240
tccattacct caagcattta tcctttgtat tagaaacaat ccagttatac tcttttagtt  15300
attttaagat ctataattaa attatcgact atagttactc tgttgtgcta tcaaatacta  15360
gatcttattc attcttacta tttttttgt acccatagaa atgcagattc ttggtggggc  15420
ctggcagctc acacctgtaa tcccagcatt ttgggagggc gaggccgggg aatcacctga  15480
ggtcaggagt tcaagattag cctggccaac atggtgaaac ctgtatctac taaaaacaca  15540
aaaattagct gggcatggtg gctggctcct gtaatcccag ctactcgaaa ggctgaggta  15600
ggagaatcac ttgaacccag gaggcggagg ttgcagtagc cgagatcaca ccactgcact  15660
ccagcctggg taacagagtg agactccatc tcaaaaaaag aaaaaaaaaa gaaatgcaca  15720
```

tccttgagcc ctgccctgga gctactgatt tagaaatggg ggtggagccc caaacctgta 15780
tttaatttaa tttatttatt tatttatttt ttgagatgga gtctcgcttt gttgcccagg 15840
ctggagtgca gtggtgtgat ctcgattcac ttcaacctcc acctcccagg ttcaagcaat 15900
tatgtctcaa cctcccgagt ttagctggga ctacaggtat gcaccaccat gtccagctaa 15960
tttttgtatt tttaataaag acagggtttc accatattgg tcaggctggt ctcgaactcc 16020
tgacctcagg tgatccacct acctcaacct cccaaagtgc tgggattata ggcatgagcc 16080
accgcaccca gccaaacctg tattttcata aagttccaga gcaaaggtcc acaaatacat 16140
ttgatgtttg tatttagcag acttataaac tttctaatta atcctaacaa tttatttgta 16200
tgaatttttt tttttttttc ttgagacagg gtctcactat gtcacccagg ctggagtgca 16260
gtggcgtact ctcggctcac tgcaacctct gtctcctggg cttaggtggt cctccgacct 16320
cagcctcctg aatagctggg gccacaggca tgcaccacca cacgcagcta atttttgttt 16380
gtttgtttgt ttgttttaag agacggaggt ttaccatgtt gcccaggttg gcctcaaact 16440
tctggactca agcagtctg 16459

<210> SEQ ID NO 87
<211> LENGTH: 1145
<212> TYPE: DNA
<213> ORGANISM: Homo sapiens

<400> SEQUENCE: 87
attctctccc cagcttgctg agccctttgc tcccctggcg actgcctgga cagtcagcaa 60
ggaattgtct cccagtgcat tttgccctcc tggctgccaa ctctggctgc taaagcggct 120
gccacctgct gcagtctaca cagcttcggg aagaggaaag gaacctcaga ccttccagat 180
cgcttcctct cgcaacaaac tatttgtcgc aggaataaag atggctgctg aaccagtaga 240
agacaattgc atcaactttg tggcaatgaa atttattgac aatacgcttt actttatagc 300
tgaagatgat gaaaacctgg aatcagatta ctttggcaag cttgaatcta aattatcagt 360
cataagaaat ttgaatgacc aagttctctt cattgaccaa ggaaatcggc ctctatttga 420
agatatgact gattctgact gtagagataa tgcaccccgg accatattta ttataagtat 480
gtataaagat agccagccta gaggtatggc tgtaactatc tctgtgaagt gtgagaaaat 540
ttcaactctc tcctgtgaga acaaaattat ttcctttaag gaaatgaatc ctcctgataa 600
catcaaggat acaaaaagtg acatcatatt ctttcagaga agtgtcccag gacatgataa 660
taagatgcaa tttgaatctt catcatacga aggatacttt ctagcttgtg aaaaagagag 720
agaccttttt aaactcattt tgaaaaaaga ggatgaattg gggggatagat ctataatgtt 780 cactgttcaa aacgaagact agctattaaa atttcatgcc gggcgcagtg gctcacgcct 840
gtaatcccag ccctttggga ggctgaggcg ggcagatcac cagaggtcag gtgttcaaga 900
ccagcctgac caacatggtg aaacctcatc tctactaaaa atacaaaaaa ttagctgagt 960
gtagtgacgc atgccctcaa tcccagctac tcaagaggct gaggcaggag aatcacttgc 1020
actccggagg tagaggttgt ggtgagccga gattgcacca ttgcgctcta gcctgggcaa 1080
caacagcaaa actccatctc aaaaaataaa ataaataaat aaacaaataa aaaattcata 1140
atgtg 1145

<210> SEQ ID NO 88
<211> LENGTH: 732
<212> TYPE: DNA
<213> ORGANISM: Homo sapiens

<400> SEQUENCE: 88

```
tttttttttt ttttttttgg acacagggtc ttgctgttgc ccaggctgga gtgcagtggc     60

atgaccatag ctcactgcag ccttgacttc cttaactcaa gcaatcctct tgcctcagcc    120

tcctgtagca ctgtaggcac acacaactat gcctggctaa ttttaacatt tttctttcac    180

cttcttgacc cttatcttct atacccggct aatttttttgt agagacagtg tcttgctatg    240

ttgtccaagc tggtcttgaa ttcctcgcct caagcaatcc ttccacctca gcttcctgag    300

tgttaggatt acaggcatga gccactgcac ctggcctcca acaggtaatt ttagaacatt    360

tttccctcta cactaattac cctcctataa cctccattgg ttatcactta ctttctgatg    420

ttgtattcat agagcatgaa tatcttagaa agatggcacc atccttctat taataagacc    480

agcagaatag ctcagtttaa agttcctcta aacccaagaa aatatcaaac aaaaatgtct    540

tttttagat aaatttgaag tcagaagata ttttgatatg agtctagtca tctcttggta    600

tccatggggg attggttcct gaaacccttg gataccaaaa tccacagaag gatgctcaag    660

tctctgtaaa atagcatagt atttatatat agcctatgca catttcccca tacactttag    720

attactctag at                                                        732
```

<210> SEQ ID NO 89
<211> LENGTH: 2914
<212> TYPE: DNA
<213> ORGANISM: Homo sapiens

<400> SEQUENCE: 89

```
gtgctctgag tttttggttt ctgtttcacc ttgtgtctga gctggtctga aggctggttg     60

ttcagactga gcttcctgcc tgcctgtacc ccgccaacag cttcagaaga aggtgactgg    120

tggctgcctg aggaatacca gtgggcaaga gaattagcat ttctggagca tctgctgtct    180

gagcagcccc tgggtgcgtc cactttctgg gcacgtgagg ttgggccttg gccgcctgag    240

cccttgagtt ggtcacttga accttgggaa tattgagatt atattctcct gccttttaaa    300

aagatggact tcagcagaaa tctttatgat attggggaac aactggacag tgaagatctg    360

gcctccctca agttcctgag cctggactac attccgcaaa ggaagcaaga acccatcaag    420

gatgccttga tgttattcca gagactccag gaaaagagaa tgttggagga aagcaatctg    480

tccttcctga aggagctgct cttccgaatt aatagactgg atttgctgat tacctaccta    540

aacactagaa aggaggagat ggaaagggaa cttcagacac caggcagggc tcaaatttct    600

gcctacaggt tccacttctg ccgcatgagc tgggctgaag caaacagcca gtgccagaca    660

cagtctgtac ctttctggcg gagggtcgat catctattaa taagggtcat gctctatcag    720

atttcagaag aagtgagcag atcagaattg aggtctttta agtttctttt gcaagaggaa    780

atctccaaat gcaaactgga tgatgacatg aacctgctgg atattttcat agagatggag    840

aagagggtca tcctgggaga aggaaagttg gacatcctga aaagagtctg tgcccaaatc    900

aacaagagcc tgctgaagat aatcaacgac tatgaagaat tcagcaaagg ggaggagttg    960

tgtggggtaa tgacaatctc ggactctcca agagaacagg atagtgaatc acagactttg   1020

gacaaagttt accaaatgaa aagcaaacct cggggatact gtctgatcat caacaatcac   1080

aattttgcaa aagcacggga gaaagtgccc aaacttcaca gcattaggga caggaatgga   1140

acacacttgg atgcaggggc tttgaccacg acctttgaag agcttcattt tgagatcaag   1200

ccccacgatg actgcacagt agagcaaatc tatgagattt tgaaaatcta ccaactcatg   1260

gaccacagta acatggactg cttcatctgc tgtatcctct cccatggaga caagggcatc   1320
```

```
atctatggca ctgatggaca ggaggccccc atctatgagc tgacatctca gttcactggt   1380

ttgaagtgcc cttcccttgc tggaaaaccc aaagtgtttt ttattcaggc ttgtcagggg   1440

gataactacc agaaaggtat acctgttgag actgattcag aggagcaacc ctatttagaa   1500

atggatttat catcacctca aacgagatat atcccggatg aggctgactt tctgctgggg   1560

atggccactg tgaataactg tgtttcctac cgaaaccctg cagagggaac ctggtacatc   1620

cagtcacttt gccagagcct gagagagcga tgtcctcgag gcgatgatat tctcaccatc   1680

ctgactgaag tgaactatga agtaagcaac aaggatgaca agaaaaacat ggggaaacag   1740

atgcctcagc ctactttcac actaagaaaa aaacttgtct tcccttctga ttgatggtgc   1800

tattttgttt gttttgtttt gttttgtttt tttgagacag aatctcgctc tgtcgcccag   1860

gctggagtgc agtggcgtga tctcggctca ccgcaagctc cgcctcccgg gttcaggcca   1920

ttctcctgcc tcagcctccc gagtagctgg gactacaggg gcccgccacc acacctggct   1980

aattttttaa aaatattttt agtagagaca gggtttcact gtgttagcca gggtggtctt   2040

gatctcctga cctcgtgatc cacccacctc ggcctcccaa agtgctggga ttacaggcgt   2100

gagccaccgc gcctggccga tggtactatt tagatataac actatgttta tttactaatt   2160

ttctagattt tctactttat taattgtttt gcactttttt ataagagcta aagttaaata   2220

ggatattaac aacaataaca ctgtctcctt tctcttatgc ttaaggcttt gggaatgttt   2280

ttagctggtg gcaataaata ccagacacgt acaaaatcca gctatgaata tagagggctt   2340

atgattcaga ttgttatcta tcaactataa gcccactgtt aatattctat taactttaat   2400

tctctttcaa agctaaattc cacactacca cattaaaaaa attagaaagt agccacgtat   2460

ggtggctcat gtctataatc ccagcacttt gggaggttga ggtgggagga ttgcttgaac   2520

ccaagaggtc aaggctgcag tgagccatgt tcacaccgct gcactcaagc ttgggtgaca   2580

gaacaagacc ccgtctcaaa aaaaattttt tttttaataa aacaaaattt gtttgaaatc   2640

ttttaaaaat tcaaatgatt tttacaagtt ttaaataagc tctccccaaa cttgctttat   2700

gccttcttat tgcttttatg atatatatat gcttggctaa ctatatttgc tttttgctaa   2760

caatgctctg ggtctttttt atgcatttgc atttgctctt tcatctctgc ttggattatt   2820

ttaaatcatt aggaattaag ttatctttaa aatttaagta tcttttttca aaaacatttt   2880

ttaatagaat aaaatataat ttgatcttat taaa                               2914
```

<210> SEQ ID NO 90
<211> LENGTH: 2153
<212> TYPE: DNA
<213> ORGANISM: Homo sapiens

<400> SEQUENCE: 90

```
aagactgcga gctccccgca ccccctcgca ctccctctgg ccggcccagg gcgccttcag     60

cccaacctcc ccagccccac gggcgccacg gaacccgctc gatctcgccg ccaactggta    120

gacatggaga cccctgcctg gccccgggtc ccgcgccccg agaccgccgt cgctcggacg    180

ctcctgctcg gctgggtctt cgcccaggtg gccggcgctt caggcactac aaatactgtg    240

gcagcatata atttaacttg gaaatcaact aatttcaaga caattttgga gtgggaaccc    300

aaacccgtca atcaagtcta cactgttcaa ataagcacta agtcaggaga ttggaaaagc    360

aaatgctttt acacaacaga cacagagtgt gacctcaccg acgagattgt gaaggatgtg    420

aagcagacgt acttggcacg ggtcttctcc tacccggcag ggaatgtgga gagcaccggt    480

tctgctgggg agcctctgta tgagaactcc ccagagttca caccttacct ggagacaaac    540
```

```
ctcggacagc caacaattca gagttttgaa caggtgggaa caaaagtgaa tgtgaccgta    600

gaagatgaac ggactttagt cagaaggaac aacactttcc taagcctccg ggatgttttt    660

ggcaaggact taatttatac actttattat tggaaatctt caagttcagg aaagaaaaca    720

gccaaaacaa acactaatga gtttttgatt gatgtggata aaggagaaaa ctactgtttc    780

agtgttcaag cagtgattcc ctcccgaaca gttaaccgga agagtacaga cagcccggta    840

gagtgtatgg gccaggagaa aggggaattc agagaaatat tctacatcat tggagctgtg    900

gtatttgtgg tcatcatcct tgtcatcatc ctggctatat ctctacacaa gtgtagaaag    960

gcaggagtgg ggcagagctg gaaggagaac tccccactga atgtttcata aaggaagcac   1020

tgttggagct actgcaaatg ctatattgca ctgtgaccga gaacttttaa gaggatagaa   1080

tacatggaaa cgcaaatgag tatttcggag catgaagacc ctggagttca aaaaactctt   1140

gatatgacct gttattacca ttagcattct ggttttgaca tcagcattag tcactttgaa   1200

atgtaacgaa tggtactaca accaattcca agttttaatt tttaacacca tggcaccttt   1260

tgcacataac atgctttaga ttatatattc cgcacttaag gattaaccag gtcgtccaag   1320

caaaaacaaa tgggaaaatg tcttaaaaaa tcctgggtgg acttttgaaa agcttttttt   1380

tttttttttt tttgagacgg agtcttgctc tgttgcccag gctggagtgc agtagcacga   1440

tctcggctca cttgcaccct ccgtctctcg ggttcaagca attgtctgcc tcagcctccc   1500

gagtagctgg gattacaggt gcgcactacc acgccaagct aatttttgta tttttttagta   1560

gagatggggt ttcaccatct tggccaggct ggtcttgaat tcctgacctc agtgatccac   1620

ccaccttggc ctcccaaaga tgctagtatt atgggcgtga accaccatgc ccagccgaaa   1680

agcttttgag gggctgactt caatccatgt aggaaagtaa aatggaagga aattgggtgc   1740

atttctagga cttttctaac atatgtctat aatatagtgt ttaggttctt tttttttttca   1800

ggaatacatt tggaaattca aaacaattgg gcaaactttg tattaatgtg ttaagtgcag   1860

gagacattgg tattctgggc agcttcctaa tatgctttac aatctgcact ttaactgact   1920

taagtggcat taaacatttg agagctaact atatttttat aagactacta tacaaactac   1980

agagtttatg atttaaggta cttaaagctt ctatggttga cattgtatat ataatttttt   2040

aaaaaggttt ttctatatgg ggattttcta tttatgtagg taatattgtt ctatttgtat   2100

atattgagat aatttattta atatacttta aataaaggtg actgggaatt gtt          2153
```

<210> SEQ ID NO 91
<211> LENGTH: 5133
<212> TYPE: DNA
<213> ORGANISM: Homo sapiens

<400> SEQUENCE: 91

```
cctctttcac cctgtctagg ttgccagcaa atcccacggg cctcctgacg ctgcccctgg     60

ggccacaggt ccctcgagtg ctggaaggat gaaggattcc tgcatcactg tgatggccat    120

ggcgctgctg tctgggttct tttcttcgc gccggcctcg agctacaacc tggacgtgcg    180

gggcgcgcgg agcttctccc caccgcgcgc cgggaggcac tttggatacc gcgtcctgca    240

ggtcggaaac ggggtcatcg tgggagctcc aggggagggg aacagcacag gaagcctcta    300

tcagtgccag tcgggcacag gacactgcct gccagtcacc ctgagaggtt ccaactatac    360

ctccaagtac ttgggaatga ccttggcaac agaccccaca gatggaagca ttttggcctg    420

tgaccctggg ctgtctcgaa cgtgtgacca gaacacctat ctgagtggcc tgtgttacct    480

cttccgccag aatctgcagg gtcccatgct gcaggggcgc cctggttttc aggaatgtat    540
```

```
caagggcaac gtagacctgg tatttctgtt tgatggttcg atgagcttgc agccagatga    600
atttcagaaa attctggact tcatgaagga tgtgatgaag aaactcagca acacttcgta    660
ccagtttgct gctgttcagt tttccacaag ctacaaaaca gaatttgatt tctcagatta    720
tgttaaatgg aaggaccctg atgctctgct gaagcatgta aagcacatgt tgctgttgac    780
caataccttt ggtgccatca attatgtcgc gacagaggtg ttccgggagg agctgggggc    840
ccggccagat gccaccaaag tgcttatcat catcacggat ggggaggcca ctgacagtgg    900
caacatcgat gcggccaaag acatcatccg ctacatcatc gggattggaa agcattttca    960
gaccaaggag agtcaggaga ccctccacaa atttgcatca aaacccgcga gcgagtttgt   1020
gaaaattctg gacacatttg agaagctgaa agatctattc actgagctgc agaagaagat   1080
ctatgtcatt gagggcacaa gcaaacagga cctgacttcc ttcaacatgg agctgtcctc   1140
cagcggcatc agtgctgacc tcagcagggg ccatgcagtc gtgggggcag taggagccaa   1200
ggactgggct gggggctttc ttgacctgaa ggcagacctg caggatgaca catttattgg   1260
gaatgaacca ttgacaccag aagtgagagc aggctatttg ggttacaccg tgacctggct   1320
gccctcccgg caaaagactt cgttgctggc ctcgggagcc cctcgatacc agcacatggg   1380
ccgagtgctg ctgttccaag agccacaggg cggaggacac tggagccagg tccagacaat   1440
ccatgggacc cagattggct cttatttcgg tggggagctg tgtggcgtcg acgtggacca   1500
agatggggag acagagctgc tgctgattgg tgccccactg ttctatgggg agcagagagg   1560
aggccgggtg tttatctacc agagaagaca gttggggttt gaagaagtct cagagctgca   1620
gggggacccc ggctacccac tcgggcggtt tggagaagcc atcactgctc tgacagacat   1680
caacggcgat gggctggtag acgtggctgt gggggcccct ctggaggagc agggggctgt   1740
gtacatcttc aatgggaggc acggggggct tagtccccag ccaagtcagc ggatagaagg   1800
gacccaagtg ctctcaggaa ttcagtggtt tggacgctcc atccatgggg tgaaggacct   1860
tgaaggggat ggcttggcag atgtggctgt gggggctgag agccagatga tcgtgctgag   1920
ctcccggccc gtggtggata tggtcaccct gatgtccttc tctccagctg agatcccagt   1980
gcatgaagtg gagtgctcct attcaaccag taacaagatg aaagaaggag ttaatatcac   2040
aatctgtttc cagatcaagt ctctctaccc ccagttccaa ggccgcctgg ttgccaatct   2100
cacttacact ctgcagctgg atggccaccg gaccagaaga cgggggttgt tcccaggagg   2160
gagacatgaa ctcagaagga atatagctgt caccaccagc atgtcatgca ctgacttctc   2220
atttcatttc ccggtatgtg ttcaagacct catctccccc atcaatgttt ccctgaattt   2280
ctctctttgg gaggaggaag ggacaccgag ggaccaaagg gcgcagggca aggacatacc   2340
gcccatcctg agaccctccc tgcactcgga aacctgggag atccctttttg agaagaactg   2400
tggggaggac aagaagtgtg aggcaaactt gagagtgtcc ttctctcctg caagatccag   2460
agccctgcgt ctaactgctt ttgccagcct ctctgtggag ctgagcctga gtaacttgga   2520
agaagatgct tactgggtcc agctggacct gcacttcccc ccgggactct ccttccgcaa   2580
ggtggagatg ctgaagcccc atagccagat acctgtgagc tgcgaggagc ttcctgaaga   2640
gtccaggctt ctgtccaggg cattatcttg caatgtgagc tctcccatct tcaaagcagg   2700
ccactcggtt gctctgcaga tgatgtttaa tacactggta aacagctcct ggggggactc   2760
ggttgaattg cacgccaatg tgacctgtaa caatgaggac tcagacctcc tggaggacaa   2820
ctcagccact accatcatcc ccatcctgta ccccatcaac atcctcatcc aggaccaaga   2880
agactccaca ctctatgtca gtttcacccc caaaggcccc aagatccacc aagtcaagca   2940
```

```
catgtaccag gtgaggatcc agccttccat ccacgaccac aacataccca ccctggaggc   3000

tgtggttggg gtgccacagc ctcccagcga ggggcccatc acacaccagt ggagcgtgca   3060

gatggagcct cccgtgccct gccactatga ggatctggag aggctcccgg atgcagctga   3120

gccttgtctc cccggagccc tgttccgctg ccctgttgtc ttcaggcagg agatcctcgt   3180

ccaagtgatc gggactctgg agctggtggg agagatcgag gcctcttcca tgttcagcct   3240

ctgcagctcc ctctccatct ccttcaacag cagcaagcat ttccacctct atggcagcaa   3300

cgcctccctg gcccaggttg tcatgaaggt tgacgtggtg tatgagaagc agatgctcta   3360

cctctacgtg ctgagcggca tcggggggct gctgctgctg ctgctcattt tcatagtgct   3420

gtacaaggtt ggtttcttca aacggaacct gaaggagaag atggaggctg gcagaggtgt   3480

cccgaatgga atccctgcag aagactctga gcagctggca tctgggcaag aggctgggga   3540

tcccggctgc ctgaagcccc tccatgagaa ggactctgag agtggtggtg gcaaggactg   3600

agtccaggcc tgtgaggtgc agagtgccca gaactggact caggatgccc agggccactc   3660

tgcctctgcc tgcattctgc cgtgtgccct cgggcgagtc actgcctctc cctggccctc   3720

agtttcccta tctcgaacat ggaactcatt cctgaatgtc tcctttgcag gctcataggg   3780

aagacctgct gagggaccag ccaagagggc tgcaaaagtg agggcttgtc attaccagac   3840

ggttcaccag cctctcttgg ttccttcctt ggaagagaat gtctgatcta aatgtggaga   3900

aactgtagtc tcaggaccta gggatgttct ggccctcacc cctgccctgg gatgtccaca   3960

gatgcctcca ccccccagaa cctgtccttg cacactcccc tgcactggag tccagtctct   4020

tctgctggca gaaagcaaat gtgacctgtg tcactacgtg actgtggcac acgccttgtt   4080

cttggccaaa gaccaaattc cttggcatgc cttccagcac cctgcaaaat gagaccctcg   4140

tggccttccc cagcctcttc tagagccgtg atgcctccct gttgaagctc tggtgacacc   4200

agcctttctc ccaggccagg ctccttcctg tcttcctgca ttcacccaga cagctccctc   4260

tgcctgaacc ttccatctcg cccacccctc cttccttgac cagcagatcc cagctcacgt   4320

cacacacttg gttgggtcct cacatctttc acacttccac caccctgcac tactccctca   4380

aagcacacgt catgtttctt catccggcag cctggatgtt ttttccctgt ttaatgattg   4440

acgtacttag cagctatctc tcagtgaact gtgagggtaa aggctatact tgtcttgttc   4500

accttgggat gacgccgcat gatatgtcag ggcgtgggac atctagtagg tgcttgacat   4560

aatttcactg aattaatgac agagccagtg ggaagataca gaaaaagagg gccggggctg   4620

ggcgcggtgg ttcacgcctg taatcccagc actttgggag gccaaggagg gtggatcacc   4680

tgaggtcagg agttagaggc cagcctggcg aaaccccatc tctactaaaa atacaaaatc   4740

caggcgtggt ggcacacacc tgtagtccca gctactcagg aggttgaggt aggagaattg   4800

cttgaacctg ggaggtggag gttgcagtga gccaagattg cgccattgca ctccagcctg   4860

ggcaacacag cgagactccg tctcaaggaa aaaataaaaa taaaaagcgg gcacgggccc   4920

ggacatcccc acccttggag gctgtcttct caggctctgc cctgccctag ctccacaccc   4980

tctcccagga cccatcacgc ctgtgcagtg gcccccacag aaagactgag ctcaaggtgg   5040

gaaccacgtc tgctaacttg gagccccagt gccaagcaca gtgcctgcat gtatttatcc   5100

aataaatgtg aaattctgtc caaaaaaaaa aaa                                5133
```

<210> SEQ ID NO 92
<211> LENGTH: 2357
<212> TYPE: DNA
<213> ORGANISM: Homo sapiens

<400> SEQUENCE: 92

```
cgagcttggc tgcttctggg gcctgtgtgg ccctgtgtgt cggaaagatg gagcaagaag     60
ccgagcccga ggggcggccg cgacccctct gaccgagatc ctgctgcttt cgcagccagg    120
agcaccgtcc ctccccggat tagtgcgtac gagcgcccag tgccctggcc cggagagtgg    180
aatgatcccc gaggcccagg gcgtcgtgct tccgcgcgcc ccgtgaagga aactggggag    240
tcttgaggga cccccgactc caagcgcgaa aaccccggat ggtgaggagc aggcaaatgt    300
gcaataccaa catgtctgta cctactgatg gtgctgtaac cacctcacag attccagctt    360
cggaacaaga gaccctggtt agaccaaagc cattgctttt gaagttatta aagtctgttg    420
gtgcacaaaa agacacttat actatgaaag aggttctttt ttatcttggc cagtatatta    480
tgactaaacg attatatgat gagaagcaac aacatattgt atattgttca aatgatcttc    540
taggagattt gtttggcgtg ccaagcttct ctgtgaaaga gcacaggaaa atatatacca    600
tgatctacag gaacttggta gtagtcaatc agcaggaatc atcggactca ggtacatctg    660
tgagtgagaa caggtgtcac cttgaaggtg ggagtgatca aaaggacctt gtacaagagc    720
ttcaggaaga gaaaccttca tcttcacatt tggtttctag accatctacc tcatctagaa    780
ggagagcaat tagtgagaca gaagaaaatt cagatgaatt atctggtgaa cgacaaagaa    840
aacgccacaa atctgatagt atttcccttt cctttgatga aagcctggct ctgtgtgtaa    900
taagggagat atgttgtgaa agaagcagta gcagtgaatc tacagggacg ccatcgaatc    960
cggatcttga tgctggtgta agtgaacatt caggtgattg gttggatcag gattcagttt   1020
cagatcagtt tagtgtagaa tttgaagttg aatctctcga ctcagaagat tatagcctta   1080
gtgaagaagg acaagaactc tcagatgaag atgatgaggt atatcaagtt actgtgtatc   1140
aggcagggga gagtgataca gattcatttg aagaagatcc tgaaatttcc ttagctgact   1200
attggaaatg cacttcatgc aatgaaatga atcccccccct tccatcacat tgcaacagat   1260
gttgggccct tcgtgagaat tggcttcctg aagataaagg gaaagataaa ggggaaatct   1320
ctgagaaagc caaactggaa aactcaacac aagctgaaga gggctttgat gttcctgatt   1380
gtaaaaaaac tatagtgaat gattccagag agtcatgtgt tgaggaaaat gatgataaaa   1440
ttacacaagc ttcacaatca caagaaagtg aagactattc tcagccatca acttctagta   1500
gcattattta tagcagccaa gaagatgtga aagagtttga aagggaagaa acccaagaca   1560
aagaagagag tgtggaatct agtttgcccc ttaatgccat tgaaccttgt gtgatttgtc   1620
aaggtcgacc taaaaatggt tgcattgtcc atggcaaaac aggacatctt atggcctgct   1680
ttacatgtgc aaagaagcta aagaaaagga ataagccctg cccagtatgt agacaaccaa   1740
ttcaaatgat tgtgctaact tatttcccct agttgacctg tctataagag aattatatat   1800
ttctaactat ataaccctag gaatttagac aacctgaaat ttattcacat atatcaaagt   1860
gagaaaatgc ctcaattcac atagatttct tctctttagt ataattgacc tactttggta   1920
gtggaatagt gaatacttac tataatttga cttgaatatg tagctcatcc tttacaccaa   1980
ctcctaattt taaataattt ctactctgtc ttaaatgaga agtacttggt tttttttttt   2040
cttaaatatg tatatgacat ttaaatgtaa cttattattt tttttgagac cgagtcttgc   2100
tctgttaccc aggctggagt gcagtggcgt gatcttggct cactgcaagc tctgcctccc   2160
gggttcgcac cattctcctg cctcagcctc ccaattagct tggcctacag tcatctgcca   2220
ccacacctgg ctaatttttt gtacttttag tagagacagg gtttcaccgt gttagccagg   2280
atggtctcga tctcctgacc tcgtgatccg cccacctcgg cctcccaaag tgctgggatt   2340
```

acaggcatga gccaccg 2357

<210> SEQ ID NO 93
<211> LENGTH: 4034
<212> TYPE: DNA
<213> ORGANISM: Homo sapiens

<400> SEQUENCE: 93
agggagaggc agagaggcag gcagcctgct gggctcttcc tgctgttgaa aacttacccg 60
gcccttacag aggaaatctt cctcctctct tctgccctga atgttttccc aaacatgaag 120
gtgataagct tattcatttt ggtgggattt ataggagagt tccaaagttt ttcaagtgcc 180
tcctctccag tcaactgcca gtgggacttc tatgcccctt ggtcagaatg caatggctgt 240
accaagactc agactcgcag gcggtcagtt gctgtgtatg ggcagtatgg aggccagcct 300
tgtgttggaa atgcttttga aacacagtcc tgtgaaccta caagaggatg tccaacagag 360
gagggatgtg gagagcgttt caggtgcttt tcaggtcagt gcatcagcaa atcattggtt 420
tgcaatgggg attctgactg tgatgaagac agtgctgatg aagacagatg tgaggactca 480
gaaaggagac cttcctgtga tatcgataaa cctcctccta acatagaact tactggaaat 540
ggttacaatg aactcactgg ccagtttagg aacagagtca tcaataccaa aagttttggt 600
ggtcaatgta gaaaggtgtt tagtggggat ggaaaagatt tctacaggct gagtggaaat 660
gtcctgtcct atacattcca ggtgaaaata aataatgatt ttaattatga attttacaat 720
agtacttggt cttatgtaaa acatacgtcg acagaacaca catcatctag tcggaagcgc 780
tcctttttta gatcttcatc atcttcttca cgcagttata cttcacatac caatgaaatc 840
cataaaggaa agagttacca actgctggtt gttgagaaca ctgttgaagt ggctcagttc 900
attaataaca atccagaatt tttacaactt gctgagccat tctggaagga gctttcccac 960
ctcccctctc tgtatgacta cagtgcctac cgaagattaa tcgaccagta cgggacacat 1020
tatctgcaat ctgggtcgtt aggaggagaa tacagagttc tattttatgt ggactcagaa 1080
aaattaaaac aaaatgattt taattcagtc gaagaaaaga aatgtaaatc ctcaggttgg 1140
cattttgtcg ttaaattttc aagtcatgga tgcaaggaac tggaaaacgc tttaaaagct 1200
gcttcaggaa cccagaacaa tgtattgcga ggagaaccgt tcatcagagg gggaggtgca 1260
ggcttcatat ctggccttag ttacctagag ctggacaatc ctgctggaaa caaaaggcga 1320
tattctgcct gggcagaatc tgtgactaat cttcctcaag tcataaaaca aaagctgaca 1380
cctttatatg agctggtaaa ggaagtacct tgtgcctctg tgaaaaaact atacctgaaa 1440
tgggctcttg aagagtatct ggatgaattt gacccctgtc attgccggcc ttgtcaaaat 1500
ggtggtttgg ctactgttga ggggacccat tgtctgtgcc attgcaaacc gtacacattt 1560
ggtgcggcgt gtgagcaagg agtcctcgta gggaatcaag caggaggggt tgatggaggt 1620
tggagttgct ggtcctcttg gagcccctgt gtccaaggga agaaaacaag aagccgtgaa 1680
tgcaataacc cacctcccag tgggggtggg agatcctgcg ttggagaaac gacagaaagc 1740
acacaatgcg aagatgagga gctggagcac ttgaggttgc ttgaaccaca ttgctttcct 1800
ttgtctttgg ttccaacaga attctgtcca tcacctcctg ccttgaaaga tggatttgtt 1860
caagatgaag gtacaatgtt tcctgtgggg aaaaatgtag tgtacacttg caatgaagga 1920
tactctctta ttggaaaccc agtggccaga tgtggagaag atttacggtg gcttgttggg 1980
gaaatgcatt gtcagaaaat tgcctgtgtt ctacctgtac tgatggatgg catacagagt 2040
cacccccaaa aacctttcta cacagttggt gagaaggtga ctgtttcctg ttcaggtggc 2100

```
atgtccttag aaggtccttc agcatttctc tgtggctcca gccttaagtg gagtcctgag   2160

atgaagaatg cccgctgtgt acaaaaagaa aatccgttaa cacaggcagt gcctaaatgt   2220

cagcgctggg agaaactgca gaattcaaga tgtgtttgta aaatgcccta cgaatgtgga   2280

ccttccttgg atgtatgtgc tcaagatgag agaagcaaaa ggatactgcc tctgacagtt   2340

tgcaagatgc atgttctcca ctgtcagggt agaaattaca cccttactgg tagggacagc   2400

tgtactctgc ctgcctcagc tgagaaagct tgtggtgcct gcccactgtg gggaaaatgt   2460

gatgctgaga gcagcaaatg tgtctgccga gaagcatcgg agtgcgagga agaagggttt   2520

agcatttgtg tggaagtgaa cggcaaggag cagacgatgt ctgagtgtga ggcgggcgct   2580

ctgagatgca gagggcagag catctctgtc accagcataa ggccttgtgc tgcggaaacc   2640

cagtaggctc ctggaggccc tggtcagctt gcttggaatc cagcaggcag ctggggctga   2700

gtgaaaacat ctgcacaact gggcactgga cagcttttcc ttcttctcca gtgtctacct   2760

tcctcctcaa ctcccagcca tctgtataaa cacaatcctt tgttctccca aatctgaatc   2820

gaattactct tttgcctcct ttttaatgtc agtaaggata tgagcctttg cacaggctgg   2880

ctgcgtgttc ttgaaatagg tgttaccttc tctgggcctt ggttttttaa aatctgtaaa   2940

attagaggat tgcactagag aaacttgaat gctccattca ggcctatcat tttattaagt   3000

atgattgaca cagcccatgg gccagaacac actctacaaa atgactagga taacagaaag   3060

aacgtgatct cctgattaga gagggtggtt ttcctcaatg gaaccaaata taaagaggac   3120

ttgaacaaaa atgacagata caaactattt ctatcctgag tagtaatctc acacttcatc   3180

ctatagagtc aaccaccaca gataggaatt ccttattctt tttttaattt ttttaagaca   3240

gagtctcact ttgttgccca ggctggagcg cagtggggtg atctcatctc cctgcaacct   3300

ccgcctcctg ggttcaagcg attcttgtgc ctcagcttcc caagcagctg ggattacagg   3360

tgcccgccac cacgcccagc taatttttgc atttttagta gagatggggt ttcaccatgt   3420

tggccacgct cgtctccaac tcctgacctc aggtaatccg cctgccttgg cctcccaaag   3480

tgctgggatt acagacatga accaccacgc ctggctggaa tacttactct tgtcgggaga   3540

ttgaaccact aaaatgttag agcagaattc attatgctgt ggtcacaggg gtgtcttgtc   3600

tgagaacaaa tacaattcag tcttctcttt ggggttttag tatgtgtcaa acataggact   3660

ggaagtttgc ccctgttctt ttttcttttg aaagaacatc agttcatgcc tgaggcatga   3720

gtgactgtgc atttgagaat agttttccct attctgtgga tacagtccca gagttttcag   3780

ggagtacaca ggtagattag tttgaagcat tgacctttta tttattcctt atttctcttt   3840

catcaaaaca aaacagcagc tgtgggagga gaaatgagag ggcttaaatg aaatttaaaa   3900

taagctatat tatacaaata ctatctctgt attgttctga ccctggtaaa tatatttcaa   3960

aacttcagat gacaaggatt agaacactca ttaaagatgc tattcttcag aaaaaaaaaa   4020

aaaaaaaaaa aaaa                                                     4034
```

```
<210> SEQ ID NO 94
<211> LENGTH: 2964
<212> TYPE: DNA
<213> ORGANISM: Homo sapiens

<400> SEQUENCE: 94

agtcggcggc ggctgctgct gcctgtggcc cgggcggctg ggagaagcgg agtgttggtg     60

agtgacgcgg cggaggtgta gtttgacgcg gtgtgttacg tgggggagag aataaaactc    120

cagcgagatc cgggccgtga acgaaagcag tgacggagga gcttgtacca ccggtaacta    180
```

-continued

```
aatgaccatg gaatctggag ccgagaacca gcagagtgga gatgcagctg taacagaagc    240
tgaaaaccaa caaatgacag ttcaagccca gccacagatt gccacattag cccaggtatc    300
tatgccagca gctcatgcaa catcatctgc tcccaccgta actctagtac agctgcccaa    360
tgggcagaca gttcaagtcc atggagtcat tcaggcggcc cagccatcag ttattcagtc    420
tccacaagtc caaacagttc agatttcaac tattgcagaa agtgaagatt cacaggagtc    480
agtggatagt gtaactgatt cccaaaagcg aagggaaatt ctttcaagga ggccttccta    540
caggaaaatt ttgaatgact tatcttctga tgcaccagga gtgccaagga ttgaagaaga    600
gaagtctgaa gaggagactt cagcacctgc catcaccact gtaacggtgc caactccaat    660
ttaccaaact agcagtggac agtatattgc cattacccag ggaggagcaa tacagctggc    720
taacaatggt accgatgggg tacagggcct gcaaacatta accatgacca atgcagcagc    780
cactcagccg ggtactacca ttctacagta tgcacagacc actgatggac agcagatctt    840
agtgcccagc aaccaagttg ttgttcaagc tgcctctgga gacgtacaaa cataccagat    900
tcgcacagca cccactagca ctattgcccc tggagttgtt atggcatcct ccccagcact    960
tcctacacag cctgctgaag aagcagcacg aaagagagag gtccgtctaa tgaagaacag   1020
ggaagcagct cgagagtgtc gtagaaagaa gaaagaatat gtgaaatgtt tagaaaacag   1080
agtggcagtg cttgaaaatc aaaacaagac attgattgag gagctaaaag cacttaagga   1140
cctttactgc cacaaatcag attaatttgg gatttaaatt ttcacctgtt aaggtggaaa   1200
atggactggc ttggccacaa cctgaaagac aaaataaaca ttttattttc taaacatttc   1260
tttttttcta tgcgcaaaac tgcctgaaag caactacaga atttcattca tttgtgcttt   1320
tgcattaaac tgtgaatgtt ccaacacctg cctccacttc tcccctcaag aaattttcaa   1380
cgccaggaat catgaagaga cttctgcttt tcaaccccca ccctcctcaa gaagtaataa   1440
tttgtttact tgtaaattga tgggagaaat gaggaaaaga aaatcttttt aaaaatgatt   1500
tcaaggtttg tgctgagctc cttgattgcc ttagggacag aattacccca gcctcttgag   1560
ctgaagtaat gtgtgggccg catgcataaa gtaagtaagg tgcaatgaag aagtgttgat   1620
tgccaaattg acatgttgtc acattctcat tgtgaattat gtaaagttgt taagagacat   1680
accctctaaa aaagaacttt agcatggtat tgaaggaatt agaaatgaat ttggagtgct   1740
ttttatgtat gttgtcttct tcaatactga aaatttgtcc ttggttctta aaagcattct   1800
gtactaatac agctcttcca tagggcagtt gttgcttctt aattcagttc tgtatgtgtt   1860
caacattttt gaatacatta aaagaagtaa ccaactgaac gacaaagcat ggtatttgaa   1920
ttttaaatta aagcaaagta aataaaagta caaagcatat tttagttagt actaaattct   1980
tagtaaaatg ctgatcagta aaccaatccc ttgagttata taacaagatt tttaaataaa   2040
tgttattgtc ctcaccttca aaaatattta tattgtcact catttacgta aaaagatatt   2100
tctaatttac tgttgcccat tgcacttaca taccaccacc aagaaagcct tcaagatgtc   2160
aaataaagca aagtgatata tatttgttta tgaaatgtta catgtagaaa aatactgatt   2220
ttaaatattt tccatattaa caatttaaca gagaatctct agtgaatttt ttaaatgaaa   2280
gaagttgtaa ggatataaaa agtacagtgt tagatgtgca caaggaaagt tattttcaga   2340
catatttgaa tgactgctgt actgcaatat ttggattgtc attcttacaa aacatttttt   2400
tgttctcttg taaaaagagt agttattagt tctgctttag ctttccaata tgctgtatag   2460
cctttgtcat tttataattt taattcctga ttaaaacagt ctgtatttgt gtatatcata   2520
cattgttttc aataccactt ttaattgtta ctcattttat tcactaagct cgataaatct   2580
```

```
aacagttact cttaaaaaaa aaaaaaagac taaggtggat tttaaaaatt ggaaactgac   2640

ataatgttag gttataattt ctcatttgga gccgggcgca gtggctcacg cctgtaatcc   2700

cagcactttg ggaggccaag gtgggtggat cacctgtggt caagagttca agaccagcct   2760

ggccatcatg gtgaaacccc atctctacta aaaatacaaa aattagccag gcgtggtggc   2820

tggcgcctgt aatcccagct actcaggagg ttgaggcagc agaattgctt gaacccagga   2880

ggcagagggt tgcagtgagc cgagatagca ccattgcact ccagcctggg cgactccatc   2940

tcaaaaaata aaaaaaaaaa aaaa                                         2964
```

<210> SEQ ID NO 95
<211> LENGTH: 1977
<212> TYPE: DNA
<213> ORGANISM: Homo sapiens

<400> SEQUENCE: 95

```
gttttggcag gagcgggaga attctgcgga gcctgcggga cggcggcggt ggcgccgtag     60

gcagccggga cagtgttgta cagtgttttg ggcatgcacg tgatactcac acagtggctt    120

ctgctcacca acagatgaag acagatgcac caacgaggct gatgggaacc atcctgtaga    180

ggtccatctg cgttcagacc cagacgatgc cagagctatg actgggcctg caggtgtggc    240

gccgagggga gatcagccat ggagcagcca caggaggaag cccctgaggt ccgggaagag    300

gaggagaaag aggaagtggc agaggcagaa ggagccccag agctcaatgg gggaccacag    360

catgcacttc cttccagcag ctacacagac ctctcccgga gctcctcgcc accctcactg    420

ctggaccaac tgcagatggg ctgtgacggg gcctcatgcg gcagcctcaa catggagtgc    480

cgggtgtgcg gggacaaggc atcgggcttc cactacggtg ttcatgcatg tgaggggtgc    540

aagggcttct tccgtcgtac gatccgcatg aagctggagt acgagaagtg tgagcgcagc    600

tgcaagattc agaagaagaa ccgcaacaag tgccagtact gccgcttcca gaagtgcctg    660

gcactgggca tgtcacacaa cgctatccgt tttggtcgga tgccggaggc tgagaagagg    720

aagctggtgg cagggctgac tgcaaatgag gggagccagt acaacccaca ggtggccgac    780

ctgaaggcct tctccaagca catctacaat gcctacctga aaaacttcaa catgaccaaa    840

aagaaggccc gcagcatcct caccggcaaa gccagccaca cggcgccctt tgtgatccac    900

gacatcgaga cattgtggca ggcagagaag gggctggtgt ggaagcagtt ggtgaatggc    960

ctgcctccct acaaggagat cagcgtgcac gtcttctacc gctgccagtg caccacagtg   1020

gagaccgtgc gggagctcac tgagttcgcc aagagcatcc ccagcttcag cagcctcttc   1080

ctcaacgacc aggttaccct tctcaagtat ggcgtgcacg aggccatctt cgccatgctg   1140

gcctctatcg tcaacaagga cgggctgctg gtagccaacg gcagtggctt tgtcacccgt   1200

gagttcctgc gcagcctccg caaacccttc agtgatatca ttgagcctaa gtttgaattt   1260

gctgtcaagt tcaacgccct ggaacttgat gacagtgacc tggccctatt cattgcggcc   1320

atcattctgt gtggaggtga gtgagagtgg ggcaggtggg ctggcctggc acacccagtc   1380

gtcctggggg ttggccctca ctgcagggca ctgtgcctga gctctgacag tgtggggaag   1440

tgtccctgtg atcttggcag tggaacatgc aaggcactga ctgagcatgc aggatcagct   1500

ccatctcatt atgtacgtag atagaggtgg agacaggaaa aagactaagc cagacgtggt   1560

ggctcacacc tgtaatccca gcactttggc aggccgaggc gggtggatca cttgaggtca   1620

ggagttcgaa accagcctgg ccaacatggt gaaaccccgt ctctactaaa aatacaaaaa   1680

attagccaga tgtggtggca cgcgcctgta atcccagcta cttgggaggc tgagccagga   1740
```

```
gaatcgcttg aacccgagag gtggaggttg cagtgagcca aaatcccacc actgcactcc   1800

agcctgggtg acagagtgag accctgtctc aaaaaaaagg aaaaggacta acaggcagta   1860

tgctgtcatg ttaatgtggg gtggaaaaat tgtctgcatt ttttctgcat ttttaaaatt   1920

ccaacacaat aaatacaata ataactatgc taaaaaaaaa aaaaaaaaaa aaaaaaa      1977
```

<210> SEQ ID NO 96
<211> LENGTH: 2594
<212> TYPE: DNA
<213> ORGANISM: Homo sapiens

<400> SEQUENCE: 96

```
gcttcgggtg ccatggggac tcctcccggc ctgcagaccg actgcgaggc gctgctcagc     60

cgcttccagg agacggacag tgtacgcttc gaggacttca cggagctctg gagaaacatg    120

aagttcggga ctatcttctg tggcagaatg agaaatttag aaaagaacat gtttacaaaa    180

gaagctttag ctttggcttg gcgatatttt ttacctccat acaccttcca gatcagagtt    240

ggtgctttgt atctgctata tggattatat aatacccaac tgtgtcaacc aaaacaaaag    300

atcagagttg ccctgaagga ttgggatgaa gttttaaaat ttcagcaaga tttagtaaat    360

gcacagcatt ttgatgcagc ttatattttt aggaagctac gactagacag agcatttcac    420

tttacagcaa tgcccaaatt gctgtcatat aggatgaaga aaaaaattca ccgagctgaa    480

gttacagaag aatttaagga cccaagtgat cgtgtgatga aacttatcac ttctgatgta    540

ttagaggaaa tgctgaatgt tcatgatcat tatcagaaca tgaaacatgt aatttcagtt    600

gataagtcca agccagataa agccctcagc ttgataaagg atgatttttt tgacaatatt    660

aagaacatag ttttggagca tcagcagtgg cacaaagaca gaaagaatcc atccttaaag    720

tcaaaaacta atgatggaga agaaaaaatg gaaggaaatt cacaagaaac ggagagatgt    780

gaaagggcag aatcattagc gaaaataaaa tcaaaggcct tttcagttgt catacaggca    840

tccaaatcaa gaaggcatcg tcaagtcaaa ctcgactctt ctgactctga ttctgcatct    900

ggtcaagggc aagtcaaagc aactaggaaa aaagagaaga aagaaagatt gaaaccagca    960

ggaaggaaga tgtctctcag aaacaaaggc aatgtgcaga atatacacaa ggaagataaa   1020

cctttaagtc tgagtatgcc tgtaattaca gaagaagaag agaatgaaag tttgagtgga   1080

acagagttca ctgcatccaa gaagaggaga aaacactgaa caaagagcct ggtgtagttt   1140

ttaattttga gttttctgac agaagaaaag attgatattt tgtgtattga acaggaagac   1200

tgccagtatt aaaaaaatcc ttctgggaat ctgtaggtta tttcttggaa attgcaatac   1260

gtagttctag aataaaagta caaaaaatta gaataagaat tctttaacat tttctttaat   1320

gatttgcata aatggagata aaacttgtat ttagtatgta atagaaaaaa ttctgttatt   1380

cgcagattgt tactatttcc tataaggttt tgtgatacta tactgtccta atacagtctg   1440

gtaatactat tctattttat ttaaaatatt ttttattgaa atattaatgt ttattacatg   1500

caaataacta ttttgtatct acagtcggat aatggatttt ttattttgta tatttattct   1560

attttgtata ttgttaagtg caataaagtt tttgccttgc tttatttttt aatacataaa   1620

acttacattc tcataacgtg attgataact taggaagttc acaatgtatt ttctacttct   1680

gcaattaaat attctttagt gcttgtttat tattactaaa tactaattaa gtactaacaa   1740

gtacttaaat actaatgtat taagtattta agtactttct aataaaatct ttaacaataa   1800

taatgtaaat ttcagaatgt gtctctggta cagaatagtt gatattaaca gaaaaaaaaa   1860

aatctgtagc ttcatgaata tgccactctg ttaatttctt gttccagaca ttttaataga   1920
```

gattgcttga gccatgttgt ttgaattgct gccaatagca gaccatatcc ctatcatgtt 1980
gttggctcaa ctgttttttt tttttcccta atagagatgg agtatcgcta tgttgctcag 2040
gctggtcttg aactcctggg ctcaagctat cctcctgcct cagcctccca aagtactggg 2100
attataggtg tgagctactg tacccagcct taacctgttt cacagttgat tatacttcat 2160
gctgttttcc agcatggtat tattaaggga tttaaagttt gggttgcatg cctgtaatcc 2220
cagcattttg ggaggccgag gtgggcggat cacgaggtca ggagatcgag accatcgtga 2280
ctaacacagt gaaaccccgt ctctaataaa aatacgaaaa attagccagg cgtggtggcg 2340
ggcgcctgta atcccagcta ctcgggaagc tgaggcagga gaatggtgtg aacccagtga 2400
gccgagatcg tgccactgca ctccagcctg ggcaacagag tgagacttcg tctcaaaaaa 2460
aaaaaaaaaa gtttgggttg aagatcaaat tcgtgatatc tctatatcta atctttaaaa 2520
atcagaatgc taatgctgac gcaaataaaa ttttcattta ttagcaaaaa aaaaaaaaaa 2580
aaaaaaaaaa aaaa 2594

<210> SEQ ID NO 97
<211> LENGTH: 273
<212> TYPE: DNA
<213> ORGANISM: Homo sapiens

<400> SEQUENCE: 97
tttttttttt tttttttttt gggacggagt tcgctctgtc gcccaggctg gagcgcactg 60
gtgcaatctc agcttgctac accctctacc tcccgggtgt caccatgttg gccaggctgg 120
ttttgaactt ctgactcaag tgatctgcac acctcagcct ttaaagtgct aggattacaa 180
gcatgagcca ccacacctgc tccttctatt tcattttaac ataaataagt aatagtagct 240
aagacttact aagcactatg tattagacag ttt 273

<210> SEQ ID NO 98
<211> LENGTH: 5059
<212> TYPE: DNA
<213> ORGANISM: Homo sapiens

<400> SEQUENCE: 98
ctggttctca acttcttttg aaataatgtt catagagaag gagggctgtc tgagattcga 60
gggaaacaag ctctcaggac ttccggtcgc catgatggct gtgggcggta aacgcggtta 120
gtgcaagcat ctgggccatc ttcaatggta aaaaagatac agtaaagaca taaataccac 180
atttgacaaa tggaaaaaaa ggagtgtcca gaaaagagta gcagcagtga ggaagagctg 240
ccgagacggg tatacaggga gctaccctgt gtttctgaga ccctttgtga catctcacat 300
tttttccaag aagatgatga gacagaggca gagccattat tgttccgtgc tgttcctgag 360
tgtcaactat ctggggggga cattcccagg agacatttgc tcagaagaga atcaaatagt 420
ttcctcttat gcttctaaag tctgttttga gatcgaagaa gattataaaa atcgtcagtt 480
tctggggcct gaaggaaatg tggatgttga gttgattgat aagagcacaa acagatacag 540
cgtttggttc cccactgctg gctggtatct gtggtcagcc acaggcctcg gcttcctggt 600
aagggatgag gtcacagtga cgattgcgtt tggttcctgg agtcagcacc tggccctgga 660
cctgcagcac catgaacagt ggctggtggg cggccccttg tttgatgtca ctgcagagcc 720
agaggaggct gtcgccgaaa tccacctccc ccacttcatc tccctccaag gtgaggtgga 780
cgtctcctgg tttctcgttg cccattttaa gaatgaaggg atggtcctgg agcatccagc 840
ccgggtggag cctttctatg ctgtcctgga aagccccagc ttctctctga tgggcatcct 900

```
gctgcggatc gccagtggga ctcgcctctc catccccatc acttccaaca cattgatcta    960
ttatcacccc caccccgaag atattaagtt ccacttgtac cttgtcccca gcgacgcctt   1020
gctaacaaag gcgatagatg atgaggaaga tcgcttccat ggtgtgcgcc tgcagacttc   1080
gcccccaatg gaacccctga actttggttc cagttatatt gtgtctaatt ctgctaacct   1140
gaaagtaatg cccaaggagt tgaaattgtc ctacaggagc cctggagaaa ttcagcactt   1200
ctcaaaattc tatgctgggc agatgaagga acccattcaa cttgagatta ctgaaaaaag   1260
acatgggact ttggtgtggg atactgaggt gaagccagtg gatctccagc ttgtagctgc   1320
atcagcccct cctcctttct caggtgcagc ctttgtgaag gagaaccacc ggcaactcca   1380
agccaggatg gggacctga aaggggtgct cgatgatctc caggacaatg aggttcttac    1440
tgagaatgag aaggagctgg tggagcagga aaagacacgg cagagcaaga atgaggcctt   1500
gctgagcatg gtggagaaga aaggggacct ggccctggac gtgctcttca gaagcattag   1560
tgaaagggac ccttacctcg tgtcctatct tagacagcag aatttgtaaa atgagtcagt   1620
taggtagtct ggaagagaga atccagcgtt ctcattggaa atggataaac agaaatgtga   1680
tcattgattt cagtgttcaa gacagaagaa gactgggtaa catctatcac acaggctttc   1740
aggacagact tgtaacctgg catgtaccta ttgactgtat cctcatgcat tttcctcaag   1800
aatgtctgaa gaaggtagta atattccttt taaatttttt ccaaccattg cttgatatat   1860
cactatttta tccattgaca tgattcttga agacccagga taaaggacat ccggataggt   1920
gtgtttatga aggatggggc ctggaaaggc aacttttcct gattaatgtg aaaaataatt   1980
cctatggaca ctccgtttga agtatcacct tctcataact aaaagcagaa aagctaacaa   2040
aagcttctca gctgaggaca ctcaaggcat acatgatgac agtctttttt tttttgtat    2100
gttaggactt taacacttta tctatggcta ctgttattag aacaatgtaa atgtatttgc   2160
tgaaagagag cacaaaaatg ggagaaaatg caaacatgag cagaaaatat tttcccactg   2220
gtgtgtagcc tgctacaagg agttgttggg ttaaatgttc atggtcaact ccaaggaata   2280
ctgagatgaa atgtggtaaa tcaactccac agaaccacca aaaagaaaat gagggtaatt   2340
cagcttattc tgagacagac attcctggca atgtaccata caaaaaaataa gccaactctg  2400
acatttggat tctaccatag actctgtcat tttgtagcca tttcagctgt cttttgatta   2460
atgttttcgt ggcacacata tttccatcct tttatgttta atctgtttaa aacaagttcc   2520
tagtagacac catctggttg agtcagtttt ttttatggtg tattttgaac ccattctgat   2580
agtctctttt aactggaaga tttcaattac ttacgttaat gtaattatta atatgttagg   2640
atttatcctc agtcagccag tttgttatgt cttttctatt ctactgttat cacatttgta   2700
ccacttaaag tggaatctag gcactttatc accatttaga tcctattacc ttttctcatc   2760
taggatatag ttatcttcta cataatcttt ctgtatctta aaacccatca ataaattatt   2820
atatatttc tacttttaat cactcagaag atttaaaaaa ctcatgagaa gagtaatctg    2880
ttatgttttt ccagatattt accatttctg ttgctcttcc ttcattattt tccaaatttc   2940
gttctgcaaa tttccacttc ttctgataga cgttttttag ttcttttaga gtggttctga   3000
taggtacaga ttctcttatt ttttgcttcc tctgaggaca tctttttctc accttcattc   3060
tcagtgatgt tttttgcttg tagtattttt agttgacatt gttttctgtt cagcagtttc   3120
cttttagctt ccgtatttcc tgatgagaaa tctgcagtca ttcaaattgt tgtttccctg   3180
tatgtagtgt gtcatttttc tgtcagattt caaggtattt atctttagtt tttagccatt   3240
tcattatgtt ggggatgagt ttccttgttt tattcccttt ggaatttgct ccaattcata   3300
```

```
aatttgcagt tttatgtctt ttaccaaact tagaggtttt cagcctaatt tctaaaaata   3360

cttttttatta gcctgatttt catctttata ggaaatagtt taagtgatga caagttccaa   3420

tagcttatat gcccagaagg ccttcaaaat aagaattttg aaagaataca gaaaacaaac   3480

ttttatatcc ttctcatgtc ttctactgta aaattcatat gctttgctac tctaaaccta   3540

gtttgaaatc aacagtcttg agaatagatg aaaattttga tgaatagtgg aattctttta   3600

aatggaaacc tcttacatgt gattttcctt gccatctaga aataaaccat agtatttatg   3660

ttgaatcaat caatattata ttttgttttt ttcctcctct tctgagactc ttattgtgga   3720

aatgttagac ttttatgttt tcctaaatgt ccctgatatt ctacttattt agaacatctt   3780

ttcatttttt ccattattct gattgggtaa ttttaatttg tctattttca aatttgctgg   3840

agtgttcacc tgttgttgtc tgtgtcgtcc cactgagtgc attcaccacc ttttaaattt   3900

tggtcactgt atgtatcagt tctaaaattt ccattttgtt ctctatattt taaatttctt   3960

ggcttatatt ctattttcct gcaaatgtgt cagcatttgc ttgtttgagc tttttttttt   4020

tcaagacagg gtctcaactc tgttacccag gctggagtgc agtggtgcga tctcagctca   4080

ctgcaacctc tgcctcctgg ttcaagcgat tattgtgcct cagcctcctg agtagctggg   4140

attacaggca tgcaccacca cagcccagct aatttttttgt atttttagta gagacagagt   4200

tttgctatgt tggccaggct ggttttgaac tcctggcctc aagtgatcca cccacctcag   4260

cctcccaaag tgctgggatt acaggccact acacctggca catttgagta tttttttttt   4320

tttttttttt ttgagatgga gtctcgctct gtcatctagg ctggagtgca gtggtgtgat   4380

ctcagctcac tgcagcctct gtctcccggg ctcaagcgat tctcttgcct cagcctcctg   4440

agtagctagg actacaggtg catgccaaca cgcccggcta atttttttaa aaaatatttt   4500

tagtagagac agggtttcac cattttggcc aggatggtct cgatctcctg acctcatgat   4560

ccacccgcct cggccttcca aagtgctggg attacaggca tgagccaccg tgcctggcct   4620

catttgagta tttttataat gtctctttta aagtctttgt cagataattc cactgtacat   4680

gttattcagt gtttggtgtc cactgagttg tcatttgcca gacaagtgga gatttttgca   4740

gctcatcctt gtattctcag tagttccgat atgtaccctc gacatgtgaa tgttatctta   4800

tgagactctg ttttatttgt atccaacaga agatgtttat tatttatttg gctttctgtg   4860

aactgaggtc ttaatatcag ctcattttaa aagtctttgc agtggtattc ggatctatcc   4920

tgtgtgtgcc tatgagattg ggtgcagtgt atcctgttag ctccattctc agggcgtttg   4980

aatgtgaatt aggaccagcg caatgaatgc tcaagttggg gttgggcgtt agaattcata   5040

aaagtcttta tatgctcag                                                5059
```

<210> SEQ ID NO 99
<211> LENGTH: 2962
<212> TYPE: DNA
<213> ORGANISM: Homo sapiens

<400> SEQUENCE: 99

```
ggatcctttc tggaatggag gtcttatgag ctgctattga acacggcaga gcctgttggt     60

gacctgcaca caggagccct ccagtcagta ctgattgaat tactcaaggc tgcctctctg    120

caaagttgag cactacagga cgtcgggact gggcatttcc ttccaacatg gccgccactg    180

cctctccgca gccactcgcc actgaggatg ccgattctga gaatagcagc ttctattact    240

atgactacct ggatgaagtg gccttcatgc tctgcaggaa ggatgcagtg gtgtcctttg    300

gcaaagtctt cctcccagtc ttctatagcc tgatttttgt gttgggcctc agcgggaacc    360
```

```
tccttcttct catggtcttg ctccgttacg tgcctcgcag gcggatggtt gagatctatc    420
tgctgaatct ggccatctcc aaccttctgt ttctggtgac actgcccttc tggggcatct    480
ccgtggcctg gcattgggtc ttcgggagtt tcttgtgcaa gatggtgagc actctttata    540
ctattaactt ttacagtggc atctttttca ttagctgcat gagcctggac aagtacctgg    600
agatcgttca tgctcagccc taccacaggc tgaggacccg ggccaagagc ctgctccttg    660
ctaccatagt atgggctgtg tccctggccg tctccatccc tgatatggtc tttgtacaga    720
cacatgaaaa tcccaagggt gtgtggaact gccacgcaga tttcggcggg catgggacca    780
tttggaagct cttcctccgc ttccagcaga acctcctagg gtttctcctt ccactccttg    840
ccatgatctt cttctactcc cgtattggtt gtgtcttggt gaggctgagg cccgcaggcc    900
agggccgggc tttaaaaata gctgcagcct tggtggtggc cttcttcgtg ctatggttcc    960
catacaatct caccttgttt ctgcatacgc tgttggacct gcaagtattc gggaactgtg   1020
aggtcagcca gcatctagac tacgcactcc aggtaacaga gagcatcgcc ttccttcact   1080
gctgcttttc ccccatcctg tatgccttct ccagtcaccg cttccgccag tacctgaagg   1140
ctttcctggc tgccgtgctt ggatggcacc tggcacctgg cactgcccag gcctcattat   1200
ccagctgttc tgagagcagc atacttactg cccaagagga aatgactggc atgaatgacc   1260
ttggagagag gcagtctgag aactacccta acaaggagga tgtggggaat aaatcagcct   1320
gagtgaccaa attttggtct ggtgggaaca gatgggaacc agctcaattg ggtgtccact   1380
caaagtgctc tctccagggg cctcagtgac tgtgttgcta aacccagtgg tcagttctca   1440
gttctcagcc atcagcagca tttgctcgcc ccgccttctt cctccacttt cttcacttgc   1500
ttccaggata ccacgctttc ttttctgaat tgctacaatc tttcttcctt ccttccttgc   1560
ttccttcctt ccttccttcc ctctctccct ccctccctcc ctcgcttctt cccttcctcc   1620
tttcctccct tcctactttc cttccttcct tctgacaggg tcttgctcta ttgctctgtc   1680
acccaggctg gaatgcagtg gcgagatctc cgctcactgt agcctcctcc ccctgggttg   1740
aagcaattct catgcctcag cctcccaagt agccaggact ataggcacct gccaccatgc   1800
ctggctaatt tttgtatttt ttttctttct ttctttcttt tcttttttttt tttttttga    1860
gacggagtct cactcttgtt gcccaggctg gacaacaatg gcgcgatctc ggctcactgc   1920
aacctccacc tcccggattc aagcgattct cctgcctcag cctcctgagt agctggaact   1980
acatgcgcgt gccaccacgc acagctaatt tttataattt tagtagagat ggggtttcac   2040
tgcgttggcc aggatgatct cgatctcttg accttgggat ccacccgcct tggcctccca   2100
aagtgctggg attacaggtg tgagccacca tgcctggccc taatttttgt gtttttatta   2160
gaaacagagt ttcaccatgt tggccaggct ggagaattgc tgtaatagtt ttccaactgg   2220
cccctgtcct tcctctctct tgctctcctc ccatctcatc tgcacctagc agccagagtg   2280
atcctgatac tctcggcctt tacttccgcc tccctcagag cagcagcctg tcaaaacacc   2340
agattacaac aaatttagtt taaaggtctc aattagcgtt attggcaatt ctagaatcag   2400
gcaacagact cattgaatca ggaacagatt cactccataa aatacagaga gtgctgcaat   2460
gagctgggta gaagaggtta gttttataga caggaagggg ctgtcaaagg cagaaagaaa   2520
tgaagaacaa aaaaaaagat tgattttttt tttttgaga caggatctca ctctgtcatc    2580
caggctgaag tccaatccca caatcatggc tcactgcagc caccacctcc tgagctcaag   2640
tgatcctccc atctaagccc ccaagtagct aggactacag gagcacacca ccacacctgg   2700
ctaattttg tattttttgt ggagacaggg tctcagtatg ttacccaggt tggactggaa    2760
```

```
acccttggct caagcaattt gcctgcctca gcctcccaaa gtgctgggat tacaggcgtg   2820

agccactgca cagggccaga ttcatcattt caaagttact ttctatatgc ggccggaaca   2880

gggtggttga catcagtttt cttcaggtta ctttttaata atgattaaaa cggggaactt   2940

cattatcaaa aaaaaaaaaa aa                                            2962
```

<210> SEQ ID NO 100
<211> LENGTH: 562
<212> TYPE: DNA
<213> ORGANISM: Homo sapiens

<400> SEQUENCE: 100

```
ctggaattga ggctgagcca aagaccccag ggccgtctca gtctcataaa aggggatcag     60

gcaggaggag tttgggagaa acctgagaag ggcctgattt gcagcatcat gatgggcctc    120

tccttggcct ctgctgtgct cctggcctcc ctcctgagtc tccaccttgg aactgccaca    180

cgtgggagtg acatatccaa gacctgctgc ttccaataca gccacaagcc ccttccctgg    240

acctgggtgc gaagctatga attcaccagt aacagctgct cccagcgggc tgtgatattc    300

actaccaaaa gaggcaagaa agtctgtacc catccaagga aaaaatgggt gcaaaaatac    360

atttctttac tgaaaactcc gaaacaattg tgactcagct gaattttcat ccgaggacgc    420

ttggaccccg ctcttggctc tgcagccctc tggggagcct gcggaatctt ttctgaaggc    480

tacatggacc cgctggggag gagagggtgt ttcctcccag agttacttta ataaaggttg    540

ttcatagagt tgacttgttc at                                             562
```

<210> SEQ ID NO 101
<211> LENGTH: 1873
<212> TYPE: DNA
<213> ORGANISM: Homo sapiens

<400> SEQUENCE: 101

```
gacgatacgc cgggcgcagg cgcagaagcc gcgcccgtcc gcggcgccgc cagccagggc     60

ggaaacggct gcggcttcgc tagggacgca tgcgcgggtc ccttagtttt cgcgagataa    120

cggtcgaaaa cgcgctcttg tcgatttcct gtagtgaatc aggcaccgga gtgcaggttc    180

gggggtggaa tccttgggcc gctgggcaag cggcgagacc tggccagggc cagcgagccg    240

aggacagagg gcgcacggag ggccgggccg cagccccggc cgcttgcaga ccccgccatg    300

gacccgttcc tggtgctgct gcactcggtg tcgtccagcc tgtcgagcag cgagctgacc    360

gagctcaagt tcctatgcct cgggcgcgtg ggcaagcgca agctggagcg cgtgcagagc    420

ggcctagacc tcttctccat gctgctggag cagaacgacc tggagcccgg gcacaccgag    480

ctcctgcgcg agctgctcgc ctccctgcgg cgccacgacc tgctgcggcg cgtcgacgac    540

ttcgaggcgg gggcggcggc cggggccgcg cctggggaag aagacctgtg tgcagcattt    600

aacgtcatat gtgataatgt ggggaaagat tggagaaggc tggctcgtca gctcaaagtc    660

tcagacacca agatcgacag catcgaggac agataccccc gcaacctgac agagcgtgtg    720

cgggagtcac tgagaatctg gaagaacaca gagaaggaga acgcaacagt ggcccacctg    780

gtgggggctc tcaggtcctg ccagatgaac ctggtggctg acctggtaca agaggttcag    840

caggcccgtg acctccagaa caggagtggg gccatgtccc cgatgtcatg gaactcagac    900

gcatctacct ccgaagcgtc ctgatgggcc gctgctttgc gctggtggac cacaggcatc    960

tacacagcct ggactttggt tctctccagg aaggtagccc agcactgtga agacccagca   1020

ggaagccagg ctgagtgagc cacagaccac ctgcttctga actcaagctg cgtttattaa   1080
```

```
tgcctctccc gcaccaggcc gggcttgggc cctgcacaga tatttccatt tcttcctcac   1140

tatgacactg agcaagatct tgtctccact aaatgagctc ctgcgggagt agttggaaag   1200

ttggaaccgt gtccagcaca gaaggaatct gtgcagatga gcagtcacac tgttactcca   1260

cagcggagga gaccagctca gaggcccagg aatcggagcg aagcagagag gtggagaact   1320

gggatttgaa cccccgccat ccttcaccag agcccatgct caaccactgt ggcgttctgc   1380

tgcccctgca gttggcagaa aggatgtttt gtcccatttc cttggaggcc accgggacag   1440

acctggacac tagggtcagg cggggtgcgt ggtggggaga ggcatggctg gggtgggggt   1500

ggggagacct ggttggccgt ggtccagctc ttggcccctg tgtgagttga gtctcctctc   1560

tgagactgct aagtaggggc agtgatggtt gccaggacga attgagataa tatctgtgag   1620

gtgctgatga gtgattgaca cacagcactc tctaaatctt ccttgtgagg attatgggtc   1680

ctgcaattct acagtttctt actgttttgt atcaaaatca ctatctttct gataacagaa   1740

ttgccaaggc agcgggatct cgtatcttta aaaagcagtc ctcttattcc taaggtaatc   1800

ctattaaaac acagctttac aacttccata tcacaaaaaa aaaaaaaaaa aaaaaaaaaa   1860

aaaaaaaaaa aaa                                                      1873


<210> SEQ ID NO 102
<211> LENGTH: 4082
<212> TYPE: DNA
<213> ORGANISM: Homo sapiens

<400> SEQUENCE: 102

ggcggtcccc tgttctcccc gctcaggtgc ggcgctgtgg caggaagcca ccccctcggt     60

cggccggtgc gcggggctgt tgcgccatcc gctccggctt tcgtaaccgc accctgggac    120

ggcccagaga cgctccagcg cgagttcctc aaatgttttc ctgcgttgcc aggaccgtcc    180

gccgctctga gtcatgtgcg agtgggaagt cgcactgaca ctgagccggg ccagagggag    240

aggagccgag cgcggcgcgg ggccgaggga ctcgcagtgt gtgtagagag ccgggctcct    300

gcggatgggg gctgcccccg gggcctgagc ccgcctgccc gcccaccgcc ccgccccgcc    360

cctgccaccc ctgccgcccg gttcccatta gcctgtccgc ctctgcggga ccatggagtg    420

gtagccgagg aggaagcatg ctggccgtcg gctgcgcgct gctggctgcc ctgctggccg    480

cgccgggagc ggcgctggcc ccaaggcgct gccctgcgca ggaggtggcg agaggcgtgc    540

tgaccagtct gccaggagac agcgtgactc tgacctgccc gggggtagag ccggaagaca    600

atgccactgt tcactgggtg ctcaggaagc cggctgcagg ctcccacccc agcagatggg    660

ctggcatggg aaggaggctg ctgctgaggt cggtgcagct ccacgactct ggaaactatt    720

catgctaccg ggccggccgc ccagctggga ctgtgcactt gctggtggat gttccccccg    780

aggagcccca gctctcctgc ttccggaaga gcccccctcag caatgttgtt tgtgagtggg    840

gtcctcggag caccccatcc ctgacgacaa aggctgtgct cttggtgagg aagtttcaga    900

acagtccggc cgaagacttc caggagccgt gccagtattc ccaggagtcc cagaagttct    960

cctgccagtt agcagtcccg gagggagaca gctctttcta catagtgtcc atgtgcgtcg   1020

ccagtagtgt cgggagcaag ttcagcaaaa ctcaaacctt tcagggttgt ggaatcttgc   1080

agcctgatcc gcctgccaac atcacagtca ctgccgtggc cagaaacccc cgctggctca   1140

gtgtcacctg gcaagacccc cactcctgga actcatcttt ctacagacta cggtttgagc   1200

tcagatatcg ggctgaacgg tcaaagacat tcacaacatg gatggtcaag gacctccagc   1260

atcactgtgt catccacgac gcctggagcg gcctgaggca cgtggtgcag cttcgtgccc   1320
```

```
aggaggagtt cgggcaaggc gagtggagcg agtggagccc ggaggccatg ggcacgcctt   1380
ggacagaatc caggagtcct ccagctgaga acgaggtgtc cacccccatg caggcactta   1440
ctactaataa agacgatgat aatattctct tcagagattc tgcaaatgcg acaagcctcc   1500
caggttcaag aagacgtgga agctgcgggc tctgaaggaa ggcaagacaa gcatgcatcc   1560
gccgtactct ttggggcagc tggtcccgga gaggcctcga cccaccccag tgcttgttcc   1620
tctcatctcc ccaccggtgt cccccagcag cctggggtct gacaatacct cgagccacaa   1680
ccgaccagat gccagggacc cacggagccc ttatgacatc agcaatacag actacttctt   1740
ccccagatag ctggctgggt ggcaccagca gcctggaccc tgtggatgat aaaacacaaa   1800
cgggctcagc aaaagatgct tctcactgcc atgccagctt atctcagggg tgtgcggcct   1860
ttggcttcac ggaagagcct tgcggaaggt tctacgccag gggaaaatca gcctgctcca   1920
gctgttcagc tggttgaggt ttcaaacctc cctttccaaa tgcccagctt aaaggggcta   1980
gagtgaactt gggccactgt gaagagaacc atatcaagac tctttggaca ctcacacgga   2040
cactcaaaag ctgggcaggt tggtgggggc ctcggtgtgg agaagcggct ggcagcccac   2100
ccctcaacac ctctgcacaa gctgcaccct caggcaggtg ggatggattt ccagccaaag   2160
cctcctccag ccgccatgct cctggcccac tgcatcgttt catcttccaa ctcaaactct   2220
taaaacccaa gtgccttagc aaattctgtt tttctaggcc tggggacggc ttttacttaa   2280
accgccaagg ctgggggaag aagctctctc ctccctttct tccctacagt tgaaaaacag   2340
ctgagggtga gtgggtgaat aatacagtat ctcagggcct ggtcgttttc aacagaatta   2400
taattagttc ctcattagca ttttgctaaa tgtgaatgat gatcctaggc atttgctgaa   2460
tacagaggca actgcattgg ctttgggttg caggacctca ggtgagaagc agaggaagga   2520
gaggagaggg gcacagggtc tctaccatcc cctgtagagt gggagctgag tgggggatca   2580
cagcctctga aaaccaatgt tctctcttct ccacctccca caaaggagag ctagcagcag   2640
ggagggcttc tgccatttct gagatcaaaa cggttttact gcagctttgt ttgttgtcag   2700
ctgaacctgg gtaactaggg aagataatat taaggaagac aatgtgaaaa gaaaaatgag   2760
cctggcaaga atgtgtttaa acttggtttt taaaaaactg ctgactgttt tctcttgaga   2820
gggtggaata tccaatattc gctgtgtcag catagaagta acttacttag gtgtggggga   2880
agcaccataa ctttgtttag cccaaaacca agtcaagtga aaaaggagga agagaaaaaa   2940
tattttcctg ccaggcatgg tggcccacgc acttcgggag gtcgaggcag gaggatcact   3000
tgagtccaga agtttgagat cagcctgggc aatgtgataa aaccccatct ctacaaaaag   3060
cataaaaatt agccaagtgt ggtagagtgt gcctgaagtc ccagatactt ggggggctga   3120
ggtgggagga tctcttgagc ctgggaggtc aaggctgcag tgagccgaga ttgcaccact   3180
gcactccagc ctgggtgaca gagcaagtga gaccctgtct caaaaaaaga aaaagaaaaa   3240
gaaaaaatat tttccctatt agagaagaga ttgtggtttc attctgtatt ttgtttttgt   3300
cttaaaaagt ggaaaaatag cctgcctctt ctctactcta gggaaaaacc agcgtgtgac   3360
tactccccca ggtggttatg gagagggtgt ccggtccctg tcccagtgcc gagaaggaag   3420
cctcccacga ctgcccggca gggtcctaga aattccccac cctgaaagcc ctgagctttc   3480
tgctatcaaa gaggttttaa aaaaatccca tttaaaaaaa atcccttacc tcggtgcctt   3540
cctcttttta tttagttcct tgagttgatt cagctctgca agaattgaag caggactaaa   3600
tgtctagttg taacaccatg attaaccact tcagctgact tttctgtccg agctttgaaa   3660
attcagtggt gttagtggtt acccagttag ctctcaagtt atcagggtat tccagagtgg   3720
```

```
ggatatgatt taaatcagcc gtgtaaccat ggacccaata tttaccagac cacaaaactt   3780

ttctaatact ctaccctctt agaaaaacca ccaccatcac cagacaggtg cgaaaggatg   3840

aaagtgacca tgttttgttt acggttttcc aggtttaagc tgttactgtc ttcagtaagc   3900

cgtgattttc attgctgggc ttgtctgtag attttagacc ctattgctgc ttgaggcaac   3960

tcatcttagg ttggcaaaaa ggcaggatgg ccgggcgcgg tggctcacgc ctgtaatcct   4020

agcactttgg gaggccaagg tgggaggatt gcttgagctc aggagtttga gaccaacctg   4080

gg                                                                  4082
```

<210> SEQ ID NO 103
<211> LENGTH: 2887
<212> TYPE: DNA
<213> ORGANISM: Homo sapiens

<400> SEQUENCE: 103

```
ggagctgaga ggaacaggaa gtgtcaggac tttacgaccc gcgcctccag ctgaggtttc     60

tagacgtgac ccagggcaga ctggtagcaa agcccccacg cccagccagg agcaccgccg    120

aggactccag cacaccgagg gacatgctgg gcctgcgccc cccactgctc gccctggtgg    180

ggctgctctc cctcgggtgc gtcctctctc aggagtgcac gaagttcaag gtcagcagct    240

gccgggaatg catcgagtcg gggcccggct gcacctggtg ccagaagctg aacttcacag    300

ggccgggggga tcctgactcc attcgctgcg acacccggcc acagctgctc atgaggggct    360

gtgcggctga cgacatcatg gaccccacaa gcctcgctga aacccaggaa gaccacaatg    420

gggccagaa gcagctgtcc ccacaaaaag tgacgcttta cctgcgacca ggccaggcag    480

cagcgttcaa cgtgaccttc cggcgggcca agggctaccc catcgacctg tactatctga    540

tggacctctc ctactccatg cttgatgacc tcaggaatgt caagaagcta ggtggcgacc    600

tgctccgggc cctcaacgag atcaccgagt ccggccgcat tggcttcggg tccttcgtgg    660

acaagaccgt gctgccgttc gtgaacacgc accctgataa gctgcgaaac ccatgcccca    720

acaaggagaa agagtgccag cccccgtttg ccttcaggca cgtgctgaag ctgaccaaca    780

actccaacca gtttcagacc gaggtcggga agcagctgat ttccggaaac ctggatgcac    840

ccgagggtgg gctggacgcc atgatgcagg tcgccgcctg cccggaggaa atcggctggc    900

gcaacgtcac gcggctgctg gtgtttgcca ctgatgacgg cttccatttc gcgggcgacg    960

ggaagctggg cgccatcctg acccccaacg acggccgctg tcacctggag gacaacttgt   1020

acaagaggag caacgaattc gactacccat cggtgggcca gctggcgcac aagctggctg   1080

aaaacaacat ccagcccatc ttcgcggtga ccagtaggat ggtgaagacc tacgagaaac   1140

tcaccgagat catccccaag tcagccgtgg gggagctgtc tgaggactcc agcaatgtgg   1200

tccaactcat taagaatgct tacaataaac tctcctccag ggtcttcctg gatcacaacg   1260

ccctccccga caccctgaaa gtcacctacg actccttctg cagcaatgga gtgacgcaca   1320

ggaaccagcc cagaggtgac tgtgatggcg tgcagatcaa tgtcccgatc accttccagg   1380

tgaaggtcac ggccacagag tgcatccagg agcagtcgtt tgtcatccgg gcgctgggct   1440

tcacggacat agtgaccgtg caggttcttc cccagtgtga gtgccggtgc cgggaccaga   1500

gcagagaccg cagcctctgc catggcaagg gcttcttgga gtgcggcatc tgcaggtgtg   1560

acactggcta cattgggaaa aactgtgagt gccagacaca gggccggagc agccaggagc   1620

tggaaggaag ctgccggaag gacaacaact ccatcatctg ctcagggctg gggggactgtg   1680

tctgcgggca gtgcctgtgc cacaccagcg acgtccccgg caagctgata tacgggcagt   1740
```

```
actgcgagtg tgacaccatc aactgtgagc gctacaacgg ccaggtctgc ggcggcccgg   1800

ggagggggct ctgcttctgc gggaagtgcc gctgccaccc gggctttgag ggctcagcgt   1860

gccagtgcga gaggaccact gagggctgcc tgaacccgcg gcgtgttgag tgtagtggtc   1920

gtggccggtg ccgctgcaac gtatgcgagt gccattcagg ctaccagctg cctctgtgcc   1980

aggagtgccc cggctgcccc tcaccctgtg gcaagtacat ctcctgcgcc gagtgcctga   2040

agttcgaaaa gggccccttt gggaagaact gcagcgcggc gtgtccgggc ctgcagctgt   2100

cgaacaaccc cgtgaagggc aggacctgca aggagaggga ctcagagggc tgctgggtgg   2160

cctacacgct ggagcagcag gacgggatgg accgctacct catctatgtg gatgagagcc   2220

gagagtgtgt ggcaggcccc aacatcgccg ccatcgtcgg gggcaccgtg gcaggcatcg   2280

tgctgatcgg cattctcctg ctggtcatct ggaaggctct gatccacctg agcgacctcc   2340

gggagtacag gcgctttgag aaggagaagc tcaagtccca gtggaacaat gataatcccc   2400

ttttcaagag cgccaccacg acggtcatga accccaagtt tgctgagagt taggagcact   2460

tggtgaagac aaggccgtca ggacccacca tgtctgcccc atcacgcggc cgagacatgg   2520

cttgccacag ctcttgagga tgtcaccaat taaccagaaa tccagttatt ttccgccctc   2580

aaaatgacag ccatggccgg ccgggtgctt ctgggggctc gtcgggggga cagctccact   2640

ctgactggca cagtctttgc atggagactt gaggagggag ggcttgaggt tggtgaggtt   2700

aggtgcgtgt ttcctgtgca agtcaggaca tcagtctgat taaaggtggt gccaatttat   2760

ttacatttaa acttgtcagg gtataaaatg acatcccatt aattatattg ttaatcaatc   2820

acgtgtatag aaaaaaaata aaacttcaat acaggctgtc catggaaaaa aaaaaaaaaa   2880

aaaaaaa                                                             2887
```

<210> SEQ ID NO 104
<211> LENGTH: 1902
<212> TYPE: DNA
<213> ORGANISM: Homo sapiens

<400> SEQUENCE: 104

```
ctggcgcgcg cggccctgcg ggtgacaggc aggcgggaag gggcggggcc tcgggcgggg     60

ccgccgtggg gaggagggcg gtgggagggg aggagtggag atggcggcgg cggcggctca    120

ggggggcggg ggcggggagc cccgtagaac cgaggggggtc ggcccggggg tcccggggga    180

ggtggagatg gtgaaggggc agccgttcga cgtgggcccg cgctacacgc agttgcagta    240

catcggcgag ggcgcgtacg gcatggtcag ctcggcctat gaccacgtgc gcaagactcg    300

cgtggccatc aagaagatca gccccttcga acatcagacc tactgccagc gcacgctccg    360

ggagatccag atcctgctgc gcttccgcca tgagaatgtc atcggcatcc gagacattct    420

gcgggcgtcc accctggaag ccatgagaga tgtctacatt gtgcaggacc tgatggagac    480

tgacctgtac aagttgctga aaagccagca gctgagcaat gaccatatct gctacttcct    540

ctaccagatc ctgcggggcc tcaagtacat ccactccgcc aacgtgctcc accgagatct    600

aaagccctcc aacctgctca tcaacaccac ctgcgacctt aagatttgtg atttcggcct    660

ggcccggatt gccgatcctg agcatgacca caccggcttc ctgacggagt atgtggctac    720

gcgctggtac cgggccccag agatcatgct gaactccaag ggctatacca agtccatcga    780

catctggtct gtgggctgca ttctggctga gatgctctct aaccggccca tcttccctgg    840

caagcactac ctggatcagc tcaaccacat tctgggcatc ctgggctccc catcccagga    900

ggacctgaat tgtatcatca acatgaaggc ccgaaactac ctacagtctc tgccctccaa    960
```

```
gaccaaggtg gcttgggcca agcttttccc caagtcagac tccaaagccc ttgacctgct   1020

ggaccggatg ttaaccttta accccaataa acggatcaca gtggaggaag cgctggctca   1080

cccctacctg gagcagtact atgacccgac ggatgagcca gtggccgagg agcccttcac   1140

cttcgccatg gagctggatg acctacctaa ggagcggctg aaggagctca tcttccagga   1200

gacagcacgc ttccagcccg gagtgctgga ggcccccctag cccagacaga catctctgca   1260

ccctggggcc tggacctgcc tcctgcctgc ccctctcccg ccagactgtt agaaaatgga   1320

cactgtgccc agcccggacc ttggcagccc aggccggggt ggagcatggg cctggccacc   1380

tctctccttt gctgaggcct ccagcttcag gcaggccaag gccttctcct ccccacccgc   1440

cctccccacg gggcctcggg acctcaggtg gccccagttc aatctcccgc tgctgctgct   1500

gcgcccttac cttccccagc gtcccagtct ctggcagttc tggaatggaa gggttctggc   1560

tgccccaacc tgctgaaggg cagaggtgga gggtgggggg cgctgagtag ggactcaggg   1620

ccatgcctgc ccccctcatc tcattcaaac cccaccctag tttccctgaa ggaacattcc   1680

ttagtctcaa gggctagcat ccctgaggag ccaggccggg ccgaatcccc tccctgtcaa   1740

agctgtcact tcgcgtgccc tcgctgcttc tgtgtgtggt gagcagaagt ggagctgggg   1800

ggcgtggaga gcccggcgcc cctgccacct ccctgacccg tctaatatat aaatatagag   1860

atgtgtctat ggctgaaaaa aaaaaaaaaa aaaaaaaaaa aa                       1902
```

<210> SEQ ID NO 105
<211> LENGTH: 2826
<212> TYPE: DNA
<213> ORGANISM: Homo sapiens

<400> SEQUENCE: 105

```
tcgagacctc aagggtagag gtgggcaccc ccgcctccgc acttttgctc ggggctccag     60

attgtagggc agggcggcgc ttctcggaaa gcgaaagccg gcggggcggg gcgggtgccg    120

caggagaaag aggaagcgct ggcagacaat gcgacccgac cgcgctgagg ctccaggacc    180

gcccgccatg gctgcaggag gtcccggcgc ggggtctgcg gccccggtct cctccacatc    240

ctcccttccc ctggctgctc tcaacatgcg agtgcggcgc cgcctgtctc tgttcttgaa    300

cgtgcggaca caggtggcgg ccgactggac cgcgctggcg gaggagatgg actttgagta    360

cttggagatc cggcaactgg agacacaagc ggaccccact ggcaggctgc tggacgcctg    420

gcagggacgc cctggcgcct ctgtaggccg actgctcgag ctgcttacca agctgggccg    480

cgacgacgtg ctgctggagc tgggacccag cattgaggag gattgccaaa agtatatctt    540

gaagcagcag caggaggagg ctgagaagcc tttacaggtg gccgctgtag acagcagtgt    600

cccacggaca gcagagctgg cgggcatcac cacacttgat gaccccctgg ggcatatgcc    660

tgagcgtttc gatgccttca tctgctattg ccccagcgac atccagtttg tgcaggagat    720

gatccggcaa ctggaacaga caaactatcg actgaagttg tgtgtgtctg accgcgatgt    780

cctgcctggc acctgtgtct ggtctattgc tagtgagctc atcgaaaaga ggtgccgccg    840

gatggtggtg gttgtctctg atgattacct gcagagcaag gaatgtgact tccagaccaa    900

atttgcactc agcctctctc caggtgccca tcagaagcga ctgatcccca tcaagtacaa    960

ggcaatgaag aaagagttcc ccagcatcct gaggttcatc actgtctgcg actacaccaa   1020

cccctgcacc aaatcttggt tctggactcg ccttgccaag gccttgtccc tgccctgaag   1080

actgttctga ggccctgggt gtgtgtgtat ctgtctgcct gtccatgtac ttctgccctg   1140

cctcctcctt tcgttgtagg aggaatctgt gctctactta cctctcaatt cctggagatg   1200
```

```
ccaacttcac agacacgtct gcagcagctg gacatcacat ttcatgtcct gcatggaacc   1260
agtggctgtg agtggcatgt ccacttgctg gattatcagc caggacacta tagaacagga   1320
ccagctgaga ctaagaagga ccagcagagc cagctcagct ctgagccatt cacacatctt   1380
caccctcagt ttcctcactt gaggagtggg atggggagaa cagagagtag ctgtgtttga   1440
atccctgtag gaaatggtga agcatagctc tgggtctcct gggggagacc aggcttggct   1500
gcgggagagc tggctgttgc tggactacat gctggccact gctgtgacca cgacactgct   1560
ggggcagctt cttccacagt gatgcctact gatgcttcag tgcctctgca caccgcccat   1620
tccacttcct ccttccccac agggcaggtg gggaagcagt ttggcccagc ccaaggagac   1680
cccaccttga gccttatttc ctaatgggtc cacctctcat ctgcatcttt cacacctccc   1740
agcttctgcc caaccttcag cagtgacaag tccccaagag actcgcctga gcagcttggg   1800
ctgcttttca tttccacctg tcaggatgcc tgtggtcatg ctctcagctc cacctggcat   1860
gagaagggat cctggcctct ggcatattca tcaagtatga gttctgggga tgagtcactg   1920
taatgatgtg agcagggagc cttcctccct gggccacctg cagagagctt tcccaccaac   1980
tttgtacctt gattgcctta caaagttatt tgtttacaaa cagcgaccat ataaaagcct   2040
cctgccccaa agcttgtggg cacatgggca catacagact cacatacaga cacacacata   2100
tatgtacaga catgtactct cacacacaca ggcaccagca tacacacgtt tttctaggta   2160
cagctcccag gaacagctag gtgggaaagt cccatcactg agggagccta accatgtccc   2220
tgaacaaaaa ttgggcactc atctattcct tttctcttgt gtccctactc attgaaacca   2280
aactctggaa aggacccaat gtaccagtat ttatacctct aatgaagcac agagagagga   2340
agagagctgc ttaaactcac acaacaatga actgcagaca cagctgttct ctccctctct   2400
ccttcccaga gcaatttata ctttaccctc aggctgtcct ctggggagaa ggtgccatgg   2460
tcttaggtgt ctgtgcccca ggacagaccc taggacccta aatccaatag aaaatgcata   2520
tctttgctcc actttcagcc aggctggagc aaggtacctt ttcttaggat cttgggaggg   2580
aatggatgcc cctctctgca tgatcttgtt gaggcattta gctgccatgc acctgtcccc   2640
ctttaatact gggcatttta aagccatctc aagaggcatc ttctacatgt tttgtacgca   2700
ttaaaataat ttcaaagata tctgagaaaa gccgatattt gccattcttc ctatatcctg   2760
gaatatatct tgcatcctga gtttataata ataaataata ttctaccttg gaaaaaaaaa   2820
aaaaaa                                                              2826
```

<210> SEQ ID NO 106
<211> LENGTH: 1669
<212> TYPE: DNA
<213> ORGANISM: Homo sapiens

<400> SEQUENCE: 106

```
ctccctcagc aaggacagca gaggaccagc taagagggag agaagcaact acagaccccc     60
cctgaaaaca accctcagac gccacatccc ctgacaagct gccaggcagg ttctcttcct    120
ctcacatact gacccacggc tccaccctct ctcccctgga aaggacacca tgagcactga    180
aagcatgatc cgggacgtgg agctggccga ggaggcgctc cccaagaaga caggggggcc    240
ccagggctcc aggcggtgct tgttcctcag cctcttctcc ttcctgatcg tggcaggcgc    300
caccacgctc ttctgcctgc tgcactttgg agtgatcggc ccccagaggg aagagttccc    360
cagggacctc tctctaatca gccctctggc ccaggcagtc agatcatctt ctcgaacccc    420
gagtgacaag cctgtagccc atgttgtagc aaaccctcaa gctgaggggc agctccagtg    480
```

```
gctgaaccgc cgggccaatg ccctcctggc caatggcgtg gagctgagag ataaccagct    540

ggtggtgcca tcagagggcc tgtacctcat ctactcccag gtcctcttca agggccaagg    600

ctgcccctcc acccatgtgc tcctcaccca caccatcagc cgcatcgccg tctcctacca    660

gaccaaggtc aacctcctct ctgccatcaa gagcccctgc cagagggaga ccccagaggg    720

ggctgaggcc aagccctggt atgagcccat ctatctggga ggggtcttcc agctggagaa    780

gggtgaccga ctcagcgctg agatcaatcg gcccgactat ctcgactttg ccgagtctgg    840

gcaggtctac tttgggatca ttgccctgtg aggaggacga acatccaacc ttcccaaacg    900

cctcccctgc cccaatccct ttattacccc ctccttcaga caccctcaac ctcttctggc    960

tcaaaaagag aattgggggc ttagggtcgg aacccaagct tagaacttta agcaacaaga   1020

ccaccacttc gaaacctggg attcaggaat gtgtggcctg cacagtgaag tgctggcaac   1080

cactaagaat tcaaactggg gcctccagaa ctcactgggg cctacagctt tgatccctga   1140

catctggaat ctggagacca gggagccttt ggttctggcc agaatgctgc aggacttgag   1200

aagacctcac ctagaaattg acacaagtgg accttaggcc ttcctctctc cagatgtttc   1260

cagacttcct tgagacacgg agcccagccc tccccatgga gccagctccc tctatttatg   1320

tttgcacttg tgattattta ttatttattt attatttatt tatttacaga tgaatgtatt   1380

tatttgggag accggggtat cctgggggac ccaatgtagg agctgccttg gctcagacat   1440

gttttccgtg aaaacggagc tgaacaatag gctgttccca tgtagccccc tggcctctgt   1500

gccttctttt gattatgttt tttaaaatat ttatctgatt aagttgtcta aacaatgctg   1560

atttggtgac caactgtcac tcattgctga gcctctgctc cccaggggag ttgtgtctgt   1620

aatcgcccta ctattcagtg gcgagaaata aagtttgctt agaaaagaa              1669
```

```
<210> SEQ ID NO 107
<211> LENGTH: 948
<212> TYPE: DNA
<213> ORGANISM: Homo sapiens

<400> SEQUENCE: 107

attgtggtgc cttgtagctg tcccgggagc cctcagcagc agttggagct ggtgcacagg     60

aaggatgagg aagaccaggc tctgggggct gctgtggatg ctctttgtct cagaactccg    120

agctgcaact aaattaactg aggaaaagta tgaactgaaa gaggggcaga ccctggatgt    180

gaaatgtgac tacacgctag agaagtttgc cagcagccag aaagcttggc agataataag    240

ggacggagag atgcccaaga ccctggcatg cacagagagg ccttcaaaga attcccatcc    300

agtccaagtg ggaggatca tactagaaga ctaccatgat catggtttac tgcgcgtccg    360

aatggtcaac cttcaagtgg aagattctgg actgtatcag tgtgtgatct accagcctcc    420

caaggagcct cacatgctgt tcgatcgcat ccgcttggtg gtgaccaagg gtttttcagg    480

gacccctggc tccaatgaga attctaccca gaatgtgtat aagattcctc ctaccaccac    540

taaggccttg tgcccactct ataccagccc cagaactgtg acccaagctc cacccaagtc    600

aactgccgat gtctccactc ctgactctga aatcaacctt acaaatgtga cagatatcat    660

cagggttccg gtgttcaaca ttgtcattct cctggctggt ggattcctga gtaagagcct    720

ggtcttctct gtcctgtttg ctgtcacgct gaggtcattt gtaccctagg cccacgaacc    780

cacgagaatg tcctctgact tccagccaca tccatctggc agttgtgcca agggaggagg    840

gaggaggtaa aaggcaggga gttaataaca tgaattaaat ctgtaatcac cagctatttc    900

taaagtcagc gtctcacctt aaaaaaaaaa aaaaaaaaaa aaaaaaaa                 948
```